United States Patent
Conrad et al.

(10) Patent No.: US 12,220,474 B2
(45) Date of Patent: Feb. 11, 2025

(54) FORMULATIONS AND METHODS FOR TREATING HAIR

(71) Applicant: Two Lines Inc., Los Angeles, CA (US)

(72) Inventors: Allison Anne Conrad, Los Angeles, CA (US); Jason Timothy Small, Los Angeles, CA (US); Natalye Hinkson, Hayward, CA (US)

(73) Assignee: Two Lines Inc., Los Angeles, CA (US)

( * ) Notice: Subject to any disclaimer, the term of this patent is extended or adjusted under 35 U.S.C. 154(b) by 0 days.

(21) Appl. No.: 18/318,647

(22) Filed: May 16, 2023

(65) Prior Publication Data
US 2023/0372222 A1    Nov. 23, 2023

Related U.S. Application Data

(60) Provisional application No. 63/342,708, filed on May 17, 2022.

(51) Int. Cl.
| | | |
|---|---|---|
| A61K 8/64 | (2006.01) | |
| A61K 8/9789 | (2017.01) | |
| A61Q 5/00 | (2006.01) | |
| A61Q 5/02 | (2006.01) | |
| A61Q 5/12 | (2006.01) | |

(52) U.S. Cl.
CPC .............. *A61K 8/64* (2013.01); *A61K 8/9789* (2017.08); *A61Q 5/002* (2013.01); *A61Q 5/02* (2013.01); *A61Q 5/12* (2013.01); *A61K 2800/28* (2013.01); *A61K 2800/92* (2013.01)

(58) Field of Classification Search
None
See application file for complete search history.

(56) References Cited

U.S. PATENT DOCUMENTS

| | | | | |
|---|---|---|---|---|
| 6,447,762 B1 * | 9/2002 | Casado Galcera | ...... | A61Q 7/00 514/880 |
| 2018/0161258 A1 * | 6/2018 | Hindley | ................. | A61K 8/362 |

FOREIGN PATENT DOCUMENTS

| | | | | |
|---|---|---|---|---|
| CH | 718031 A2 | | 5/2022 | |
| CN | 110051597 A | | 7/2019 | |
| CN | 111265622 A | * | 6/2020 | |
| CN | 111388371 A | * | 7/2020 | |
| CN | 111481621 A | * | 8/2020 | .......... A61K 36/126 |
| CN | 111643446 A | | 9/2020 | |
| JP | S-61-33123 A | | 2/1986 | |
| JP | 2000198717 A | * | 7/2000 | |
| JP | 2020132577 A | * | 8/2020 | |
| WO | WO-2013/049644 A2 | | 4/2013 | |
| WO | WO-2013/049644 A3 | | 4/2013 | |

OTHER PUBLICATIONS

English translation of JP-2020132577-A (Year: 2020).*
English translation of CN-111481621-A (Year: 2020).*
Hu et al. "Antioxidant Activity of Extracts of Black Sesame Seed (*Sesamum indicum* L.) by Supercritical Carbon Dioxide Extraction" J. Agric. Food Chem. 52;943-947 (Year: 2004).*
Happi "Go Away Gray!" <https://www.happi.com/contents/view_suppliers-corner/2020-09-16/go-away-gray/> (Year: 2020).*
English translation of CN-111265622-A (Year: 2020).*
Shin JY, Choi YH, Kim J, Park SY, Nam YJ, Lee SY, Jeon JH, Jin MH, Lee S. Polygonum multiflorum extract support hair growth by elongating anagen phase and abrogating the effect of androgen in cultured human dermal papilla cells. BMC Complement Med Ther. May 12;20(1):144. (Year: 2020).*
English translation of JP-2000198717-A (Year: 2000).*
English translation of CN-111388371-A (Year: 2020).*
Lan, Y. et al. (2014). "Essential oil from Zanthoxylum bungeanum Maxim, and its main components used as transdermal penetration enhancers: a comparative study," J. Zhejiang Univ. Sci. B. 15:940-952.
International Search Report and Written Opinion of the International Searching Authority mailed on Nov. 8, 2023, for PCT Application No. PCT/US2023/067080, 26 total pages.
GREYVERSE™ (2024). "GREYVERSE™ contains an innovative a-MSH biomimetic peptide able to act on the different causes of the hair greying process. It offers an unprecedented efficient solution to prevent, stop, and reverse this inevitable sign of aging," Lucas Meyer Cosmetics, 4 total pages.

* cited by examiner

*Primary Examiner* — Nicole P Babson
(74) *Attorney, Agent, or Firm* — COOLEY LLP

(57) ABSTRACT

Provided herein are formulations and methods for conferring at least one beneficial hair care effect. The formulations a unique combination of non-synthetic extracts, and may also comprise palmitoyl tetrapeptide-20 and conditioning agents. Beneficial hair care effects conferred include amelioration of hair depigmentation, promotion and maintenance of hair pigmentation, and enhanced hair growth and volume.

24 Claims, 8 Drawing Sheets

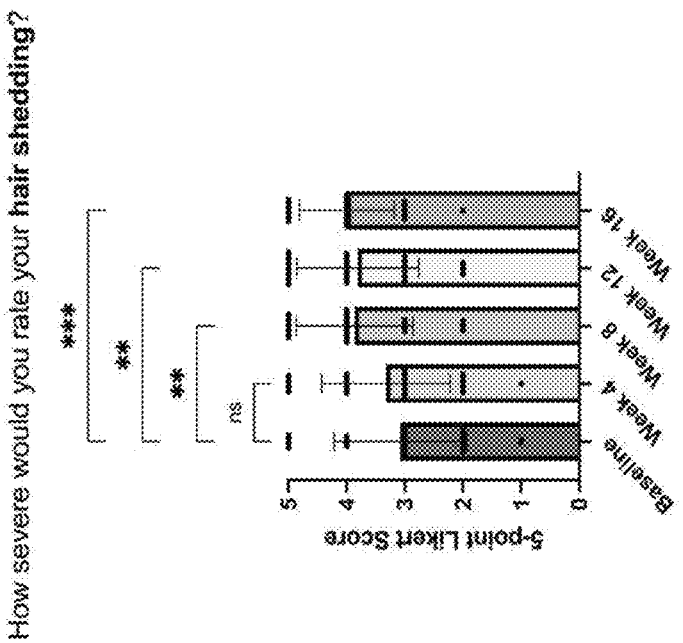
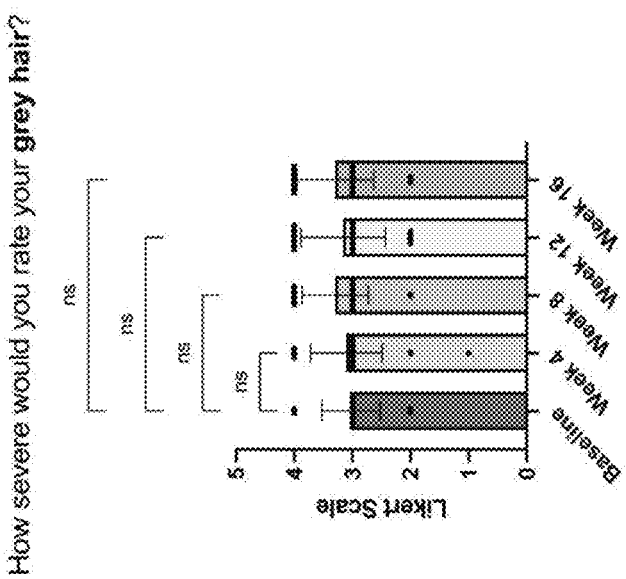
FIG. 1A  Consumer Study of Shampoo and conditioner; Results from All Subjects
FIG. 1B  Consumer Study of Shampoo and conditioner; Results from All Subjects

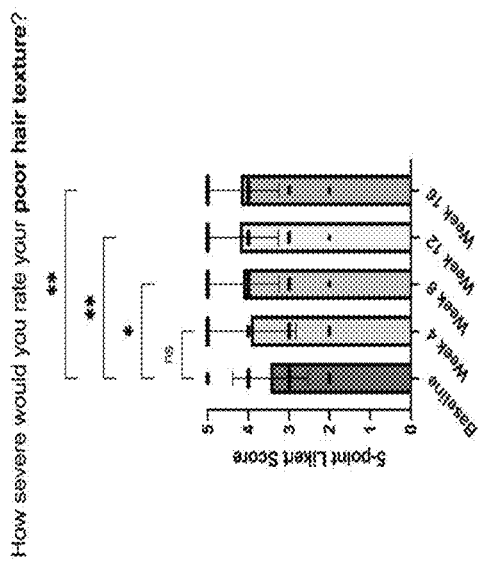
FIG. 1C Consumer Study of Shampoo and conditioner; Results from All Subjects
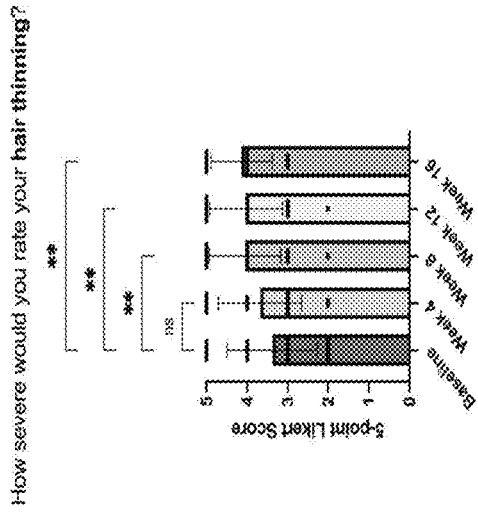
FIG. 1D Consumer Study of Shampoo and conditioner; Results from All Subjects
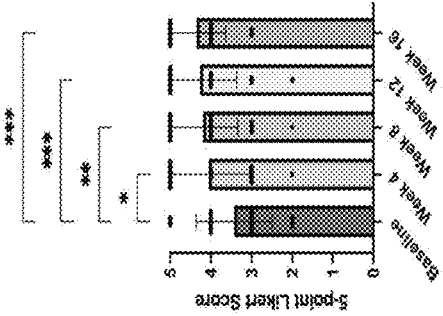
FIG. 1E Consumer Study of Shampoo and conditioner; Results from All Subjects FIG. 2 Consumer Study of Shampoo and conditioner; Results from All Subjects

| Question | BASELINE | WEEK 4 | WEEK 8 | WEEK 12 | WEEK 16 | WEEK 16 vs. BASELINE Change | WEEK 16 vs. BASELINE P value | Test | % Change |
|---|---|---|---|---|---|---|---|---|---|
| How severe would you rate your hair greying? | 3.03 | 3.11 | 3.30 | 3.16 | 3.30 | 0.27 | 0.3361 | Friedman | 8.93 |
| How severe would you rate your hair shedding? | 3.08 | 3.32 | 3.86 | 3.81 | 4.00 | 0.92 | <0.0001 | Friedman | 29.82 |
| How severe would you rate your hair thinning? | 3.38 | 3.68 | 4.05 | 4.03 | 4.14 | 0.76 | 0.0017 | Friedman | 22.40 |
| How severe would you rate your poor hair texture? | 3.46 | 3.95 | 4.14 | 4.22 | 4.19 | 0.73 | 0.0049 | Friedman | 21.09 |
| How severe would you rate your poor hair strength? | 3.43 | 4.05 | 4.19 | 4.27 | 4.35 | 0.92 | 0.0007 | ANOVA | 26.77 |

FIG. 3 Consumer Study of Shampoo and conditioner; Results from All Subjects

| Question | Combined Agree | | | |
|---|---|---|---|---|
| | WEEK 4 | WEEK 8 | WEEK 12 | WEEK 16 |
| I have noticed fewer grey hairs | 32.4% | 55.3% | 71.1% | 57.9% |
| I have noticed a reduction in new grey hairs compared to before taking the product. | 37.8% | 55.3% | 68.4% | 65.8% |
| I have noticed a reduction in shedding. | 40.5% | 55.3% | 60.5% | 63.2% |
| My hair is visibly fuller. | 48.6% | 60.5% | 55.3% | 71.1% |
| My hair looks thicker. | 48.6% | 71.1% | 55.3% | 65.8% |
| I have noticed an improvement in hair growth. | 43.2% | 65.8% | 50.0% | 57.9% |
| My hair looks healthier. | 73.0% | 73.7% | 71.1% | 73.7% |
| My hair feels softer. | 81.1% | 78.9% | 78.9% | 71.1% |
| My hair grows faster. | 29.7% | 50.0% | 39.5% | 47.4% |
| My hair is stronger. | 43.2% | 63.2% | 57.9% | 68.4% |
| I have noticed an improvement in hair texture. | 56.8% | 68.4% | 68.4% | 73.7% |
| I would like to continue using this product | | | | 89.5% |
| I would recommend this product to a friend | | | | 86.8% |
| AVERAGE AGREE OVER ALL QUESTIONS | 48.6% | 63.4% | 61.5% | 65.1% |

FIG. 4A  Preliminary Results of Double-Blind Placebo Controlled Clinical Study

| Treatment | Time Point | N | Mean | Minimum | Median | Maximum |
|---|---|---|---|---|---|---|
| Number of grey hairs | | | | | | |
| Cell 1 | Baseline | 17 | 3.12 | 2.00 | 3.00 | 5.00 |
| | Week 12 | 17 | 2.76 | 1.00 | 2.00 | 7.00 |
| | Week 24 | | | | | |
| Cell 2 | Baseline | 14 | 2.93 | 2.00 | 2.00 | 6.00 |
| | Week 12 | 14 | 2.64 | 1.00 | 2.00 | 7.00 |
| | Week 24 | | | | | |
| Cell 3 | Baseline | 15 | 2.60 | 2.00 | 2.00 | 5.00 |
| | Week 12 | 15 | 2.47 | 1.00 | 2.00 | 5.00 |
| | Week 24 | | | | | |

Cell 1 = NTG and TTR; Cell 2 = NTG and placebo TTR; Cell 3 = Placebo NTG and Placebo TTTR

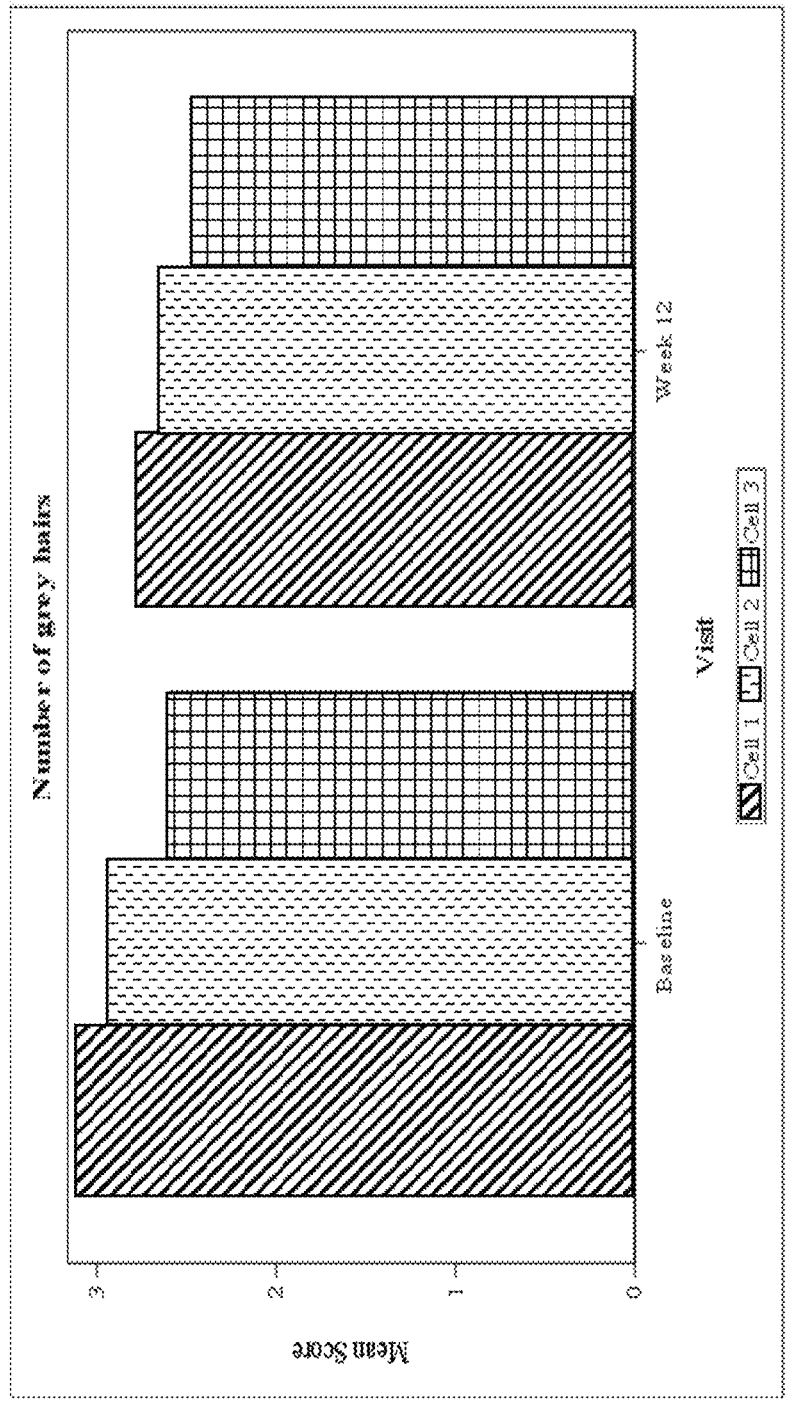
FIG. 4B Preliminary Results of Double-Blind Placebo Controlled Clinical Study
Cell 1 = NTG and TTR; Cell 2 = NTG and placebo TTR; Cell 3 = Placebo NTG and Placebo TTTR FIG. 5A Preliminary Results of Double-Blind Placebo Controlled Clinical Study

| Treatment | Time Point | N | Mean | Minimum | Median | Maximum |
|---|---|---|---|---|---|---|
| What changes have you noticed in the amount of your grey hair since the baseline visit? | | | | | | |
| Cell 1 | Week 12 | 3 | 1.67 | 1.00 | 2.00 | 2.00 |
| Cell 2 | Week 12 | 3 | 0.33 | 0.00 | 0.00 | 1.00 |
| Cell 3 | Week 12 | 5 | -0.80 | -3.00 | -2.00 | 2.00 |

Cell 1 = NTG and TTR; Cell 2 – NTG and placebo TTR; Cell 3 = Placebo NTG and Placebo TTTR

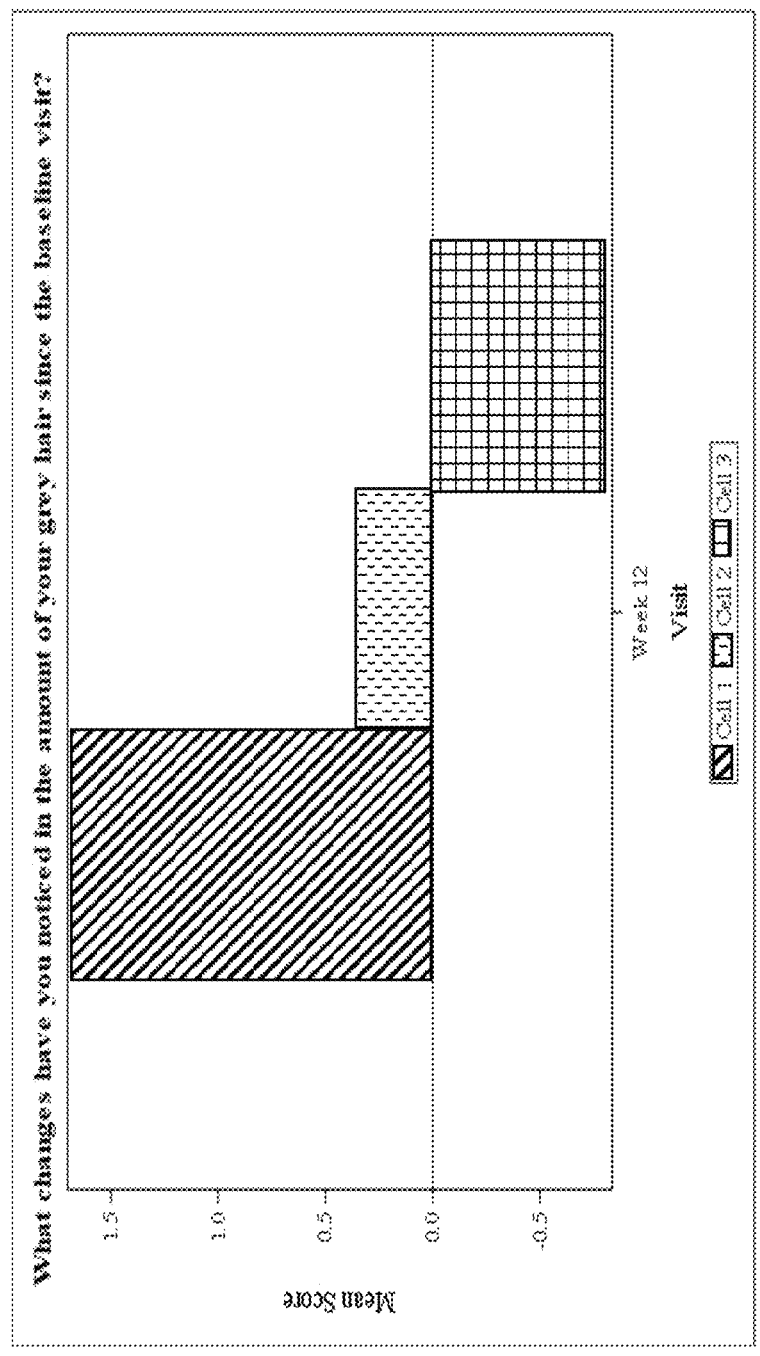
FIG. 5B Preliminary Results of Double-Blind Placebo Controlled Clinical Study
Cell 1 = NTG and TTR; Cell 2 – NTG and placebo TTR; Cell 3 = Placebo NTG and Placebo TTTR

FORMULATIONS AND METHODS FOR TREATING HAIR

CROSS-REFERENCE TO RELATED APPLICATIONS

This application claims priority to U.S. Provisional Application No. 63/342,708 filed May 17, 2022, the disclosure of which is incorporated herein by reference in its entirety.

BACKGROUND

Hair color in mammals, including humans, is determined by the type and amount of pigmentation present in hair follicles. The source of hair follicle pigment is melanin, of which there are two types: eumelanin which results in black-brown hair color, and pheomelanin which results in red-brown and red-yellow hair color. The color variation found in hair arises as a result of varied ratios and concentrations of eumelanin and pheomelanin in the hair shaft. Melanin is synthesized by melanocytes in hair follicles; as the hair is being formed, melanocytes inject melanin into the hair shafts, contributing to the overall color of hair.

The process of hair pigmentation is related to and concurrent with the process of hair growth. Hair growth is cyclic and has three phases: anagen, catagen, and telogen. Each strand of hair follows its own cycle independent from others in the hair. Anagen is the active growth stage of the hair, when the hair shaft physically grows longer by about 1 cm per month. The anagen stage is also when melanocytes impart melanin to the hair shaft. The anagen phase typically lasts several years and is influenced by genetics and environmental factors. The longer a hair strand is in the anagen phase, the longer the resulting hair shaft will be. The next phase is the catagen, or the transition stage. The catagen stage is characterized by the cessation of hair growth. At this stage, the hair follicle shrinks, and the hair papilla detaches, cutting off the hair strand from its nourishing blood supply. It is also at this stage when melanin production ceases. The last phase is the telogen stage, when the hair is shed naturally. The cycle then begins again with the anagen growth stage. At any given time, the number of hair strands that are in anagen and catagen stages determine the density of hair, whereas the composition of each hair strand determines hair volume and color.

As an individual ages, follicular stem cell reservoirs that maintain the supply of new hair follicles are depleted, resulting in loss of hair, deterioration of hair health, and a cessation of melanin production. Both men and women generally experience some degree of hair loss as they age. Deterioration of hair health may include for example, increased dullness, coarseness, dryness, and a loss of volume and shine. Greying hair, i.e., hair melanin loss, is particularly common, with about 74% of people experiencing some degree of grey hair between the ages of 45-65 years old. Although genetics are known to influence the age of onset of hair melanin loss, only one gene has been identified to cause grey hair (IRF4), and this gene only accounts for about 30% of greying. In addition, genetics have not been shown to correlate with the rate of hair melanin loss in humans, and while some causes of melanin loss are reversible (e.g., nutritional deficiencies), others are not. Other risk factors for melanocyte death are thought to be related to environmental factors. In fact, recently the effects of reactive oxygen species (ROS) in the environment been shown to affect the death of pigment producing melanocytes in hair follicles. ROS targeting melanocytes in hair follicles may come from a number of sources, including ultraviolet (UV) light, pollution, emotional stress, e.g., as a rapid cortisol response, alcohol consumption, cigarette smoking, and as a natural product of hair growth, hydrogen peroxide.

Although formulations have been developed that are designed to reduce ROS associated melanocyte death or improve other aspects of hair health, efficacious delivery of such formulations has been limited. Indeed, treatment of hair health has proven to be an extremely challenging problem to solve, as different factors affect different aspects of hair health, and different routes of administration may be required to treat more than one aspect of hair health. For example, hair follicles reside deep within the epidermis, in a thick reticular dermis layer containing blood vessels, glands, lymphatic ducts, nerves, and fat cells. Delivery agents that are able to reach this level of dermis often result in skin inflammation, which causes discomfort and can exhibit the counter-productive effect of further exacerbating hair loss or loss of pigment. Therefore, a need exists for hair treatments that are well tolerated, effective, and promote at least one beneficial hair care effect for users.

SUMMARY

The invention of the disclosure comprises formulations for conferring at least one beneficial hair care effect to a subject in need thereof. In some instances, the formulations provided herein comprise palmitoyl tetrapeptide-20 and an extract selected from the group consisting of *Zanthoxylum bungeanum*, *Humulus lupulus*, *Sesamum indicum* seed, *Panax ginseng* root, *Polygonum multiflorum*, and combinations thereof a conditioning agent; and an excipient.

In some embodiments, the palmitoyl tetrapeptide-20 is 0.5 to 4% W/W of the formulation.

In some embodiments, the extract is 0.0005 to 3% W/W of the formulation.

In some embodiments, the conditioning agent is 0.01 to 4% W/W of the formulation. In some embodiments, the conditioning agent is panthenol. In some embodiments, the conditioning agent is biotin. In some embodiments, the conditioning agent is 1,2 hexanediol. In some embodiments, the conditioning agent is caprylyl glycol. In some embodiments, the conditioning agent is hydrolyzed barley protein. In some embodiments, the conditioning agent is Chios mandarin extract. In some embodiments, the conditioning agent is *Glycine soja* germ extract. In some embodiments, the conditioning agent is *Wasabia japonica* leaf extract. In some embodiments, the conditioning agent is *Coffea arabica* seed extract. In some embodiments, the conditioning agent is caffeine. In some embodiments, the conditioning agent is amodimethicone. In some embodiments, the conditioning agent is guar hydroxypropyltrimonium chloride. In some embodiments, the formulation of the disclosure further comprises at least two conditioning agents.

In some embodiments, the excipient is 0.1 to 40% W/W of the formulation. In some embodiments, the excipient is glycerin. In some embodiments, the excipient is butylene glycol. In some embodiments, the excipient is hydroxyethylcellulose. In some embodiments, the excipient is cocamidopropyl betaine. In some embodiments, the formulation of the disclosure further comprises at least two excipients.

In some embodiments, the extract is 0.5 to 3% W/W of the formulation.

In some embodiments, the formulation further comprises a cleanser, a surfactant, and a preservative.

In some embodiments, the cleanser is 0.1 to 6% W/W of the formulation. In some embodiments, the cleanser is sodium lauroyl methyl isethionate. In some embodiments, the cleanser is citric acid. In some embodiments, the formulation of the disclosure further comprises at least two cleansers.

In some embodiments, the surfactant is 1 to 10% W/W of the formulation. In some embodiments, the surfactant is sodium cocoyl isethionate. In some embodiments, the formulation of the disclosure further comprises at least two surfactants.

In some embodiments, the preservative is 0.01 to 1% W/W of the formulation. In some embodiments, the preservative is sodium benzoate. In some embodiments, the preservative is potassium sorbate. In some embodiments, the preservative is ethylhexylglycerin. In some embodiments, the formulation of the disclosure further comprises at least two preservatives.

In some embodiments, the formulation comprises *Ononis spinosa* root extract and/or *Avena strigosa* seed extract. In some embodiments, the formulation comprises *Ononis spinosa* root extract and/or *Avena strigosa* seed extract are formulated as Agreynist®.

In some embodiments, the formulation of the disclosure further comprises non-synthetic essential oils. In some embodiments the formulation of the disclosure further comprises sage and cedar non-synthetic essential oils. In some embodiments, the fragrance is 0.1 to 3% W/W. In some embodiments, the fragrance is sage. In some embodiments, the fragrance is cedar. In some embodiments, the formulation of the disclosure further comprises at least two fragrances.

In some embodiments the formulation of the disclosure is formulated as a serum. In some embodiments, the serum has a pH of about 4-6. In some embodiments, the serum has a pH of about 5.3 In some embodiments, the serum has a pH of about 5-8. In some embodiments, the serum has a pH of about 6.5. In some embodiments, the serum has a viscosity of about 100-1000 centipoise (cps). In some embodiments, the serum has a viscosity of about 500 cps.

In some embodiments, the serum delivers high concentrations of ingredients. In some embodiments, the serum can be sprayed for topical application. In some embodiments, the serum can be applied daily.

In some embodiments, the formulation of the disclosure is formulated as a shampoo. In some embodiments, the shampoo has a pH of about 4-6. In some embodiments, the shampoo has a pH of about 4.9. In some embodiments, the shampoo has a viscosity of about 1000-5000 centipoise (cps). In some embodiments, the shampoo has a viscosity of about 2900 cps.

In some embodiments, the shampoo creates a rich foam. In some embodiments, the shampoo can be massaged into the scalp. In some embodiments, the shampoo can be rinsed with water. In some embodiments, the shampoo is a dry shampoo. In some embodiments, the shampoo does not cause irritation.

In some embodiments, the formulation of the disclosure is formulated as a conditioner.

In some embodiments, the formulation of the disclosure is formulated as an exfoliator. In some embodiments, the exfoliant has a pH of about 4-6. In some embodiments, the exfoliant has a viscosity of about 25,000-50,000 cps.

In some aspects, provided herein is a conditioner comprising one or more extracts selected from the group consisting of *Zanthoxylum bungeanum, Humulus lupulus, Sesamum indicum* seed, *Panax ginseng* root, and *Polygonum multiflorum*. In some embodiments, the conditioner has a pH of about 4-6. In some embodiments, the conditioner has a pH of about 4.8. In some embodiments, the conditioner has a viscosity of about 8,000-25,000 cps. In some embodiments, the conditioner has a viscosity of about 15,000 cps.

In some aspects, provided herein is a topical hair care formulation comprising: at least two extracts selected from the group consisting of *Zanthoxylum bungeanum, Humulus lupulus, Sesamum indicum* seed, *Panax ginseng* root, and *Polygonum multiflorum*, and combinations thereof and an excipient. In some embodiments, the formulation promotes at least one beneficial hair care effect in a mammalian subject. In some embodiments, the formulation is used in combination with another hair follicle treatment to improve the delivery and/or efficacy of the treatment Some embodiments of the disclosure comprise a method for promoting at least one beneficial hair care effect in a mammalian subject, comprising applying to the mammalian subject a therapeutically effective amount of a formulation comprising palmitoyl tetrapeptide-20 and an extract selected from the group consisting of *Zanthoxylum bungeanum, Humulus lupulus, Sesamum indicum* seed, *Panax ginseng* root, *Polygonum multiflorum*, and combinations thereof.

In some embodiments, the method further comprises priming the scalp prior to applying the formulation of the disclosure. In some embodiments, priming the scalp comprises applying one or more of the group consisting of panthenol, *Glycine soja* germ extract, and *Wasabia japonica* leaf extract.

In some embodiments, the method affects facial hair or body hair. In some embodiments, the method affects facial hair. In some embodiments, the facial hair is eyebrow hair, eyelash hair, mustache hair, cheek hair, beard hair, lower lip hair, goatee hair, whiskers, sideburns, ear hair, nose hair, or combinations thereof. In some embodiments, the method affects body hair. In some embodiments, the body hair is head hair, neck hair, chest hair, shoulder hair, arm hair, axillary hair, hand hair, abdominal hair, back hair, pubic hair, gluteal hair, perineal hair, thigh hair, leg hair, foot hair, or combinations thereof.

In some embodiments, the formulation of the method further comprises 0.5 to 2% W/W panthenol. In some embodiments, the formulation of the method further comprises 0.5 to 2% W/W Chios mandarin extract. In some embodiments, the formulation of the method further comprises 0.5 to 4% W/W *Glycine soja* germ extract. In some embodiments, the formulation of the method further comprises 0.5 to 2% W/W *Wasabia japonica* leaf extract.

In some embodiments, the at least one beneficial hair care effect of the method is selected from the group consisting of ameliorating depigmentation, inducing pigmentation, promoting pigmentation, maintaining pigmentation, and combinations thereof. In some embodiments, the at least one beneficial hair care effect of the method is selected from the group consisting of thicker hair shafts, stronger hair shafts, denser hair, more hair volume, and combinations thereof.

In some embodiments, the formulation of the method is temporarily applied. In some embodiments, 1 to 3 mL of the formulation of the method is applied at a time. In some embodiments, 2 mL of the formulation of the method is applied at a time. In some embodiments, the formulation of the method is administered topically. In some embodiments, the formulation of the method is applied for 1-3 minutes. In some embodiments, the formulation of the method is applied for at least 3 minutes. In some embodiments, the formulation of the method is applied at least 1-2 times per day. In some embodiments, the formulation of the method is applied at least 3 times per day. In some embodiments, the formulation of the method is applied prior to loss of hair pigmentation. In some embodiments, the formulation of the method is applied after loss of hair pigmentation. In some embodiments, the formulation of the method is applied daily for at least 5 months. In some embodiments, the formulation of the method is applied daily for at least 1 month.

In some embodiments, the method further comprises applying a conditioner.

In some embodiments, the method further comprises administering an oral supplement. In some embodiments, the oral supplement has at least one beneficial hair care effect. In some embodiments, the supplement is ingested at least once a day. In some embodiments, the supplement is ingested at least once every 2 days. In some embodiments, the supplement is ingested at least once every 3 days. In some embodiments, the supplement is ingested at least once every 4 to 6 days. In some embodiments, the supplement is ingested at least once every 7 days.

BRIEF DESCRIPTION OF THE DRAWINGS

FIGS. 1A-1E show that an exemplary shampoo and exemplary conditioner, Arey WASH and Arey SMOOTH, significantly improved the perception of hair shedding (FIG. 1B), thinning (FIG. 1C), texture (FIG. 1D), and strength (FIG. 1E) over time. Also shown is the perception of greying hair over time (FIG. 1A). Subjects self-scored a range of hair health parameters on a 5-point Likert scale at baseline and each check-in point. Each data set was tested for normality and a repeated measure one-way ANOVA (parametric) or Friedman (nonparametric) analysis was conducted between the baseline and each check-in point. An increase in score reports a beneficial improvement of that hair parameter during the study period. Data is graphed as group means with standard deviation. ns=P>0.05, *=P<0.05, =P<0.01, *=P<0.001.

FIG. 2 shows the mean 5-point Likert scores at each time point for an exemplary shampoo and exemplary conditioner, Arey WASH and Arey SMOOTH, as described in Example 3. An increase in score reports a beneficial improvement of that hair parameter during the study period.

FIG. 3. shows participant responses to each question regarding the use of an exemplary shampoo and exemplary conditioner, Arey WASH and Arey SMOOTH, as described in Example 3. 'Combined agree' represents the % of participants who responded 'agree' or 'strongly agree' to the given statement reporting on a specific hair parameter improvement during the given study period. 'Average agree overall questions' represents the average % of participants who responded 'agree' or 'strongly agree' (combined agree) across all the listed statements reporting on hair parameters in the given study period (excluding 'I would like to continue using this product' and 'I would recommend this product to a friend'). It provides a measure of the average overall improvement in hair parameters for the given time point.

FIGS. 4A and 4B are a Table (FIG. 4A) and graph (FIG. 4B) showing the number of grey hairs per study cell, at baseline and at week 12, as described in the clinical study of an oral supplement and topical serum of Example 2.

FIGS. 5A and 5B are a Table (FIG. 5A) and graph (FIG. 5B) showing the changes observed in the amount of grey hair over time since baseline by the participant, as described in the clinical study of an oral supplement and topical serum of Example 2.

DETAILED DESCRIPTION

Provided herein are formulations and methods that surprisingly address multiple aspects of hair health, for example, hair thickness, hair shine, hair pigmentation, e.g. to counter hair greying, and hair volume. The formulations and methods of the disclosure comprise one or more of *Zanthoxylum bungeanum, Humulus lupulus, Sesamum indicum* seed, *Panax ginseng* root, or *Polygonum multiflorum* to confer at least one beneficial effect to the health of the hair of a subject. In some embodiments, one or more of *Zanthoxylum bungeanum, Humulus lupulus, Sesamum indicum* seed, *Panax ginseng* root, or *Polygonum multiflorum* improve penetration of a component, e.g., an additional component, through the epidermis to a hair follicle, and also reduce skin inflammation, thereby increasing the effectiveness of the component. In some embodiments, the formulations and methods of the disclosure improve the ability of an additional component to be appropriately absorbed and treat a hair follicle, e.g., palmitoyl tetrapeptide-20, resulting in improved hair health.

The formulations provided herein are substantially made of natural and organic ingredients. In some embodiments, the formulations are designed to stimulate overall hair health, and to thicken and strengthen hair shafts and increase the volume of the hair.

In some embodiments, the formulations provided herein comprise palmitoyl tetrapeptide-20 and one or more extracts of *Zanthoxylum bungeanum, Humulus lupulus, Sesamum indicum* seed, *Panax ginseng* root, or *Polygonum multiflorum* and are designed to improve hair health, with effects including but not limited to: ameliorating depigmentation, inducing pigmentation, promoting pigmentation, maintaining pigmentation, thickening hair shafts, strengthening hair shafts, increasing the density of the hair, increasing the volume of the hair, and combinations thereof.

In some embodiments, the formulations provided herein are designed to treat hair follicle pigment loss by increasing the effectiveness and delivery of palmitoyl tetrapeptide-20 peptide, and to reduce melanocyte death in hair follicles associated with reactive oxygen species (ROS). In some embodiments, the effectiveness of a peptide may be increased by improving the penetration of the peptide through skin to access the reticular dermis layer and/or by reducing inflammation of the epidermis. In some embodiments, the effectiveness of a peptide is increased by facilitating sustainable use by the subject and increasing the effectiveness of the product in the form of appropriate viscosity, odor, solubilization, and/or pH.

In some embodiments, the formulations provided herein, comprising one or more of *Zanthoxylum bungeanum, Humulus lupulus, Sesamum indicum* seed, *Panax ginseng* root, or *Polygonum multiflorum* extracts, are designed to improve the delivery and/or efficacy of any hair treatment, by improving penetration of the treatment through the skin to access the reticular dermis layer and/or by reducing inflammation of the epidermis.

In some embodiments, formulations of the disclosure are water-based. In some embodiments, water-based formulations provide improved penetration of the treatment through skin and reduce inflammation of the epidermis relative to comparable oil-based or emulsion-based formulations. In some embodiments, water-based formulations provide an improved and sustainable experience for a user, particularly for formulations used every day, or more than once a day on the scalp.

In some embodiments, the water-based formulations of the disclosure are optimized to increase the solubilization and effectiveness of one or more of *Zanthoxylum bungeanum, Humulus lupulus, Sesamum indicum* seed, *Panax ginseng* root, or *Polygonum multiflorum* extracts. Formulation of extracts of any of *Zanthoxylum bungeanum, Humulus lupulus, Sesamum indicum* seed, *Panax ginseng* root, or *Polygonum multiflorum* in water may be challenging to produce. For example, *Polygonum Multiflorum* does not solubilize easily in water, and affects the pH and color of a water-based formulation. However, formulations of appropriate color are often desired for hair treatments, and an unsuitable pH of a topical hair treatment formulation will affect the user's tolerance and may cause inflammation. Therefore, as provided herein, formulations and extracts comprising *Polygonum multiflorum* may be designed to optimize the solubility, color, and/or pH. Further, formulations and extracts comprising any of *Zanthoxylum bungeanum, Humulus lupulus, Sesamum indicum* seed, *Panax ginseng* root, or *Polygonum multiflorum*, may exhibit a prohibitive odor, in particular formulations and extracts comprising *Humulus lupulus*. The formulations and extracts provided herein may be designed to improve the odor without necessarily masking the odor with fragrance.

In some embodiments, optimization of the water-based formulations may increase the effectiveness, improve the pH of the formulation, improve the odor of the formulation, improve the color of the formulation, improve the viscosity of the formulation, improve the stability of the formulation, and/or improve the scaling of product production. In some embodiments, water-based formulations of the disclosure may be optimized to increase solubilization of an additional component, e.g., a peptide, e.g., palmitoyl tetrapeptide-20 peptide.

In some embodiments, the formulations of the disclosure comprising *Zanthoxylum bungeanum, Humulus lupulus, Sesamum indicum* seed, *Panax ginseng* root, and/or *Polygonum multiflorum*, provide improved hair treatments and better absorption of active ingredients relative to other treatments that contain one or more of fillers, stabilizers, thickening agents, oils, dyes, fragrances and/or additives, including but not limited to Dextran, Polyacrylate Crosspolymer-6, Phenoxyethanol, Caprylyl Glycol, Tocopheryl Acetate, Acetyl Tyrosine, Sodium Metabisulfite, Zinc Chloride, or Tetrasodium Glutamate Diacetate, Maltodextrin, Sodium Starch Octenylsuccinate, Scogin, Zantham Gum, Algin, Co-Polymers, or Silicones.

Without being bound by theory, the specific formulations of the disclosure demonstrate synergistic and surprising additive effects in penetrating the scalp and in treating or preventing scalp inflammation. In some embodiments, the formulations of the disclosure provide a synergistic or surprising additive effect of a peptide in combination with one or more extracts of *Zanthoxylum bungeanum, Humulus lupulus, Sesamum indicum* seed, *Panax ginseng* root, or *Polygonum multiflorum* one or more beneficial effects on hair. In some embodiments, the formulations of the disclosure provide a synergistic or surprising additive effect of the palmitoyl tetrapeptide-20 in combination with one or more extracts of *Zanthoxylum bungeanum, Humulus lupulus, Sesamum indicum* seed, *Panax ginseng* root, or *Polygonum multiflorum* on one or more beneficial effects on hair, including but not limited to: ameliorating depigmentation, inducing pigmentation, promoting pigmentation, maintaining pigmentation, thickening hair shafts, strengthening hair shafts, increasing the density of the hair, or increasing the volume of the hair.

The formulations of the disclosure can be incorporated into various types of hair products, depending on the type of treatment desired by the subject in need thereof.

In some embodiments, the formulations of the disclosure are formulated as serums. The serum-based formulations of the disclosure may be formulated to deliver a concentrated amount of active ingredients directly to the affected site. The serum-based formulations may be formulated to stay on the affected site once applied.

In some embodiments, the formulations of the disclosure are shampoo or conditioner-based formulations intended for use during the hair cleaning process. In some variations, the formulation is shampoo-based, and the shampoo-based formulation is formulated to deliver the active ingredients to hair follicles and hair strands while cleansing the hair.

Formulation of a shampoo with extracts of *Zanthoxylum bungeanum, Humulus lupulus, Sesamum indicum* seed, *Panax ginseng* root, and/or *Polygonum multiflorum* is challenging, as surfactants and additives common in shampoos may limit absorption by the skin of the extracts, and therefore the effectiveness of any of *Zanthoxylum bungeanum, Humulus lupulus, Sesamum indicum* seed, *Panax ginseng* root, and/or *Polygonum multiflorum* as a hair treatment. The shampoos of the instant disclosure were designed to stabilize the extracts of *Zanthoxylum bungeanum, Humulus lupulus, Sesamum indicum* seed, *Panax ginseng* root, and/or *Polygonum multiflorum* in a water-based formulation, and also to permit absorption of the extracts. In some embodiments, the shampoos of the instant disclosure were designed to both stabilize and confer absorption of a peptide, e.g., palmitoyl tetrapeptide-20 peptide.

In some embodiments, the formulation of the disclosure is a conditioner-based formulation. The conditioner-based formulations of the disclosure may be formulated to deliver the active ingredients as well as additional moisturizing agents to the hair. The shampoo-based and conditioner-based formulations may be formulated to be rinsed off after use or may be left on the hair and not rinsed off.

In some embodiments, the formulations of the disclosure are formulated as exfoliants. In some embodiments, improvement of the health of the hair follicle with an exfoliant increases the effectiveness of an additional topical treatment, e.g., a serum, shampoo, or conditioner.

In some embodiments, the formulations of the disclosure may be administered as an oral supplement. The oral supplement-based formulation may be designed to deliver the active ingredients as well as other vitamins, minerals, and nutrients through systemic delivery. Each of the types of formulations disclosed herein may be used individually or in combination with one another for achieving the desired beneficial hair care effect. In some embodiments, improvement of the health of the hair follicle with an oral supplement increases the effectiveness of the topical treatment, e.g., a serum, shampoo, or conditioner.

In some embodiments, the formulation of the disclosure confers the beneficial hair care effect of promoting the look and feel of the hair. For example, the at least one beneficial hair care effect may be thicker hair shafts, stronger hair shafts denser hair, more hair volume, or combinations thereof.

In some embodiments, the formulation of the disclosure confers at least one beneficial hair care effect to facial hair. The facial hair may include any suitable facial hair. For example, facial hair includes, but is not limited to, eyebrow hair, eyelash hair, mustache hair, cheek hair, beard hair, lower lip hair, goatee hair, whiskers, sideburns, ear hair, nose hair, or combinations thereof.

In some embodiments, the formulation of the disclosure confers at least one beneficial hair care effect to body hair. Body hair may include any suitable body hair. For example, body hair includes, but is not limited to neck hair, chest hair, shoulder hair, arm hair, axillary hair, hand hair, abdominal hair, back hair, pubic hair, gluteal hair, perineal hair, thigh hair, leg hair, foot hair, or combinations thereof.

In some embodiments, the beneficial hair care effect conferred by the formulations and methods described herein pertains to hair pigmentation. In some embodiments, the disclosure provides formulations and methods for ameliorating depigmentation of the hair shaft. In some embodiments, the disclosure provides formulations and methods for inducing pigmentation in the hair shaft. In some embodiments, the disclosure provides formulations and methods for promoting pigmentation in the hair shaft. In some embodiments, the disclosure provides formulations and methods for maintaining pigmentation in the hair shaft. In some embodiments, the disclosure provides formulations and methods for conferring at least one beneficial effect in any combination thereof of ameliorating depigmentation, inducing pigmentation, promoting pigmentation, and maintaining pigmentation in the hair shaft.

In some embodiments, the beneficial hair care effect conferred by the formulations and methods described herein pertains to hair growth. In some embodiments, the disclosure provides formulations and methods for conferring denser hair. In some embodiments, the disclosure provides formulations and methods for activating the growth cycle of hair follicles. In some embodiments, the disclosure provides formulations and methods for inducing the growth cycle of hair follicles. In some embodiments, the disclosure provides formulations and methods for maintaining the growth cycle of hair follicles. In some embodiments, the disclosure provides formulations and methods for preventing the loss of hair strands. In some embodiments, the beneficial hair care effect conferred by the compositions and methods described herein pertains to hair strength. In some embodiments, the disclosure provides formulations and methods for conferring stronger hair shafts. In some embodiments, the disclosure provides formulations and methods for conferring stronger thicker hair shafts. In some embodiments, the disclosure provides formulations and methods for conferring healthier hair shafts. In some embodiments, the beneficial hair care effect conferred by the compositions and methods described herein pertains to hair volume. In some embodiments, the disclosure provides formulations and methods for conferring more hair volume. In some embodiments, the disclosure provides formulations and methods for maintaining hair volume.

I. Serum-Based Formulations

As noted above, the formulations disclosed herein may be formulated as a serum. In this instance the formulation is formulated so as to be left in the scalp or any affected areas wherein a beneficial hair care effect is desired. In general, the serum-based formulations disclosed herein comprise palmitoyl tetrapeptide-20 and an extract selected from the group consisting of *Zanthoxylum bungeanum* fruit extract, *Humulus lupulus* extract, *Sesamum indicum* seed extract, *Panax ginseng* root extract, *Polygonum multiflorum* extract, and combinations thereof; a conditioning agent, and an excipient. In some embodiments, the formulations comprise *Ononis spinosa* root extract and/or *Avena strigosa* seed extract, e.g., as a formulation of Agreynist®.

The serum-based formulations are designed to confer at least one beneficial hair care effect as described above. In many instances, the serum-based formulations disclosed herein produce a surprising additive and/or synergistic on hair health, with effects including but not limited to: ameliorating depigmentation, inducing pigmentation, promoting pigmentation, maintaining pigmentation, thickening hair shafts, strengthening hair shafts, increasing the density of the hair, increasing the volume of the hair, increasing the volume of the hair, and combinations thereof.

In some embodiments, the serum-based formulations provided herein are designed to treat hair follicle pigment loss by increasing the effectiveness and delivery of palmitoyl tetrapeptide-20 peptide, which reduces melanocyte death in hair follicles associated with reactive oxygen species (ROS). In some embodiments, the effectiveness of a peptide may be increased by: improving the penetration of the peptide through skin to access the reticular dermis layer; reducing inflammation of the epidermis; or facilitating use by the subject and increasing effectiveness of the product in the form of appropriate viscosity, odor, solubilization, and/or pH. Further, the serum-based formulations provided herein are substantially made of natural and organic ingredients, and are designed to stimulate overall hair health, and to thicken and strengthen hair shafts.

In some embodiments, serum formulations of the disclosure are water-based. In some embodiments, water-based serum formulations provide improved penetration of a treatment through skin and also reduce inflammation of the epidermis relative to comparable oil-based or emulsion-based serum formulations. In some embodiments, water-based serum formulations provide an improved experience for a user, particularly for serum formulations used every day, or more than once a day.

In some embodiments, water-based serum formulations of the disclosure may be optimized to increase solubilization of one or more of *Zanthoxylum bungeanum*, *Humulus lupulus*, *Sesamum indicum* seed, *Panax ginseng* root, or *Polygonum multiflorum* extracts. In some embodiments, water-based serum formulations of the disclosure may be optimized to increase solubilization of an additional component, e.g., a peptide, e.g., palmitoyl tetrapeptide-20 peptide. In some embodiments, optimization of the water-based serum formulations may increase effectiveness, improve the pH of the formulation, improve the odor of the formulation, improve the color of the formulation, improve the viscosity of the formulation, improve the stability of the formulation, and/or improve the scaling of product production.

In some embodiments, the pH of the serum-based formulation is about 5.0 to about 8.0. In some embodiments, the pH of the serum-based formulation is about 6.0 to about 7.0. In some embodiments, the pH of the serum-based formulation is about 6.5. In some embodiments, the viscosity of the serum-based formulation is about 100-1000 centipoise (cps), as measured at 25° C. on a low viscosity torque (LVT) viscometer at 12 rotations per minute. In some embodiments, the viscosity of the serum-based formulation is about 250 to about 750 centipoise (cps). In some embodiments, the viscosity of the serum-based formulation is about 500 centipoise (cps).

In some embodiments, the pH of the serum-based formulation is about 4.0 to about 6.0. In some embodiments, the pH of the serum-based formulation is about 5.0 to about 5.5. In some embodiments, the pH of the serum-based formulation is about 5.3. In some embodiments, the viscosity of the serum-based formulation is about 250-2500 centipoise (cps), as measured at 25° C. on a low viscosity torque (LVT) viscometer at 12 rotations per minute. In some embodiments, the viscosity of the serum-based formulation is about 250 to about 750 centipoise (cps). In some embodiments, the viscosity of the serum-based formulation is about 500 centipoise (cps).

II. Peptides, e.g., Palmitoyl Tetrapeptide-20

In some embodiments, the formulation of the disclosure comprises a peptide, e.g., palmitoyl tetrapeptide-20. Palmitoyl tetrapeptide-20 is a biomimetic peptide that acts as an agonist of α-melanocyte-stimulating hormone (α-MSH). The ligand α-MSH and its receptor melanocortin 1 receptor (MC1-R) are the key regulators of melanin pigment generation in hair. In some embodiments, the palmitoyl tetrapeptide-20 of the disclosure is a biomimetic of α-MSH. In some embodiments, the palmitoyl tetrapeptide-20 binds MC1-R on the surface of melanocytes. In some embodiments, the palmitoyl tetrapeptide-20 stimulates melanin production in melanocytes. In some embodiments, the palmitoyl tetrapeptide-20 reduces the effects of reactive oxygen species on melanocytes. In some embodiments, the palmitoyl tetrapeptide-20 reduces apoptosis or cell stress signaling in melanocytes.

In some embodiments, the palmitoyl tetrapeptide-20 induces melanocytes to inject melanin into the hair shaft. In some embodiments, the palmitoyl tetrapeptide-20 induces pigmentation in the hair. In some embodiments, the palmitoyl tetrapeptide-20 stimulates catalase expression. In some embodiments, the palmitoyl tetrapeptide-20-induced catalase lowers oxidative stress. In some embodiments, the palmitoyl tetrapeptide-20-induced catalase counteracts accumulated hydrogen peroxide in the hair shaft. In some embodiments, the palmitoyl tetrapeptide-20 maintains hair shaft pigment. In some embodiments, the palmitoyl tetrapeptide-20 contributes to and enhances the beneficial hair care effects of the formulation of the disclosure.

In some embodiments, the formulation comprises palmitoyl tetrapeptide-20. In some embodiments, the palmitoyl tetrapeptide-20 is from about 1% to about 4% weight/weight (W/W) of the formulation of the disclosure. In some embodiments, palmitoyl tetrapeptide-20 is at least 1%, 1.2%, 1.4%, 1.6%, 1.8%, or 2% W/W of the formulation of the disclosure. In some embodiments, palmitoyl tetrapeptide-20 is at least 2.2%, 2.4%, 2.6%, 2.8%, or 3% W/W of the formulation of the disclosure. In some embodiments, the palmitoyl tetrapeptide-20 is at least 3.2%, 3.4%, 3.6%, 3.8%, or 4% W/W of the formulation of the disclosure.

III. Primary Extracts of the Formulation

The disclosure provides for various extracts that individually and in combination are thought to confer beneficial hair care effects. Each extract is non-synthetically produced, e.g., derived from the plant, and is formulated to have a surprising additive and/or synergistic effect with other components of the disclosure. In some embodiments, the effectiveness of another component, e.g., palmitoyl tetrapeptide-20 peptide, may be increased by the combination of extracts provided herein, by improving the penetration of the component through skin to access the hair follicle in the reticular dermis layer and reduce inflammation of the epidermis. Further, the extracts provided herein are natural and, in some cases, organic, and are designed to stimulate overall hair health, and to thicken and strengthen hair shafts.

In some embodiments, the extracts provided herein are designed to treat hair follicle pigment loss by increasing the effectiveness and delivery of palmitoyl tetrapeptide-20 peptide, which reduces melanocyte death in hair follicles associated with reactive oxygen species (ROS).

Formulation of extracts of any of *Zanthoxylum bungeanum, Humulus lupulus, Sesamum indicum* seed, *Panax ginseng* root, or *Polygonum multiflorum* in water may be challenging to produce. For example, *Polygonum multiflorum* does not solubilize easily in water, and affects the pH and color of a water-based formulation. However, formulations of appropriate color are often desired for hair treatments, and an undesirable pH of a topical hair treatment formulation will affect the user's tolerance and may cause inflammation. Therefore, as provided herein, formulations and extracts comprising *Polygonum multiflorum* may be designed to optimize the solubility, color, and/or pH. Further, formulations and extracts comprising any of *Zanthoxylum bungeanum, Humulus lupulus, Sesamum indicum* seed, *Panax ginseng* root, or *Polygonum multiflorum*, may exhibit a prohibitive odor, in particular formulations and extracts comprising *Humulus lupulus*. The formulations and extracts provided herein may be designed to improve the odor without necessarily masking the odor with fragrance.

In some embodiments, the extract comprises a *Zanthoxylum bungeanum* fruit extract. In the formulations disclosed herein, an extract comprising *Zanthoxylum bungeanum* fruit is applied in the serum topically to confer at least one beneficial hair care effect. In some embodiments, the *Zanthoxylum bungeanum* fruit extract is used as a lifting agent that relaxes subcutaneous muscles. In some embodiments, the *Zanthoxylum bungeanum* fruit extract is applied topically to the scalp. In some embodiments, the *Zanthoxylum bungeanum* fruit extract is applied to any surface wherein a beneficial hair care effect is desired. In some embodiments, the relaxing of subcutaneous muscles improves penetration of the formulation of the disclosure into the scalp. In some embodiments, the *Zanthoxylum bungeanum* fruit extract works in synergy with the other ingredients of the formulation to improve penetration of the formulation in the layers of the skin surrounding the hair follicle. In some embodiments, the *Zanthoxylum bungeanum* fruit extract improves penetration of the formulation of the disclosure to the hair follicles and enhances the beneficial hair care effects of the formulation of the disclosure.

In some embodiments, the extract comprising *Zanthoxylum bungeanum* fruit is about 0.5% to about 2.5% W/W of the formulation of the disclosure. In some embodiments, the *Zanthoxylum bungeanum* fruit extract is at least 0.5%, 0.6%, 0.7%, 0.8%, 0.9%, or 1% W/W of the formulation of the disclosure. In some embodiments, the *Zanthoxylum bungeanum* fruit extract is at least 1.1%, 1.2%, 1.3%, 1.4%, or 1.5% W/W of the formulation of the disclosure. In some embodiments, the *Zanthoxylum bungeanum* fruit extract is at least 1.6%, 1.7%, 1.8%, 1.9%, or 2% W/W of the formulation of the disclosure. In some embodiments, the *Zanthoxylum bungeanum* fruit extract is at least 2.1%, 2.2%, 2.3%, 2.4%, or 2.5% W/W of the formulation of the disclosure.

In some embodiments, the extract comprises *Humulus lupulus*. In some embodiments, the extract comprising *Humulus lupulus* is used as an antimicrobial agent for the formulation of the disclosure. In some embodiments, the *Humulus lupulus* extract aids in eliminating harmful bacteria from the skin surface that can cause acne or body odor. In some embodiments, the *Humulus lupulus* extract is an anti-inflammatory agent that helps reduce hair fall. In some embodiments, the *Humulus lupulus* extract promotes hair growth by inhibiting the activity of 5α-reductase, a naturally occurring molecule that contributes to hair loss. In some embodiments, the extract comprising *Humulus lupulus* enhances the hair growth and other beneficial aspects conferred by the formulation of the disclosure.

In some embodiments, the extract comprising *Humulus lupulus* is about 0.5% to about 2.5% W/W of the formulation of the disclosure. In some embodiments, the *Humulus lupu-*

*lus* extract is at least 0.5%, 0.6%, 0.7%, 0.8%, 0.9%, or 1% W/W of the formulation of the disclosure. In some embodiments, the *Humulus lupulus* extract is at least 1.1%, 1.2%, 1.3%, 1.4%, or 1.5% W/W of the formulation of the disclosure. In some embodiments, the extract comprising *Humulus lupulus* is at least 1.6%, 1.7%, 1.8%, 1.9%, or 2% W/W of the formulation of the disclosure. In some embodiments, the extract comprising *Humulus lupulus* is at least 2.1%, 2.2%, 2.3%, 2.4%, or 2.5% W/W of the formulation of the disclosure.

In some embodiments, the extract comprises *Sesamum indicum*. In some embodiments, the extract comprising *Sesamum indicum* seed is applied topically to confer at least one beneficial hair care effect. In some embodiments, the *Sesamum indicum* seed extract of the formulation of the disclosure is applied topically. In some embodiments, the *Sesamum indicum* seed extract improves blood circulation. In some embodiments, the *Sesamum indicum* seed extract improves hair growth by increasing blood supply to hair follicles. In some embodiments, the *Sesamum indicum* seed extract is an important source of phytonutrients such as omega-6 fatty acids, flavonoid phenolic antioxidants, vitamins, and dietary fiber with potential anti-cancer properties. In some embodiments, the *Sesamum indicum* seed extract has antimicrobial properties. In some embodiments, the *Sesamum indicum* seed extract contains vitamin E, vitamin B, and vitamin A, which helps nourish and rejuvenate skin. In some embodiments, the collective beneficial properties of the *Sesamum indicum* seed extract contributes to and enhances the beneficial hair care effects conferred by the formulation of the disclosure.

In some embodiments, the extract comprising *Sesamum indicum* seed is 0.5% to 2.5% W/W of the formulation of the disclosure. In some embodiments, the *Sesamum indicum* seed extract is at least 0.5%, 0.6%, 0.7%, 0.8%, 0.9%, or 1% W/W of the formulation of the disclosure. In some embodiments, the *Sesamum indicum* seed extract is at least 1.1%, 1.2%, 1.3%, 1.4%, or 1.5% W/W of the formulation of the disclosure. In some embodiments, the *Sesamum indicum* seed extract is at least 1.6%, 1.7%, 1.8%, 1.9%, or 2% W/W of the formulation of the disclosure. In some embodiments, the *Sesamum indicum* seed extract is at least 2.1%, 2.2%, 2.3%, 2.4%, or 2.5% W/W of the formulation of the disclosure.

In some embodiments, the extract comprises *Panax ginseng* root. In some embodiments, the *Panax ginseng* root extract is applied topically to confer at least one beneficial hair care effect. In some embodiments, the *Panax ginseng* root extract of the formulation of the disclosure is used to promote hair growth. In some embodiments, the *Panax ginseng* root extract promotes proliferation of hair follicles. In some embodiments, the *Panax ginseng* root extract increases hair density by increasing the number of hair follicles and hair shafts that grow from them. In some embodiments, the *Panax ginseng* root extract contributes to and enhances the beneficial hair care properties conferred by the formulation of the disclosure.

In some embodiments, the extract comprising *Panax ginseng* root is about 0.1% to about 1% W/W of the formulation of the disclosure. In some embodiments, the *Panax ginseng* root extract is at least 0.1%, 0.2%, 0.3%, 0.4%, 0.5%, or 0.6% W/W of the formulation of the disclosure. In some embodiments, the *Panax ginseng* root extract is at least 0.6%, 0.7%, 0.8%, 0.9%, or 1% W/W of the formulation of the disclosure.

In some embodiments, the extract comprises a *Polygonum multiflorum* extract. In some embodiments, the *Polygonum multiflorum* extract is applied topically to confer at least one beneficial hair care effect. In some embodiments, the *Polygonum multiflorum* extract of the disclosure is used as an antioxidant. In some embodiments, reactive oxygen species such as hydrogen peroxide accumulate in hair follicles as an individual ages. In some embodiments, the accumulation of hydrogen peroxide bleaches the pigmentation from hair shafts. In some embodiments, the accumulation of hydrogen peroxide contributes to loss of follicular stem cells and diminishes the health of hair follicles. In some embodiments, the *Polygonum multiflorum* extract acts as an antioxidant that counteracts the effects of hydrogen peroxide. In some embodiments, the *Polygonum multiflorum* extract improves the health of hair follicles and follicular stem cells. In some embodiments, the *Polygonum multiflorum* extract prevents the depigmentation of hair shafts by hydrogen peroxide. In some embodiments, the *Polygonum multiflorum* extract maintains healthy hair growth and robust hair shaft pigmentation. In some embodiments, the *Polygonum multiflorum* extract contributes to and enhances the beneficial hair care properties conferred by the formulation of the disclosure.

In some embodiments, the *Polygonum multiflorum* extract is an 8% extract. A number of other concentrations were tested, with an 8% extract demonstrating improved solubility and aroma compared to *Polygonum multiflorum* in glycerin or *Polygonum multiflorum* in different concentrations. In some embodiments, the *Polygonum multiflorum* 8% extract is about 0.05% to 0.2% W/W of the formulation of the disclosure. In some embodiments, the *Polygonum multiflorum* 8% extract is about 0.05%. 0.06%, 0.07%, 0.08%, 0.09%, or 0.1% W/W of the formulation of the disclosure. In some embodiments, the *Polygonum multiflorum* 8% extract is about 0.11%, 0.12%, 0.13%, 0.14%, or 0.15% W/W of the formulation of the disclosure. In some embodiments, the *Polygonum multiflorum* 8% extract is about 0.16%, 0.17%, 0.18%, 0.19%, or 0.2% W/W of the formulation of the disclosure.

In some embodiments, the formulations comprise *Ononis spinosa* root extract and/or *Avena strigosa* seed extract, e.g., as a formulation of Agreynist®. Illustrious formulations comprising *Ononis spinosa* root extract and *Avena strigosa* seed extract have been shown to improve repigmentation and improve the structural quality of the hair.

IV. Conditioning Agents of the Formulation

In some embodiments, it may be beneficial to add conditioning agents to the formulation of the disclosure. In some embodiments, the conditioning agents are added to a serum-based formulation of the disclosure. The conditioning agents described herein may confer various hair care benefits. The conditioning agents described herein may also serve to prime and condition the scalp and hair to further improve the beneficial effects conferred by the formulation of the disclosure. Effects of the condition agents described herein are also applicable to any skin surface wherein the beneficial hair care effects are desired.

In some embodiments, the conditioning agent is *Wasabia japonica* leaf extract. In the formulation of the disclosure, the *Wasabia japonica* leaf extract is applied topically to confer at least one beneficial hair care effect. In some embodiments, the *Wasabia japonica* leaf extract of the disclosure is derived from the leaves of the Wasabi plant. In some embodiments, the *Wasabia japonica* leaf extract comprises Wasabi flavones. In some embodiments, the *Wasabia japonica* leaf extract is applied topically. In some embodiments, the *Wasabia japonica* leaf extract confers at least one beneficial effect to hair follicles and the surrounding skin. In some embodiments, the *Wasabia japonica* leaf extract conditions the scalp so as to stimulate hair follicle growth. In some embodiments, the *Wasabia japonica* leaf extract contributes to and enhances the beneficial hair care properties conferred by the formulation of the disclosure.

In some embodiments, the *Wasabia japonica* leaf extract is 0.5% to 2.5% W/W of the formulation of the disclosure. In some embodiments, the *Wasabia japonica* leaf extract is at least 0.5%, 0.6%, 0.7%, 0.8%, 0.9%, or 1% W/W of the formulation of the disclosure. In some embodiments, the *Wasabia japonica* leaf extract is at least 1.1%, 1.2%, 1.3%, 1.4%, or 1.5% W/W of the formulation of the disclosure. In some embodiments, the *Wasabia japonica* leaf extract is at least 1.6%, 1.7%, 1.8%, 1.9%, or 2% W/W of the formulation of the disclosure. In some embodiments, the *Wasabia japonica* leaf extract is at least 2.1%, 2.2%, 2.3%, 2.4%, or 2.5% W/W of the formulation of the disclosure.

In some embodiments, the conditioning agent is *Glycine soja* germ extract. In the formulation of the disclosure, the *Glycine soja* germ extract is applied topically to confer at least one beneficial hair care effect. In some embodiments, the *Glycine soja* germ extract of the disclosure is used as a conditioning agent. In some embodiments, the *Glycine soja* germ extract comprises soyamine. In some embodiments, the *Glycine soja* germ extract conditions the scalp by boosting collagen synthesis. In some embodiments, the *Glycine soja* germ extract of the disclosure is used as a hair regrowth agent. In some embodiments, the *Glycine soja* germ extract stimulates follicular cell growth. In some embodiments, the *Glycine soja* germ extract stimulates hair growth. In some embodiments, the *Glycine soja* germ extract contributes to and enhances the beneficial hair care properties conferred by the formulation of the disclosure.

In some embodiments, the *Glycine soja* germ extract is 0.5% to 2.5% W/W of the formulation of the disclosure. In some embodiments, the *Glycine soja* germ extract is at least 0.5%, 0.6%, 0.7%, 0.8%, 0.9%, or 1% W/W of the formulation of the disclosure. In some embodiments, *Glycine soja* germ extract is at least 1.1%, 1.2%, 1.3%, 1.4%, or 1.5% W/W of the formulation of the disclosure. In some embodiments, the *Glycine soja* germ extract is at least 1.6%, 1.7%, 1.8%, 1.9%, or 2% W/W of the formulation of the disclosure. In some embodiments, the *Glycine soja* germ extract is at least 2.1%, 2.2%, 2.3%, 2.4%, or 2.5% W/W of the formulation of the disclosure.

In some embodiments, the conditioning agent is Chios mandarin extract. In the formulation of the disclosure, the Chios mandarin extract is applied topically to confer at least one beneficial hair care effect. In some embodiments, the Chios mandarin extract of the disclosure is used as a conditioning agent. In some embodiments, the Chios mandarin extract has antioxidant properties. In some embodiments, the Chios mandarin extract counteracts the accumulation of hydrogen peroxide in hair follicles. In some embodiments, the Chios mandarin extract prevents hair depigmentation caused by hydrogen peroxide bleaching. In some embodiments, the Chios mandarin extract induces melanin production in melanocytes. In some embodiments, the Chios mandarin extract induces melanocytes to inject melanin into hair shafts. In some embodiments, the Chios mandarin extract induces pigmentation in hair shafts. In some embodiments, the Chios mandarin extract induces pigmentation in hair. In some embodiments, the Chios mandarin extract maintains pigmentation in hair. In some embodiments, the Chios mandarin extract contributes to and enhances the beneficial hair care properties conferred by the formulation of the disclosure.

In some embodiments, the Chios mandarin extract is 0.5% to 2.5% W/W of the formulation of the disclosure. In some embodiments, the Chios mandarin extract is at least 0.5%, 0.6%, 0.7%, 0.8%, 0.9%, or 1% W/W of the formulation of the disclosure. In some embodiments, the Chios mandarin extract is at least 1.1%, 1.2%, 1.3%, 1.4%, or 1.5% W/W of the formulation of the disclosure. In some embodiments, the Chios mandarin extract is at least 1.6%, 1.7%, 1.8%, 1.9%, or 2% W/W of the formulation of the disclosure. In some embodiments, the Chios mandarin extract is at least 2.1%, 2.2%, 2.3%, 2.4%, or 2.5% W/W of the formulation of the disclosure.

In some embodiments, the conditioning agent is *Coffea arabica* seed extract. In the formulation of the disclosure, the *Coffea arabica* seed extract is applied topically to confer at least one beneficial hair care effect. In some embodiments, the *Coffea arabica* seed extract of the disclosure is used as a conditioning agent. In some embodiments, the *Coffea arabica* seed extract induces hair growth by stimulating hair follicles. In some embodiments, the *Coffea arabica* seed extract induces denser hair by simulating hair growth. In some embodiments, the *Coffea arabica* seed extract improves hair shaft structure. In some embodiments, the *Coffea arabica* seed extract confers more hair volume by improving hair shaft structure. In some embodiments, the *Coffea arabica* seed extract contributes to and enhances the beneficial hair care properties conferred by the formulation of the disclosure.

In some embodiments, the *Coffea arabica* seed extract is 0.005% to 0.05% W/W of the formulation of the disclosure. In some embodiments, the *Coffea arabica* seed extract is at least 0.005%, 0.006%, 0.007%, 0.008%, 0.009%, or 0.01% W/W of the formulation of the disclosure. In some embodiments, the *Coffea arabica* seed extract is at least 0.011%, 0.012%, 0.013%, 0.014%, or 0.015% W/W of the formulation of the disclosure. In some embodiments, the *Coffea arabica* seed extract is at least 0.016%, 0.017%, 0.018%, 0.019%, or 0.02% W/W of the formulation of the disclosure. In some embodiments, the *Coffea arabica* seed extract is at least 0.02%, 0.025%, 0.03%, 0.035%, 0.04%, 0.045% or 0.05% W/W of the formulation of the disclosure.

In some embodiments, the conditioning agent is caffeine. In the formulation of the disclosure, the caffeine is applied topically to confer at least one beneficial hair care effect. In some embodiments, the caffeine of the disclosure is used as a conditioning agent. In some embodiments, the caffeine is administered topically. In some embodiments, the caffeine is absorbed through the skin and into the hair follicles. In some embodiments, the caffeine suppresses the hair loss hormone dihydrotestosterone (DHT). In some embodiments, the caffeine stimulates hair growth. In some embodiments, the caffeine encourages elongation of the hair shaft. In some embodiments, the caffeine induces and maintains robust hair growth. In some embodiments, the caffeine induces and maintains hair volume. In some embodiments, the caffeine contributes to and enhances the beneficial hair care properties conferred by the formulation of the disclosure.

In some embodiments, the caffeine is derived from natural sources. In some embodiments, the caffeine is synthesized artificially. In some embodiments, the caffeine is 0.05% to 0.2% W/W of the formulation of the disclosure. In some embodiments, the caffeine is at least 0.05%, 0.06%, 0.07%, 0.08%, 0.09%, or 0.1% W/W of the formulation of the disclosure. In some embodiments, the caffeine is at least 0.11%, 0.12%, 0.13%, 0.14%, or 0.15% W/W of the formulation of the disclosure. In some embodiments, the caffeine is at least 0.16%, 0.17%, 0.18%, 0.19%, or 0.2% W/W of the formulation of the disclosure.

In some embodiments, the conditioning agent is panthenol. Panthenol is the alcohol analog of pantothenic acid, also known as vitamin B5. In the formulation of the disclosure, the panthenol is applied topically to confer at least one beneficial hair care effect. In some embodiments, the panthenol of the disclosure is topically applied to any skin surface in which the beneficial hair care effects of the disclosure is desired. In some embodiments, the panthenol of the disclosure is topically applied to the scalp. In some embodiments, the panthenol is a conditioning agent. In some embodiments, the panthenol primes the skin surface. In some embodiments, the panthenol draws moisture from deeper skin levels. In some embodiments, the panthenol draw moisture to the surface of the skin. In some embodiments, the panthenol draws moisture to the surface of the scalp. In some embodiments, the panthenol softens and smooths the skin. In some embodiments, the panthenol softens and smooths the scalp. In some embodiments, the panthenol expands the skin surface. In some embodiments, the panthenol expands the scalp surface. In some embodiments, the panthenol expands the skin surface to allow other topical agents to penetrate deeper into the skin surface. In some embodiments, the panthenol expands the scalp surface to allow other topical agents to penetrate deeper into the scalp. In some embodiments, the panthenol expands the skin surface to allow other topical agents to penetrate deeper into the skin. In some embodiments, the panthenol expands the skin surface to allow other topical agents to penetrate deeper into the scalp. In some embodiments, the panthenol expands the skin surface to allow other topical agents to penetrate deeper to the hair follicles. In some embodiments, the panthenol expands the scalp surface to allow other topical agents to penetrate deeper to the hair follicles. In some embodiments, the panthenol expands the skin surface to enhance the effects of other topical agents on hair follicles. In some embodiments, the panthenol expands the scalp surface to enhance the effects of other topical agents on hair follicles. In some embodiments, the panthenol contributes to and enhances the beneficial hair care properties conferred by the formulation of the disclosure.

In some embodiments, the panthenol enhances the activity of the formulation of the disclosure. In some embodiments, the panthenol stabilizes the pH of the formulation. In some embodiments, the panthenol maintains the alkaline pH of the formulation. In some embodiments, the panthenol-induced alkaline pH aids in swelling the skin surface, which allows the ingredients of the formulation to penetrate deeper into the affected skin surface and hair follicles. In some embodiments, the panthenol conditions and moisturizes hair. Aging hair, including grey hair, typically suffers from moisture loss and becomes more brittle. In some embodiments, the panthenol conditions and moisturizes aging hair and grey hair, thus maintaining the strength of the hair shaft. In some embodiments, the panthenol of the formulation provides essential nutrients to the skin surface and the body. The panthenol of the formulation is a provitamin and is converted into vitamin B5 in the body. Vitamin B5 confers numerous health benefits such as synthesis of blood cells for nourishing the scalp and other skin surfaces. In some embodiments, the panthenol of the formulation is absorbed by the skin surface and is converted to vitamin B5 in the body, thus conferring certain health benefits. In some embodiments, the panthenol is used as the primary styling agent of the formulation. The amount and variety of styling agents typically used in topical cosmetics dilutes all the other ingredients and reduces their efficacy. On the other hand, the primary styling agent of the formulation is panthenol. In some embodiments, the use of panthenol as the primary styling agent reduces the dilution of the other active ingredients, and thus helps maximize the efficacy.

In some embodiments, the panthenol is 0.5% to 2.5% W/W of the formulation of the disclosure. In some embodiments, the panthenol is at least 0.5%, 0.6%, 0.7%, 0.8%, 0.9%, or 1% W/W of the formulation of the disclosure. In some embodiments, the panthenol is at least 1.1%, 1.2%, 1.3%, 1.4%, or 1.5% W/W of the formulation of the disclosure. In some embodiments, the panthenol is at least 1.6%, 1.7%, 1.8%, 1.9%, or 2% W/W of the formulation of the disclosure. In some embodiments, the panthenol is at least 2.1%, 2.2%, 2.3%, 2.4%, or 2.5% W/W of the formulation of the disclosure.

In some embodiments, the conditioning agent is biotin. Biotin, also known as vitamin B7, is involved in a wide range of metabolic processes. In some embodiments, the biotin of the disclosure is used as a conditioning agent. In some embodiments, the biotin of the disclosure is applied topically. In some embodiments, the biotin of the disclosure improves the protective protein structure of hair follicles. In some embodiments, the biotin of the disclosure protects the protein structure of keratin. In some embodiments, the biotin of the disclosure protects the protein structure of hair shafts. In some embodiments, the biotin of the disclosure delays hair shaft depigmentation. In some embodiments, the biotin of the disclosure delays hair depigmentation. In some embodiments, the biotin of the disclosure contributes to and enhances the beneficial hair care properties conferred by the formulation of the disclosure.

In some embodiments, the biotin is 0.01% to 0.15% W/W of the formulation of the disclosure. In some embodiments, the biotin is at least 0.01%, 0.02%, 0.03%, 0.04%, 0.05%, or 0.06% W/W of the formulation of the disclosure. In some embodiments, the biotin is at least 0.07%, 0.08%, 0.09%, or 0.1% W/W of the formulation of the disclosure. In some embodiments, the biotin is at least 0.11%, 0.12%, 0.13%, 0.14%, or 0.15% W/W of the formulation of the disclosure.

In some embodiments, the conditioning agent comprises various compounds used to further moisturize and condition any skin surface in which the beneficial hair care effects of the disclosure is desired. In some embodiments, the conditioning agent comprises various compounds typically used to further moisturize and condition the scalp. In some embodiments, the conditioning agent is 1,2-hexanediol. In some embodiments, the conditioning agent is caprylyl glycol. In some embodiments, the conditioning agent is hydrolyzed barley protein. In some embodiments, the conditioning agent is amodimethicone. In some embodiments, the conditioning agent is guar hydroxypropyltrimonium chloride.

In some embodiments, the 1,2-hexanediol of the disclosure is part of the formulation of the disclosure. In some embodiments, the 1,2-hexanediol is 0.5% to 2.5% W/W of the formulation of the disclosure. In some embodiments, the 1,2-hexanediol is at least 0.5%, 0.6%, 0.7%, 0.8%, 0.9%, or 1% W/W of the formulation of the disclosure. In some embodiments, the 1,2-hexanediol is at least 1.1%, 1.2%, 1.3%, 1.4%, or 1.5% W/W of the formulation of the disclosure. In some embodiments, the 1,2-hexanediol is at least 1.6%, 1.7%, 1.8%, 1.9%, or 2% W/W of the formulation of the disclosure. In some embodiments, the 1,2-hexanediol is at least 2.1%, 2.2%, 2.3%, 2.4%, or 2.5% W/W of the formulation of the disclosure.

In some embodiments, the caprylyl glycol of the disclosure is part of the formulation of the disclosure. In some embodiments, the caprylyl glycol is 0.5% to 2.5% W/W of the formulation of the disclosure. In some embodiments, the caprylyl glycol is at least 0.5%, 0.6%, 0.7%, 0.8%, 0.9%, or 1% W/W of the formulation of the disclosure. In some embodiments, the caprylyl glycol is at least 1.1%, 1.2%, 1.3%, 1.4%, or 1.5% W/W of the formulation of the disclosure. In some embodiments, the caprylyl glycol is at least 1.6%, 1.7%, 1.8%, 1.9%, or 2% W/W of the formulation of the disclosure. In some embodiments, the caprylyl glycol is at least 2.1%, 2.2%, 2.3%, 2.4%, or 2.5% W/W of the formulation of the disclosure.

In some embodiments, the hydrolyzed barley protein of the disclosure is part of the formulation of the disclosure. In some embodiments, the hydrolyzed barley protein is 0.5% to 2.5% W/W of the formulation of the disclosure. In some embodiments, the hydrolyzed barley protein is at least 0.5%, 0.6%, 0.7%, 0.8%, 0.9%, or 1% W/W of the formulation of the disclosure. In some embodiments, the hydrolyzed barley protein is at least 1.1%, 1.2%, 1.3%, 1.4%, or 1.5% W/W of the formulation of the disclosure. In some embodiments, the hydrolyzed barley protein is at least 1.6%, 1.7%, 1.8%, 1.9%, or 2% W/W of the formulation of the disclosure. In some embodiments, the hydrolyzed barley protein is at least 2.1%, 2.2%, 2.3%, 2.4%, or 2.5% W/W of the formulation of the disclosure.

In some embodiments, the amodimethicone is part of the formulation of the disclosure. In some embodiments, the amodimethicone is 0.1% to 1% W/W of the formulation of the disclosure. In some embodiments, the amodimethicone is at least 0.1%, 0.2%, 0.3%, 0.4%, 0.5%, or 0.6% W/W of the formulation of the disclosure. In some embodiments, the amodimethicone is at least 0.6%, 0.7%, 0.8%, 0.9%, or 1% W/W of the formulation of the disclosure.

In some embodiments, the guar hydroxypropyltrimonium chloride of the disclosure is part of the formulation of the disclosure. In some embodiments, the guar hydroxypropyltrimonium chloride is 0.05% to 0.2% W/W of the formulation of the disclosure. In some embodiments, the guar hydroxypropyltrimonium chloride is at least 0.05%, 0.06%, 0.07%, 0.08%, 0.09%, or 0.1% W/W of the formulation of the disclosure. In some embodiments, the guar hydroxypropyltrimonium chloride is at least 0.11%, 0.12%, 0.13%, 0.14%, or 0.15% W/W of the formulation of the disclosure. In some embodiments, the guar hydroxypropyltrimonium chloride is at least 0.16%, 0.17%, 0.18%, 0.19%, or 0.2% W/W of the formulation of the disclosure.

V. Excipients of the Formulation

The formulation of the disclosure may require the addition of various excipients for long term stabilization, as bulking agents, and/or to confer a therapeutic enhancement on the active ingredient or ingredients of the formulation. In some embodiments, the formulation of the disclosure contains excipients selected from the group consisting of glycerin, butylene glycol, hydroxyethylcellulose, and cocamidopropyl betaine, cetyl esters, cetyl alcohol, stearyl alcohol and combinations thereof.

In some embodiments, the glycerin is part of the formulation of the disclosure. In some embodiments, the glycerin is 1% to 4% W/W of the formulation of the disclosure. In some embodiments, the glycerin is at least 1%, 1.2%, 1.4%, 1.6%, 1.8%, or 2% W/W of the formulation of the disclosure. In some embodiments, the glycerin is at least 2.2%, 2.4%, 2.6%, 2.8%, or 3% W/W of the formulation of the disclosure. In some embodiments, the glycerin is at least 3.2%, 3.4%, 3.6%, 3.8%, or 4% W/W of the formulation of the disclosure.

In some embodiments, the butylene glycol of the disclosure is part of the formulation of the disclosure. In some embodiments, the butylene glycol is 0.5% to 2.5% W/W of the formulation of the disclosure. In some embodiments, the butylene glycol is at least 0.5%, 0.6%, 0.7%, 0.8%, 0.9%, or 1% W/W of the formulation of the disclosure. In some embodiments, the butylene glycol is at least 1.1%, 1.2%, 1.3%, 1.4%, or 1.5% W/W of the formulation of the disclosure. In some embodiments, the butylene glycol is at least 1.6%, 1.7%, 1.8%, 1.9%, or 2% W/W of the formulation of the disclosure. In some embodiments, the butylene glycol is at least 2.1%, 2.2%, 2.3%, 2.4%, or 2.5% W/W of the formulation of the disclosure.

In some embodiments, the hydroxyethylcellulose is part of the formulation of the disclosure. In some embodiments, the hydroxyethylcellulose is 0.1% to 1% W/W of the formulation of the disclosure. In some embodiments, the hydroxyethylcellulose is at least 0.1%, 0.2%, 0.3%, 0.4%, 0.5%, or 0.6% W/W of the formulation of the disclosure. In some embodiments, the hydroxyethylcellulose is at least 0.6%, 0.7%, 0.8%, 0.9%, or 1% W/W of the formulation of the disclosure.

In some embodiments the cocamidopropyl betaine is part of the formulation of the disclosure. In some embodiments the cocamidopropyl betaine is 15% to 40% W/W of the formulation of the disclosure. In some embodiments the cocamidopropyl betaine is 15%, 16%, 17%, 18%, 19%, or 20% W/W of the formulation of the disclosure. In some embodiments the cocamidopropyl betaine is 21%, 22%, 23%, 24%, 25%, or 26% W/W of the formulation of the disclosure. In some embodiments the cocamidopropyl betaine is 27%, 28%, 29%, 30%, 31%, or 32% W/W of the formulation of the disclosure. In some embodiments the cocamidopropyl betaine is 33%, 34%, 35%, 36%, 37%, 38%, 39%, or 40% W/W of the formulation of the disclosure.

In some embodiments, the cetyl esters is part of the formulation of the disclosure. In some embodiments, the cetyl esters is 1.5% to 3.5% W/W of the formulation of the disclosure. In some embodiments, the cetyl esters is 1.5%, 1.8%, 2%, 2.5%, 2.8%, 3.2%, or 3.5% W/W of the formulation of the disclosure.

In some embodiments, the cetyl alcohol is part of the formulation of the disclosure. In some embodiments, the cetyl alcohol is 1.5% to 3.5% W/W of the formulation of the disclosure. In some embodiments, the cetyl alcohol is 1.5%, 1.8%, 2%, 2.5%, 2.8%, 3.2%, or 3.5% W/W of the formulation of the disclosure.

In some embodiments, the stearyl alcohol is part of the formulation of the disclosure. In some embodiments, the stearyl alcohol is 1.5% to 3.5% W/W of the formulation of the disclosure. In some embodiments, the stearyl alcohol is 1.5%, 1.8%, 2%, 2.5%, 2.8%, 3.2%, or 3.5% W/W of the formulation of the disclosure.

In an exemplary embodiment, when Palmitoyl Tetrapeptide-20 Amide in glycerin and water is used, it may be 1% to 4% of the formulation of the disclosure. When *Polygonum multiflorum* 8% root extract is used, it may be 0.05% to 0.2% of the formulation of the disclosure. When *Zanthoxylum bungeanum* fruit extract in glycerin and water is used, it may be 0.5% to 2.5% of the formulation of the disclosure. When *Humulus lupulus* extract in glycerin and water is used, it may be 0.5% to 2.5% of the formulation of the disclosure. When *Sesamum indicum* seed extract in glycerin and water is used, it may be 0.5% to 2.5% of the formulation of the disclosure. When *Glycine soja* germ extract in butylene glycol and water is used, it may be 0.5% to 2.5% of the formulation of the disclosure. When hydrolyzed barley protein is used, it may be 0.5% to 2.5% of the formulation of the disclosure. When 1,2-Hexanediol in caprylyl glycol is used, it may be 0.5% to 2.5% of the formulation of the disclosure. When *Wasabia japonica* leaf extract in butylene glycol is used, it may be 0.5% to 2.5% of the formulation of the disclosure. When *Panax Ginseng* root extract in glycerin is used, it may be 0.1% to 1% of the formulation of the disclosure. When caffeine is used, it may be 0.05% to 0.2% of the formulation of the disclosure. When biotin is used, it may be 0.01% to 0.15% of the formulation of the disclosure. When *Coffea arabica* seed extract is used, it may be 0.005% to 0.05% of the formulation of the disclosure. When hydroxyethylcellulose is used, it may be 0.1% to 1% of the formulation of the disclosure.

VI. Methods of Manufacturing Serum-Based Formulations

In an exemplary embodiment, when Palmitoyl Tetrapeptide-20 Amide in glycerin and water is used, it may be 2% of the serum formulation of the disclosure. When *Polygonum multiflorum* 8% root extract is used, it may be 0.1% of the serum formulation of the disclosure. When *Zanthoxylum bungeanum* fruit extract in glycerin and water is used, it may be 1.5% of the serum formulation of the disclosure. When *Humulus lupulus* extract in glycerin and water is used, it may be 1.5% of the serum formulation of the disclosure. When *Sesamum indicum* seed extract in glycerin and water is used, it may comprise 1.2% of the serum formulation of the disclosure. When *Glycine soja* germ extract in butylene glycol and water is used, it may be 1% of the serum formulation of the disclosure. When hydrolyzed barley protein is used, it may be 1% of the serum formulation of the disclosure. When 1,2-Hexanediol in caprylyl glycol is used, it may be 1% of the serum formulation of the disclosure. When *Wasabia japonica* leaf extract in butylene glycol is used, it may be 1% of the serum formulation of the disclosure. When *Panax Ginseng* root extract in glycerin is used, it may be 0.5% of the serum formulation of the disclosure. When caffeine is used, it may be 0.1% of the serum formulation of the disclosure. When biotin is used, it may be 0.05% of the serum formulation of the disclosure. When *Coffea arabica* seed extract is used, it may be 0.01% of the serum formulation of the disclosure. When hydroxyethylcellulose is used, it may be 0.3% of the serum formulation of the disclosure.

Water is added in the quantity sufficient to make (QSAD) the formulations, i.e., the remainder of the W/W percentage.

TABLE 1A

Components of an example Serum-based Formulation

| Serum-based Formulation Component | % W/W |
|---|---|
| Palmitoyl Tetrapeptide-20 Amide in glycerin and water | 2% |
| *Polygonum multiflorum* 8% root extract | 0.1% |
| *Zanthoxylum bungeanum* fruit extract in glycerin and water | 1.5% |
| *Humulus lupulus* extract in glycerin and water | 1.5% |
| *Sesamum indicum* seed extract in glycerin and water | 1.2% |
| *Glycine soja* germ extract in butylene glycol and water | 1% |
| Hydrolyzed barley protein | 1% |
| 1,2-Hexanediol in caprylyl glycol | 1% |
| *Wasabia japonica* leaf extract in butylene glycol | 1% |
| *Panax* Ginseng root extract in glycerin | 0.5% |
| Caffeine | 0.1% |
| Biotin | 0.05% |
| *Coffea arabica* seed extract | 0.01% |
| Hydroxyethylcellulose | 0.3% |
| Water | QSAD |

TABLE 1B

Components of an example Serum-based Formulation

| Serum-based Formulation Component | % W/W |
|---|---|
| Glycerin and Water and Palmitoyl Tetrapeptide 20 Amide (Greyverse) | 2 |
| *Citrus Reticulata* (Tangerine) Extract and Acetyl Tyrosine and Pentylene Glycol and Gluconolactone and Sodium Benzoate and Water | 2 |
| Water and Glycerin and *Xanthoxylum Bungeanum* Fruit Extract | 1.5 |
| Glycerin and Water and *Humulus Lupulus* (Hops) Extract | 1.5 |
| Glycerin and Water and *Sesamum Indicum* Seed Extract | 1.2 |
| Soybean Germ Extract and Water and Butylene Glycol | 1 |
| Hydrolyzed Barley Protein | 1 |
| 1,2-Hexanediol and Caprylyl Glycol | 1 |
| Butylene Glycol and *Wasabia Japonica* Leaf Extract | 1 |
| Glycerin and *Panax Ginseng* Root Extract | 0.5 |
| Hydroxyethylcellulose | 0.5 |
| Caffeine | 0.1 |
| *Polygonum multiflorum* 8% extract | 0.1 |
| Biotin | 0.05 |
| *Coffea Arabica* (Coffee) Seed Extract | 0.01 |
| Water | QSAD |

In the embodiments provided herein, the serum-based formulation is manufactured to optimize product consistency and active ingredient delivery upon administration. In the embodiments provided herein, components of the serum-based formulation are combined in a stepwise protocol. In the embodiments provided herein, each component is designated as a specific phase of the manufacturing protocol. In the embodiments provided herein, phase A consists of water and hydroxyethylcellulose. In the embodiments provided herein, phase B consists of *Polygonum multiflorum* 8% root extract. In the embodiments provided herein, phase C consists of *Zanthoxylum bungeanum* fruit extract in glycerin and water, *Humulus lupulus* extract in glycerin and water, *Sesamum indicum* seed extract in glycerin and water, *Glycine soja* germ extract in butylene glycol and water, hydrolyzed barley protein, 1,2-Hexanediol in caprylyl glycol, *Wasabia japonica* leaf extract in butylene glycol, *Panax Ginseng* root extract in glycerin, caffeine, biotin, and *Coffea arabica* seed extract. In the embodiments provided herein, phase D consists of Palmitoyl Tetrapeptide-20 Amide in glycerin and water.

In the embodiments provided herein, phase A of the serum-based formulation is added to 60° C. water and mixed until a gel is formed. In the embodiments provided herein, phase B is added after phase A to the serum-based formulation slowly, mixing until fully dissolved. In the embodiments provided herein, phase C is added after phase B to the serum-based formulation, mixing until uniform. In the embodiments provided herein, the temperature of the serum-based formulation is lowered to below 45° C. after adding phase C. In the embodiments provided herein, phase D is added after phase C to the serum-based formulation when the temperature is below 45° C., mixing until uniform. In the embodiments provided herein, the formulation is mixed and assayed for quality. In the embodiments provided herein, the pH of the formulation at every step of the manufacturing procedure is maintained above a pH of 6, to maintain consistency, color, and efficacy of the formulation.

VII. Shampoo-Based Formulations

In some embodiments, the formulations of the disclosure are shampoo-based. A shampoo-based formulation may be helpful for delivering the active ingredients of the formulation directly to the hair strands and hair follicles as the hair is being cleansed. In some embodiments, the shampoo-based formulation may comprise some or all of the ingredients of the serum-based formulation described above, and further comprise a cleanser, a surfactant, a preservative, and/or a fragrance. For example, a shampoo-based formulation may comprise a palmitoyl tetrapeptide-20; an extract selected from the group consisting of *Zanthoxylum bungeanum* fruit extract, *Humulus lupulus* extract, *Sesamum indicum* seed extract, *Panax ginseng* root extract, *Polygonum multiflorum* 8% root extract, and combinations thereof; a cleanser, a surfactant, a preservative, and/or a fragrance. In some embodiments, a shampoo-based formulation is rinsed off with water. In other embodiments, a shampoo-based formulation is left on the hair, e.g., as a dry shampoo.

The shampoo-based formulations are designed to confer at least one beneficial hair care effect as described above. In many instances, the shampoo-based formulations disclosed herein produce a surprising additive and/or synergistic on hair health, with effects including but not limited to: ameliorating depigmentation, inducing pigmentation, promoting pigmentation, maintaining pigmentation, thickening hair shafts, strengthening hair shafts, increasing the density of the hair, increasing the volume of the hair, increasing the volume of the hair, and combinations thereof.

In some embodiments, the shampoo-based formulations provided herein are designed to treat hair follicle pigment loss by increasing the effectiveness and delivery of palmitoyl tetrapeptide-20 peptide, which reduces melanocyte death in hair follicles associated with reactive oxygen species (ROS). In some embodiments, the effectiveness of the peptide may be increased by: improving the penetration of the peptide through skin to access the reticular dermis layer; reducing inflammation of the epidermis; or facilitating use by the subject and increasing effectiveness of the product in the form of appropriate viscosity, odor, solubilization, and/or pH. Further, the shampoo-based formulations provided herein are substantially made of natural and organic ingredients, and are designed to stimulate overall hair health, and to thicken and strengthen hair shafts.

In some embodiments, shampoo formulations of the disclosure are water-based. In some embodiments, water-based shampoo formulations provide improved penetration of a treatment through skin and also reduce inflammation of the epidermis relative to comparable oil-based or emulsion-based shampoo formulations. In some embodiments, water-based shampoo formulations provide an improved experience for a user, particularly for shampoo formulations used every day, or more than once a day.

In some embodiments, water-based shampoo formulations of the disclosure may be optimized to increase solubilization of one or more of *Zanthoxylum bungeanum, Humulus lupulus, Sesamum indicum* seed, *Panax ginseng* root, or *Polygonum multiflorum* extracts. In some embodiments, water-based shampoo formulations of the disclosure may be optimized to increase solubilization of an additional component, e.g., a peptide, e.g., palmitoyl tetrapeptide-20 peptide. In some embodiments, optimization of the water-based shampoo formulations may increase effectiveness, improve the pH of the formulation, improve the odor of the formulation, improve the color of the formulation, improve the viscosity of the formulation, improve the stability of the formulation, and/or improve the scaling of product production.

Formulation of extracts of any of *Zanthoxylum bungeanum, Humulus lupulus, Sesamum indicum* seed, *Panax ginseng* root, or *Polygonum multiflorum Polygonum multiflorum* in shampoo is also challenging. Surfactants and additives common in shampoos may limit absorption by the skin, and therefore the effectiveness of any of *Zanthoxylum bungeanum, Humulus lupulus, Sesamum indicum* seed, *Panax ginseng* root, and/or *Polygonum multiflorum* as a hair treatment. The shampoos of the instant disclosure were designed to both stabilize the extracts of *Zanthoxylum bungeanum, Humulus lupulus, Sesamum indicum* seed, *Panax ginseng* root, and/or *Polygonum multiflorum* in a water-based formulation, and also to permit absorption of the extracts. In some embodiments, the shampoos of the instant disclosure were designed to both stabilize and confer absorption of a peptide, e.g., palmitoyl tetrapeptide-20 peptide.

In some embodiments, the pH of the shampoo-based formulation is about 4.0-about 6.0. In some embodiments, the pH of the shampoo-based formulation is about 4.5-about 5.5. In some embodiments, the pH of the shampoo-based formulation is about 4.9. In some embodiments, the viscosity of the shampoo-based formulation is about 1000-5000 centipoise (cps), as measured at 25° C. on a low viscosity torque (LVT) viscometer at 12 rotations per minute. In some embodiments, the viscosity of the shampoo-based formulation is about 2500-3500 centipoise (cps). In some embodiments, the viscosity of the shampoo-based formulation is about 2900 centipoise (cps).

The shampoo-based formulation may comprise a cleanser helpful for removing dirt and excess oil from the hair, scalp, and the skin surface, thus allowing more efficient administration of the active ingredients of the formulation. In some embodiments, the cleansers of the formulation are chosen from the group consisting of sodium lauroyl methyl isethionate and citric acid. In some embodiments, the cleanser sodium lauroyl methyl isethionate is 3% to 9% W/W of the formulation of the disclosure. In some embodiments, the citric acid is 0.1% to 0.5% W/W of the formulation of the disclosure.

The shampoo-based formulation may comprise a surfactant useful for breaking down dirt and other impurities in the hair, skin, and scalp by functioning as a surface tension disrupting agent. In some embodiments, the surfactant of the disclosure is sodium cocoyl isethionate. In some embodiments, the sodium cocoyl isethionate is 1% to 4% W/W of the formulation of the disclosure.

The shampoo-based formulation may comprise a preservative useful for stabilizing the ingredients of the formulation and for preventing microbial contamination of the product. In some embodiments, the preservative of the disclosure is selected from the group consisting of sodium benzoate, potassium sorbate, ethylhexylglycerin, and combinations thereof. In some embodiments, the sodium benzoate is 0.05% to 0.5% W/W of the formulation of the disclosure. In some embodiments, the potassium sorbate is 0.05% to 0.5% W/W of the formulation of the disclosure. In some embodiments, the ethylhexylglycerin is 0.05% to 0.5% W/W of the formulation of the disclosure.

The shampoo-based formulation may comprise a fragrance helpful for enhancing the experience of the subject in need thereof as the shampoo-based formulation is being used. Fragrances derived from non-synthetic essential oils help provide a natural scent that minimizes irritation. In some embodiments, the non-synthetic fragrance of the disclosure is sage. In some embodiments, the non-synthetic fragrance of the disclosure is cedar. In some embodiments, the non-synthetic fragrances of the disclosure is a blend of sage and cedar. In some embodiments, the sage and cedar blend of non-synthetic fragrance is 0.5% to 1.5% W/W of the formulation of the disclosure.

In an exemplary shampoo-based formulation embodiment, when palmitoyl tetrapeptide-20 Amide in glycerin and water is used, it may be 1% to 4% of the formulation of the disclosure. When *Polygonum multiflorum* 8% root extract is used, it may be 0.0005% to 0.002% of the shampoo-based formulation of the disclosure. When *Zanthoxylum bungeanum* fruit extract in glycerin and water is used, it may be 0.0005% to 0.002% of the shampoo-based formulation of the disclosure. When *Humulus lupulus* extract in glycerin and water is used, it may be 0.0005% to 0.002% of the shampoo-based formulation of the disclosure. When *Sesamum indicum* seed extract in glycerin and water is used, it may be 0.0005% to 0.002% of the shampoo-based formulation of the disclosure. When *Glycine soja* germ extract in butylene glycol and water is used, it may be 0.0005% to 0.002% of the shampoo-based formulation of the disclosure. When hydrolyzed barley protein is used, it may be 0.05% to 0.2% of the shampoo-based formulation of the disclosure. When *Wasabia japonica* leaf extract in butylene glycol is used, it may be 0.0005% to 0.002% of the shampoo-based formulation of the disclosure. When *Panax Ginseng* root extract in glycerin is used, it may be 0.005% to 0.02% of the shampoo-based formulation of the disclosure. When caffeine is used, it may be 0.0005% to 0.002% of the shampoo-based formulation of the disclosure. When biotin is used, it may be 0.0005% to 0.002% of the shampoo-based formulation of the disclosure. When *Coffea arabica* seed extract is used, it may be 0.005% to 0.02% of the shampoo-based formulation of the disclosure. When sodium lauroyl methyl isethionate is used, it may be 3% to 9% of the shampoo-based formulation of the disclosure. When citric acid is used, it may be 0.1% to 0.5% of the shampoo-based formulation of the disclosure. When sodium cocoyl isethionate is used, it may be 1% to 4% of the shampoo-based formulation of the disclosure. When sodium benzoate is used, it may be 0.05% to 0.5% of the shampoo-based formulation of the disclosure. When potassium sorbate is used, it may be 0.05% to 0.5% of the shampoo-based formulation of the disclosure. When ethylhexylglycerin is used, it may be 0.05% to 0.5% of the shampoo-based formulation of the disclosure. When guar hydroxypropyltrimonium chloride is used, it may be 0.05% to 0.2% of the shampoo-based formulation of the disclosure. When glycerin is used, it may be 0.5% to 2% of the shampoo-based formulation of the disclosure. When panthenol is used, it may be 0.5 to 2% of the shampoo-based formulation of the disclosure. When cocamidopropyl betaine is used, it may be 20% to 40% of the shampoo-based formulation. When amodimethicone is used, it may be 0.1% to 1% of the shampoo-based formulation of the disclosure. When fragrance is used, it may be 0.5% to 1.5% of the shampoo-based formulation of the disclosure.

VIII. Methods of Manufacturing Shampoo-Based Formulations

In an exemplary embodiment, when Palmitoyl Tetrapeptide-20 Amide in glycerin and water is used, it may be 2% of the shampoo-based formulation of the disclosure. When *Polygonum multiflorum* 8% root extract is used, it may be 0.001% of the shampoo-based formulation of the disclosure. When *Zanthoxylum bungeanum* fruit extract in glycerin and water is used, it may be 0.001% of the shampoo-based formulation of the disclosure. When *Humulus lupulus* extract in glycerin and water is used, it may be 0.001% of the shampoo-based formulation of the disclosure. When *Sesamum indicum* seed extract in glycerin and water is used, it may be 0.001% of the shampoo-based formulation of the disclosure. When *Glycine soja* germ extract in butylene glycol and water is used, it may be 0.001% of the shampoo-based formulation of the disclosure. When hydrolyzed barley protein is used, it may be 0.1% of the shampoo-based formulation of the disclosure. When *Wasabia japonica* leaf extract in butylene glycol is used, it may be 0.001% of the shampoo-based formulation of the disclosure. When *Panax Ginseng* root extract in glycerin is used, it may be 0.01% of the shampoo-based formulation of the disclosure. When caffeine is used, it may be 0.001% of the shampoo-based formulation of the disclosure. When biotin is used, it may be 0.001% of the shampoo-based formulation of the disclosure. When *Coffea arabica* seed extract is used, it may be 0.01% of the shampoo-based formulation of the disclosure. When sodium lauroyl methyl isethionate is used, it may be 6% of the shampoo-based formulation of the disclosure. When citric acid is used, it may be 0.25% of the shampoo-based formulation of the disclosure. When sodium cocoyl isethionate is used, it may be 2.1% of the shampoo-based formulation of the disclosure. When sodium benzoate is used, it may be 0.1% of the shampoo-based formulation of the disclosure. When potassium sorbate is used, it may be 0.1% of the shampoo-based formulation of the disclosure. When ethylhexylglycerin is used, it may be 0.1% of the shampoo-based formulation of the disclosure. When guar hydroxypropyltrimonium chloride is used, it may be 0.1% of the shampoo-based formulation of the disclosure. When glycerin is used, it may be 1% of the shampoo-based formulation of the disclosure. When panthenol is used, it may be 1% of the shampoo-based formulation of the disclosure. When cocamidopropyl betaine is used, it may be 30% of the shampoo-based formulation of the disclosure. When amodimethicone is used, it may be 0.3% of the shampoo-based formulation of the disclosure. When fragrance is used, it may be 0.8% of the shampoo-based formulation of the disclosure.

TABLE 2A

Components of an example Shampoo-based Formulation

| Shampoo-based Formulation Component | % W/W |
|---|---|
| Palmitoyl Tetrapeptide-20 Amide in glycerin and water | 2% |
| *Polygonum multiflorum* 8% root extract | 0.001% |
| *Zanthoxylum bungeanum* fruit extract in glycerin and water | 0.001% |
| *Humulus lupulus* extract in glycerin and water | 0.001% |
| *Sesamum indicum* seed extract in glycerin and water | 0.001% |
| *Glycine soja* germ extract in butylene glycol and water | 0.001% |
| Hydrolyzed barley protein | 0.1% |
| *Wasabia japonica* leaf extract in butylene glycol | 0.001% |
| *Panax* Ginseng root extract in glycerin | 0.01% |
| Caffeine | 0.001% |
| Biotin | 0.001% |
| *Coffea arabica* seed extract | 0.01% |
| Sodium lauroyl methyl isethionate | 6% |
| Citric acid | 0.25% |
| Sodium cocoyl isethionate | 2.1% |
| Sodium benzoate | 0.1% |
| Potassium sorbate | 0.1% |
| Ethylhexylglycerin | 0.1% |
| Guar hydroxypropyltrimonium chloride | 0.1% |
| Glycerin | 1% |
| Panthenol | 1% |
| Cocamidopropyl betaine | 30% |
| Amodimethicone | 0.3% |
| Fragrance | 0.8% |
| Water | QSAD |

TABLE 2B

Components of an example Shampoo-based Formulation

| Shampoo-based Formulation Component | % W/W |
|---|---|
| Cocamidopropyl Betaine | 25-30 |
| Sodium Lauroyl Methyl Isethionate | 6 |

TABLE 2B-continued

Components of an example Shampoo-based Formulation

| Shampoo-based Formulation Component | % W/W |
|---|---|
| Sodium Cocoyl Isethionate | 2.1 |
| Glycerin (and) Water (and) Palmitoyl Tetrapeptide Amide (Greyverse) | 20 |
| Glycerin | 2 |
| Glycerin | 1 |
| Panthenol | 1 |
| Fragrance (Sage & Cedar Nat. ISO 9235 #PF-21-07751) | 0.8 |
| Amodimethicone | 0.3 |
| Citric Acid | 0.25 |
| Hydrolyzed Barley Protein | 0.1 |
| Sodium Benzoate | 0.1 |
| Potassium Sorbate | 0.1 |
| Ethylhexylglycerin | 0.1 |
| Guar Hydroxypropyltrimonium Chloride | 0.1 |
| Coffea Arabica (Coffee) Seed Extract | 0.01 |
| Glycerin and Panax Ginseng Root Extract | 0.01 |
| Water and Glycerin and Zanthoxylum Bungeanum Fruit Extract | 0.001 |
| Glycerin and Water and Humulus Lupulus (Hops) Extract | 0.001 |
| Glycerin and Water and Sesamum Indicum Seed Extract | 0.001 |
| Soybean Germ Extract and Water and Butylene Glycol | 0.001 |
| Butylene Glycol and Wasabia Japonica Leaf Extract | 0.001 |
| Polygonum Multiflorum 8% Extract | 0.001 |
| Biotin | 0.001 |
| Caffeine | 0.001 |
| Water | QSAD |

TABLE 2C

Components of an example Dry Shampoo Formulation

| Shampoo-based Formulation Component | % W/W |
|---|---|
| Mica | 53.80 |
| Aluminum Starch Octenylsuccinate | 19.00 |
| Silica | 7.20 |
| Palmitoyl Tetrapeptide-20 Amide | 2.00 |
| Capryloyl Glycine | 0.70 |
| Undecylenoyl Glycine | 0.70 |
| Glycine Soja (Soybean) Germ Extract | 1.00 |
| Wasabia Japonica Leaf Extract | 1.00 |
| Tfu-Ti (Polygonum Multiflorum) Extract | 1.00 |
| Humulus Lupulus (Hops) Flower Extract | 0.50 |
| Panax Ginseng Root Extract | 0.50 |
| Zanthoxylum Bungeanum Fruit Extract | 0.50 |
| Glycerin | 0.50 |
| Sesamum Indicum Seed Extract | 0.50 |
| Butylene Glycol | 0.50 |
| Water | 0.50 |
| Tocopherol | 0.10 |
| Sage & Cedar Natural ISO9235 | 1.00 |
| Iron Oxides CI77492 | 3.00 |
| Iron Oxides CI 77499 | 2.00 |
| Iron Oxides CI 77491 | 4.00 |

TABLE 2D

Components of an example Dry Shampoo Formulation

| Shampoo-based Formulation Component | % W/W |
|---|---|
| Mica | 53.00 |
| Aluminum Starch Octenylsuccinate | 19.00 |
| Silica | 7.2 |
| Palmitoyl Tetrapeptide-20 Amide | 2.00 |
| Capryloyl Glycine | 0.70 |
| Undecylenoyl Glycine | 0.70 |
| Glycine Soja (Soybean) Germ Extract | 1.00 |
| Wasabia Japonica Leaf Extract | 1.00 |
| Tfu-Ti (Polygonum Multiflorum) Extract | 1.00 |
| Humulus Lupulus (Hops) Flower Extract | 0.50 |
| Citrus Reticulata Extract/Citrus Reticulata (Tangerine) Extract | 0.10 |
| Panax Ginseng Root Extract | 0.50 |
| Acetyl Tyrosine | 0.10 |
| Zanthoxylum Bungeanum Fruit Extract | 0.50 |
| Pentylene Glycol | 0.10 |
| Glycerin | 0.50 |
| Gluconolactone | 0.30 |
| Sesamum Indicum Seed Extract | 0.50 |
| Sodium Benzoate | 0.20 |
| Butylene Glycol | 0.50 |
| Water | 0.50 |
| Tocopherol | 0.10 |
| Sage & Cedar Natural ISO9235 | 1.00 |
| Iron Oxides CI 77492 | 3.00 |
| Iron Oxides CI 77499 | 2.00 |
| Iron Oxides CI 77491 | 4.00 |

In the embodiments provided herein, the shampoo-based formulation is manufactured precisely to optimize product consistency and active ingredient delivery upon administration. In the embodiments provided herein, components of the shampoo-based formulation are combined in a stepwise protocol. In the embodiments provided herein, each component is designated as a specific phase of the manufacturing protocol. In the embodiments provided herein, phase A consists of water, sodium lauroyl methyl isethionate, and sodium cocoyl isethionate. In the embodiments provided herein, phase B consists of glycerin and guar hydroxypropyltrimonium chloride. In the embodiments provided herein, phase C consists of panthenol, hydrolyzed barley protein, sodium benzoate, potassium sorbate, ethylhexylglycerin, *Coffea arabica* seed extract, *Panax Ginseng* root extract in glycerin, *Zanthoxylum bungeanum* fruit extract in glycerin and water, *Humulus lupulus* extract in glycerin and water, *Sesamum indicum* seed extract in glycerin and water, *Glycine soja* germ extract in water and butylene glycol, *Wasabia japonica* leaf extract in butylene glycol, *Polygonum Multiflorum* 8% root extract, biotin, and caffeine. In the embodiments provided herein, phase D consists of cocamidopropyl betaine. In the embodiments provided herein, phase E consists of amodimethicone. In the embodiments provided herein, phase F consists of citric acid. In the embodiments provided herein, phase G consists of Palmitoyl Tetrapeptide 20 Amide in glycerin and water, and fragrance.

In the embodiments provided herein, phase A of the shampoo-based formulation is added to 60° C. water and propeller mixed until fully dissolved. In the embodiments provided herein, phase B is premixed and added to phase A slowly, mixing until fully dissolved. In the embodiments provided herein, phase C is added after phase B to the shampoo-based formulation, mixing until uniform. In the embodiments provided herein, phase D is added after phase C to the shampoo-based formulation, mixing until uniform. In the embodiments provided herein, phase E is added after phase D to the shampoo-based formulation, mixing until uniform. In the embodiments provided herein, phase F is premixed and is added after phase E to the shampoo-based formulation, mixing until uniform. In the embodiments provided herein, the temperature of the shampoo-based formulation is lowered to below 45° C. after adding phase F. In the embodiments provided herein, phase G is added after phase F to the shampoo-based formulation when the temperature is below 45° C., mixing until uniform. In the embodiments provided herein, the formulation is mixed and assayed for quality. In the embodiments provided herein, the pH of the formulation at every step of the manufacturing procedure is maintained above a pH of 6, to maintain consistency, color, and efficacy of the formulation.

In the embodiments provided herein, the preparation of the *Polygonum multiflorum* root extract of the formulation of the disclosure produced unexpected beneficial properties. The *Polygonum multiflorum* that are typically used for cosmetics reacts with the formulation of the disclosure to produce a fibrous consistency, noxious odor, and unpleasant browning. The fibrous consistency produced by *Polygonum multiflorum* results in poor delivery of the product due to clogging of the packaging. In addition, the *Polygonum multiflorum* produces an unpleasant smell and a brown and muddy appearance that interfere with subjects' use and enjoyment of the product. Surprisingly, the preparation of the *Polygonum multiflorum* provided in the disclosure herein does not produce a fibrous consistency, unpleasant odor, or unsightly browning of the formulation of the disclosure. The *Polygonum multiflorum* of the formulation is first extracted, concentrated, and spray dried. Then the *Polygonum multiflorum* is dry extracted, ground, sifted, and mixed, thus resulting in a *Polygonum multiflorum* that confers surprising beneficial effects to the formulation of the disclosure. The unexpected beneficial effects conferred by the particular preparation of *Polygonum multiflorum* of the disclosure eliminates the need to recalibrate the components and packaging of the formulation, or to add additional ingredients such as dyes and fragrances to mask unpleasant browning and odors. Thus, the unexpected beneficial effects of the *Polygonum multiflorum* strain of the disclosure reduces costs and lowers the risk of skin irritation that may be caused by additives.

In the embodiments provided herein, the *Humulus lupulus* extract of the formulation of the disclosure is from a particular source selected for its unexpected beneficial properties. The *Humulus lupulus* typically used for cosmetics produce an unpleasant odor, which interferes with subjects' use and enjoyment of the product. To mitigate the impact of unpleasant odors, manufacturers partially mask the presence of *Humulus lupulus* by co-mixing various fragrances. However, addition of more ingredients increases cost as well as the likelihood of skin irritation upon administration. Furthermore, additional ingredients increase the likelihood of negative interactions with other ingredients of the formulation, such as nullifying beneficial effects. The *Humulus lupulus* used in the formulation of the disclosure is Caribgreen Hops. Surprisingly, the source of *Humulus lupulus* provided in the disclosure herein was found not to produce unpleasant odors. The lack of unpleasant odors reduces the need to add fragrances to mask the odor, thus reducing cost and the risk of negative interactions with other ingredients of the formulation.

IX. Conditioner-Based Formulations

In some embodiments, the formulations of the disclosure are conditioner-based. The conditioner-based formulations of the disclosure comprise one or more of *Zanthoxylum bungeanum*, *Humulus lupulus*, *Sesamum indicum* seed, *Panax ginseng* root, or *Polygonum multiflorum* to effectively treat hair follicles, conferring at least one beneficial effect to the hair of a subject. In some embodiments, the conditioner-based formulations of the disclosure are associated with improved hair health. In some embodiments, conditioner-based formulations comprising one or more extracts of *Zanthoxylum bungeanum*, *Humulus lupulus*, *Sesamum indicum* seed, *Panax ginseng* root, or *Polygonum multiflorum* improve the penetration of additional components or products through skin to access hair follicles in the reticular dermis layer and also reduce inflammation of the epidermis.

In some embodiments, conditioner-based formulations of the disclosure improve hair health, with effects including but not limited to: ameliorating depigmentation, inducing pigmentation, promoting pigmentation, maintaining pigmentation, thickening hair shafts, strengthening hair shafts, increasing the density of the hair, increasing the volume of the hair, increasing the volume of the hair, and combinations thereof.

In some embodiments, the pH of the conditioner-based formulation is about 4.0-about 6.0. In some embodiments, the pH of the conditioner-based formulation is about 4.5-about 5.5. In some embodiments, the pH of the conditioner-based formulation is about 4.8. In some embodiments, the viscosity of the conditioner-based formulation is about 8,000-about 25,000 centipoise (cps), as measured at 25° C. on a low viscosity torque (LVT) viscometer at 12 rotations per minute. In some embodiments, the viscosity of the conditioner-based formulation is about 12,500-about 17,500 centipoise (cps). In some embodiments, the viscosity of the condi-based formulation is about 15,000 centipoise (cps).

The conditioner-based formulations may be useful for delivering the active ingredients along with additional moisturizing agents to further contribute to the beneficial hair care effects conferred to the hair, scalp, and skin of the subject in need thereof. In some embodiments, the conditioner-based formulation is some or all of the ingredients described above with respect to the serum-based formulations, and may further comprise conditioning agents that moisturize the hair strand, scalp, and skin surface to help retain moisture and maintain hair health. In some embodiments, the conditioning agents of the disclosure are selected from the group consisting of sorbitol, caprylic/capric triglyceride, isopropyl myristate, sodium PCA, stearamidopropyl dimethylamine, behentrimonium methosulfate, tocopherol, cetyl esters, cetyl alcohol, stearyl alcohol, and combinations thereof.

In an exemplary embodiment, when sorbitol is used, it may be 1% to 3% W/W of the formulation of the disclosure. When caprylic/capric triglyceride is used, it may be 0.5% to 2.5% W/W of the formulation of the disclosure. When cetrimonium chloride is used, it may be 0.5% to 2.5% W/W of the formulation of the disclosure. When isopropyl myristate is used, it may be 0.2% to 2% W/W of the formulation of the disclosure. When sodium PCA is used, it may be 0.1% to 1.5% W/W of the formulation of the disclosure. When stearamidopropyl dimethylamine is used, it may be 0.1% to 1.5% W/W of the formulation of the disclosure. When behentrimonium methosulfate is used, it may be 0.1% to 1.5% W/W of the formulation of the disclosure. When tocopherol is used, it may be 0.01% to 0.2% W/W of the formulation of the disclosure. When cetyl ester is used, it may be 1.5% to 3% W/W of the formulation of the disclosure. When cetyl alcohol is used, it may be 1.5% to 3.5% W/W of the formulation of the disclosure. When stearyl alcohol is used, it may be 1.5% to 3.5% W/W of the formulation of the disclosure.

In some embodiments, the conditioning agents further comprise *Butyrospermum parkii* fruit extract and/or *Simmondsia chinensis* seed oil. In some embodiments, the *Butyrospermum parkii* fruit extract is 0.1% to 1.5% W/W of the formulation of the disclosure. In some embodiments, the *Simmondsia chinensis* seed oil is 0.05% to 0.2% W/W of the formulation of the disclosure.

In an exemplary embodiment, when cetyl esters is used, it may be 1.5% to 3% of the formulation of the disclosure. When cetyl alcohol is used, it may be 1.5% to 3% of the formulation of the disclosure. When stearyl alcohol is used, it may be 1.5% to 3% of the formulation of the disclosure. When sorbitol is used, it may be 1% to 3% of the formulation of the disclosure. When caprylic/capric triglyceride is used, it may be 0.5% to 2.5% of the formulation of the disclosure. When cetrimonium chloride is used, it may be 0.5% to 2.5% of the formulation of the disclosure. When panthenol is used, it may be 0.5% to 2% of the formulation of the disclosure. When fragrance is used, it may be 0.5% to 1.5% of the formulation of the disclosure. When isopropyl myristate is used, it may be 0.2% to 2% of the formulation of the disclosure. When sodium PCA is used, it may be 0.1% to 1.5% of the formulation of the disclosure. When stearamidopropyl dimethylamine is used, it may be 0.1% to 1.5% of the formulation of the disclosure. When behentrimonium methosulfate in cetearyl alcohol is used, it may be 0.1% to 1.5% of the formulation of the disclosure. When *Butyrospermum parkii* fruit extract is used, it may be 0.1% to 1.5% of the formulation of the disclosure. When amodimethicone is used, it may be 0.1% to 0.5% of the formulation of the disclosure. When citric acid is used, it may be 0.05% to 0.3% of the formulation of the disclosure. When *Simmondsia chinensis* seed oil is used, it may be 0.05% to 0.2% of the formulation of the disclosure. When hydrolyzed barley protein is used, it may be 0.01% to 0.2% of the formulation of the disclosure. When potassium sorbate is used, it may be 0.01% to 0.2% of the formulation of the disclosure. When sodium benzoate is used, it may be 0.01% to 0.2% of the formulation of the disclosure. When tocopherol is used, it may be 0.01% to 0.2% of the formulation of the disclosure. When ethylhexylglycerin is used, it may be 0.01% to 0.2% of the formulation of the disclosure. When *Coffea arabica* seed extract is used, it may be 0.005% to 0.05% of the formulation of the disclosure. When *Panax Ginseng* root extract in glycerin is used, it may be 0.005% to 0.05% of the formulation of the disclosure. When *Zanthoxylum bungeanum* fruit extract in glycerin is used, it may be 0.0005% to 0.005% of the formulation of the disclosure. When *Humulus lupulus* extract in water and glycerin is used, it may be 0.0005% to 0.005% of the formulation of the disclosure. When *Sesamum indicum* seed extract in glycerin and water is used, it may be 0.0005% to 0.005% of the formulation of the disclosure. When *Glycine soja* germ extract in butylene glycol and water is used, it may be 0.0005% to 0.005% of the formulation of the disclosure. When *Wasabia japonica* leaf in butylene glycol is used, it may be 0.0005% to 0.005% of the formulation of the disclosure. When *Polygonum multiflorum* 8% root extract is used, it may be 0.0005% to 0.005% of the formulation of the disclosure. biotin is used, it may be 0.0005% to 0.005% of the formulation of the disclosure. When caffeine is used, it may be 0.0005% to 0.005% of the formulation of the disclosure.

X. Methods of Manufacturing Conditioner-Based Formulations

In an exemplary embodiment, when cetyl esters are used, they may be 2.7% of the formulation of the disclosure. When cetyl alcohol is used, it may be 2.25% of the formulation of the disclosure. When stearyl alcohol is used, it may be 2.25% of the formulation of the disclosure. When sorbitol is used, it may be 2% of the formulation of the disclosure. When caprylic/capric triglyceride is used, it may be 1.6% of the formulation of the disclosure. When cetrimonium chloride is used, it may be 1.2% of the formulation of the disclosure. When panthenol is used, it may be 1% of the formulation of the disclosure. When fragrance is used, it may be 0.8% of the formulation of the disclosure. When isopropyl myristate is used, it may be 0.7% of the formulation of the disclosure. When sodium PCA is used, it may be 0.5% of the formulation of the disclosure. When stearamidopropyl dimethylamine is used, it may be 0.5% of the formulation of the disclosure. When behentrimonium methosulfate in cetearyl alcohol is used, it may be 0.5% of the formulation of the disclosure. When *Butyrospermum parkii* fruit extract is used, it may be 0.5% of the formulation of the disclosure. When amodimethicone is used, it may be 0.3% of the formulation of the disclosure. When citric acid is used, it may be 0.2% of the formulation of the disclosure. When *Simmondsia chinensis* seed oil is used, it may be 0.1% of the formulation of the disclosure. When hydrolyzed barley protein is used, it may be 0.1% of the formulation of the disclosure. When potassium sorbate is used, it may be 0.1% of the formulation of the disclosure. When sodium benzoate is used, it may be 0.1% of the formulation of the disclosure. When tocopherol is used, it may be 0.1% of the formulation of the disclosure. When ethylhexylglycerin is used, it may be 0.1% of the formulation of the disclosure. When *Coffea arabica* seed extract is used, it may be 0.01% of the formulation of the disclosure. When *Panax Ginseng* root extract in glycerin is used, it may be 0.01% of the formulation of the disclosure. When *Zanthoxylum bungeanum* fruit extract in glycerin is used, it may be 0.001% of the formulation of the disclosure. When *Humulus lupulus* extract in water and glycerin is used, it may be 0.001% of the formulation of the disclosure. When *Sesamum indicum* seed extract in glycerin and water is used, it may be 0.001% of the formulation of the disclosure. When *Glycine soja* germ extract in butylene glycol and water is used, it may be 0.001% of the formulation of the disclosure. When *Wasabia japonica* leaf in butylene glycol is used, it may be 0.001% of the formulation of the disclosure. When *Polygonum multiflorum* 8% root extract is used, it may be 0.001% of the formulation of the disclosure. biotin is used, it may be 0.001% of the formulation of the disclosure. When caffeine is used, it may be 0.001% of the formulation of the disclosure.

TABLE 3A

Components of an example Conditioner-based Formulation

| Conditioner-based Formulation Component | % W/W |
|---|---|
| Cetyl esters | 2.7% |
| Cetyl alcohol | 2.25% |
| Stearyl alcohol | 2.25% |
| Sorbitol | 2% |
| Caprylic/capric triglyceride | 1.6% |
| Cetrimonium chloride | 1.2% |
| Panthenol | 1% |
| Fragrance | 0.8% |
| Isopropyl myristate | 0.7% |
| Sodium PCA | 0.5% |
| Stearamidopropyl dimethylamine | 0.5% |
| Behentrimonium methosulfate in cetearyl alcohol | 0.5% |
| *Butyrospermum parkii* fruit extract | 0.5% |
| Amodimethicone | 0.3% |
| Citric acid | 0.2% |
| *Simmondsia chinensis* seed oil | 0.1% |
| Hydrolyzed barley protein | 0.1% |
| Potassium sorbate | 0.1% |
| Sodium benzoate | 0.1% |
| Tocopherol | 0.1% |
| Ethylhexylglycerin | 0.1% |
| *Coffea arabica* seed extract | 0.01% |
| *Panax* Ginseng root extract in glycerin | 0.01% |
| *Zanthoxylum bungeanum* fruit extract in glycerin | 0.001% |
| *Humulus lupulus* extract in water and glycerin | 0.001% |
| *Sesamum indicum* seed extract in glycerin and water | 0.001% |
| *Glycine soja* germ extract in butylene glycol and water | 0.001% |
| *Wasabia japonica* leaf in butylene glycol | 0.001% |

TABLE 3A-continued

Components of an example Conditioner-based Formulation

| Conditioner-based Formulation Component | % W/W |
|---|---|
| *Polygonum multiflorum* 8% root extract | 0.001% |
| Biotin | 0.001% |
| Caffeine | 0.001% |
| Water | QSAD |

TABLE 3B

Components of an example Conditioner-based Formulation

| Conditioner-based Formulation Component | % W/W |
|---|---|
| Cetyl Esters | 2.7 |
| Cetyl Alcohol | 2.25 |
| Stearyl Alcohol | 2.25 |
| Sorbitol | 2 |
| Caprylic/Capric Triglyceride | 1.6 |
| Cetrimonium Chloride | 1.2 |
| Panthenol | 1 |
| *Selianthus Annuus* (Sunflower) Seed Extract and C9-12 Alkane and Squalane and *Argania Spinosa* Kernel Oil and *Citrullus Lanatus* (Watermelon) Seed Oil and Coco-Caprylate/Caprate | 1 |
| Fragrance (Sage & Cedar Nat. ISO 9235 #PF-21-07751) | 0.8 |
| Isopropyl Myristate | 0.7 |
| Sodium PCA | 0.5 |
| Stearamidopropyl Dimethylamine | 0.5 |
| Behentrimonium Methosulfate and Cetearyl Alcohol | 0.5 |
| *Butyrospermum Parkii* (Shea) Butter | 0.5 |
| Amodimethicone | 0.3 |
| Citric Acid | 0.2175 |
| *Simmondsia Chinensis* (Jojoba) Seed Oil | 0.1 |
| Hydrolyzed Barley Protein | 0.1 |
| Potassium Sorbate | 0.1 |
| Sodium Benzoate | 0.1 |
| Tocopherol | 0.1 |
| Ethylhexylglycerin | 0.1 |
| *Coffea Arabica* (Coffee) Seed Extract | 0.01 |
| Glycerin and Panax Ginseng Root Extract | 0.01 |
| Water and Glycerin and *Zanthoxylum Bungeanum* Fruit Extract | 0.001 |
| Glycerin and Water and *Humulus Lupulus* (Hops) Extract | 0.001 |
| Glycerin and Water and *Sesamum Indicum* Seed Extract | 0.001 |
| Soybean Germ Extract and Water and Butylene Glycol | 0.001 |
| Butylene Glycol and *Wasabia Japonica* Leaf Extract | 0.001 |
| *Polygonum Multiflorum* Root Extract | 0.001 |
| Biotin | 0.001 |
| Caffeine | 0.001 |
| Water | QSAD |

TABLE 3C

Components of an example leave-in Conditioner-based Formulation

| Leave-in Conditioner-based Formulation component | % W/W |
|---|---|
| Cetyl Alcohol | 3.5% |
| Water, Glycerin, *Salvia Hispanica* Seed Extract, Trehalose Xylitol, Caprylyl/Capryl Glucoside, Ethyl Linoleate, Ethyl Oleate, Sorbitan Oleate, Polyquaternium-37, and Sodium Phosphate | 2% |
| Stearamidodipropyl Dimethylamine | 1.5% |
| *Simmondsia Chinensis* (Jojoba) Seed Oil | 1% |
| Panthenol | 1% |
| Cetrimonium Chloride | 0.99% |
| Fragrance (Sage & Cedar) | 0.8% |
| sr-Hydrozoan Polypeptide-1 (Collagen) | 0.5% |
| Tetrahexyldecyl Ascorbate | 0.5% |
| Behentrimonium Chloride | 0.5% |
| Hydrolyzed Barley Protein | 0.5% |
| Stearamidopropyl Dimethylamine | 0.5% |

TABLE 3C-continued

Components of an example leave-in Conditioner-based Formulation

| Leave-in Conditioner-based Formulation component | % W/W |
|---|---|
| Ethylhexylglycerin | 0.3% |
| Behenyl/Stearyl Aminopropanediol Esters | 0.2% |
| *Butyrospermum Parkii* (Shea) Butter | 0.1% |
| Citric Acid | 0.1% |
| Sodium Benzoate | 0.1% |
| Potassium Sorbate | 0.1% |
| Water | QSAD |

TABLE 3D

Components of an example leave-in Conditioner-based Formulation

| Leave-in Conditioner-based Formulation component | % W/W |
|---|---|
| *Rubus Idaeus* Seed Oil | 1.8 |
| Cetyl Alcohol | 1.5 |
| Stearamidodipropyl Dimethylamine | 1.5 |
| Glyceryl Stearate | 1.5 |
| *Simmondsia Chinensis* (Jojoba) Seed Oil | 1 |
| Panthenol | 1 |
| Cetrimonium Chloride | 0.99 |
| Fragrance (Sage & Cedar Nat. ISO 9235 #PF-21-07751) | 0.8 |
| *Butyrospermum Parkii* (Shea) Butter | 0.6 |
| Hydrolyzed Barley Protein | 0.5 |
| Ethylhexylglycerin | 0.3 |
| Tocopherol | 0.3 |
| Citric Acid | 0.2 |
| Sodium Benzoate | 0.1 |
| Potassium Sorbate | 0.1 |
| Allantoin | 0.1 |
| *Coffea Arabica* (Coffee) Seed Extract | 0.01 |
| Glycerin and Panax Ginseng Root Extract | 0.01 |
| Water and Glycerin and *Zanthoxylum Bungeanum* Fruit Extract | 0.001 |
| Glycerin and Water and *Humulus Lupulus* (Hops) Flower Extract | 0.001 |
| Glycerin and Water and *Sesamum Indicum* Seed Extract | 0.001 |
| Soybean Germ Extract and Water and Butylene Glycol | 0.001 |
| Butylene Glycol and *Wasabia Japonica* Leaf Extract | 0.001 |
| *Polygonum multiflorum* 8% Extract | 0.001 |
| Biotin | 0.001 |
| Caffeine | 0.001 |
| Water | QSAD |

In the embodiments provided herein, the conditioner-based formulation is manufactured precisely to optimize product consistency and active ingredient delivery upon administration. In the embodiments provided herein, components of the conditioner-based formulation are combined in a stepwise protocol. In the embodiments provided herein, each component is designated as a specific phase of the manufacturing protocol. In the embodiments provided herein, phase A consists of water, cetrimonium chloride, sorbitol, panthenol, sodium PCA, hydrolyzed barley protein, potassium sorbate, sodium benzoate, citric acid, biotin, caffeine, ethylhexylglycerin, *Coffea arabica* seed extract, *Panax Ginseng* root extract in glycerin, *Zanthoxylum bungeanum* fruit extract in glycerin and water, *Humulus lupulus* extract in glycerin and water, *Sesamum indicum* seed extract in glycerin and water, *Glycine soja* germ extract in water and butylene glycol, *Wasabia japonica* leaf extract in butylene glycol, and *Polygonum multiflorum* 8% root extract. In the embodiments provided herein, phase B consists of cetyl esters, cetyl alcohol, stearyl alcohol, caprylic/capric triglyceride, isopropyl myristate, stearamidopropyl dimethylamine, behentrimonium methosulfate in cetearyl alcohol, *Butyrospermum parkii* fruit extract, and *Simmondsia chinensis* seed oil. In the embodiments provided herein, phase C consists of tocopherol and amodimethicone. In the embodiments provided herein, phase D consists of sage & cedar non-synthetic fragrance.

In the embodiments provided herein, phase A of the conditioner-based formulation is added to 75° C. water and propeller mixed until fully dissolved. In the embodiments provided herein, phase B is premixed separately and heated to 75° C. until all solids are melted and the phase is uniform. In the embodiments provided herein, phase B is then removed from heat, and heat-sensitive phase C ingredients are added and mixed until homogenous. In the embodiments provided herein, the oil phase from the phase C and phase B mixture is added to phase A with uniform mixing until a uniform emulsion forms. In the embodiments provided herein, once the formulation is uniform, the formulation is assayed for quality. In the embodiments provided herein, the pH of the formulation at every step of the manufacturing procedure is maintained above a pH of 6, to maintain consistency, color, and efficacy of the formulation.

XI. Exfoliant-Based Formulations

In some embodiments, the formulations of the disclosure are exfoliant-based. An exfoliant-based formulation may be helpful for delivering the active ingredients of the formulation directly to the hair strands and hair follicles as the scalp is being exfoliated and cleansed. In some embodiments, the exfoliant-based formulation may comprise some or all of the ingredients of the serum-based formulation described above, and further comprise an exfoliant. For example, an exfoliant-based formulation may comprise a palmitoyl tetrapeptide-20; an extract selected from the group consisting of *Zanthoxylum bungeanum* fruit extract, *Humulus lupulus* extract, *Sesamum indicum* seed extract, *Wasabia japonica* leaf extract, *Glycine soja* germ extract, *Polygonum multiflorum* 8% root extract, and combinations thereof; and an exfoliant.

In some embodiments, the exfoliant-based formulations provided herein are designed to treat hair follicle pigment loss by increasing the effectiveness and delivery of palmitoyl tetrapeptide-20 peptide, which reduces melanocyte death in hair follicles associated with reactive oxygen species (ROS). In some embodiments, the effectiveness of the peptide may be increased by: improving the penetration of the peptide through skin to access the reticular dermis layer; reducing inflammation of the epidermis; or facilitating use by the subject and increasing effectiveness of the product in the form of appropriate viscosity, odor, solubilization, and/or pH. Further, the exfoliant-based formulations provided herein are substantially made of natural and organic ingredients, and are designed to stimulate overall hair health, and to thicken and strengthen hair shafts.

In some embodiments, exfoliant formulations of the disclosure are water-based. In some embodiments, water-based exfoliant formulations provide improved penetration of a treatment through skin and also reduce inflammation of the epidermis relative to comparable oil-based or emulsion-based exfoliant formulations. In some embodiments, water-based exfoliant formulations provide an improved experience for a user, particularly for exfoliant formulations used every day, or more than once a day.

In some embodiments, water-based exfoliant formulations of the disclosure may be optimized to increase solubilization of one or more of *Zanthoxylum bungeanum*, *Humulus lupulus*, *Sesamum indicum* seed, *Panax ginseng* root, or *Polygonum multiflorum* extracts. In some embodiments, water-based exfoliant formulations of the disclosure may be optimized to increase solubilization of an additional component, e.g., a peptide, e.g., palmitoyl tetrapeptide-20 peptide. In some embodiments, optimization of the water-based exfoliant formulations may increase effectiveness, improve the pH of the formulation, improve the odor of the formulation, improve the color of the formulation, improve the viscosity of the formulation, improve the stability of the formulation, and/or improve the scaling of product production.

In some embodiments, the pH of the exfoliant-based formulation is about 4.0-about 6.0. In some embodiments, the viscosity of the exfoliant-based formulation is about 25,000-about 50,000 centipoise (cps), as measured at 25° C. on a low viscosity torque (LVT) viscometer at 12 rotations per minute.

An exfoliant may be helpful for removing dirt and excess oil from the hair, scalp, and the skin surface, as well as removing dandruff and excess skin cells, thus allowing more efficient administration of the active ingredients of the formulation. In some embodiments, the exfoliants of the formulation are chosen from the group consisting of salicylic acid, lactic acid, glycolic acid, and perlite. In some embodiments, the exfoliant salicylic acid is 0.5% to 2% W/W of the formulation of the disclosure. In some embodiments, the exfoliant lactic acid is 0.1% to 1% W/W of the formulation of the disclosure. In some embodiments, the exfoliant glycolic acid is 0.1% to 1% W/W of the formulation of the disclosure. In some embodiments, the exfoliant perlite is 0.1% to 1% W/W of the formulation of the disclosure.

In an exemplary embodiment, when hydroxypropyl starch phosphate is used, it may be 3% to 7% of the formulation of the disclosure. In an exemplary embodiment, when Palmitoyl Tetrapeptide-20 Amide in glycerin and water is used, it may be 1% to 4% of the formulation of the disclosure. In an exemplary embodiment, when *Zanthoxylum bungeanum* fruit extract in glycerin and water is used, it may be 0.5% to 3% of the formulation of the disclosure. In an exemplary embodiment, when *Humulus lupulus* extract in glycerin and water is used, it may be 0.5% to 3% of the formulation of the disclosure. In an exemplary embodiment, when *Sesamum indicum* seed extract in glycerin and water is used, it may be 0.5% to 2.5% of the formulation of the disclosure. In an exemplary embodiment, when salicyclic acid is used, it may be 0.5% to 2% W/W of the formulation of the disclosure. In an exemplary embodiment, when *Wasabia japonica* leaf extract in butylene glycol is used, it may be 0.5% to 2% of the formulation of the disclosure. In an exemplary embodiment, when *glycine soja* germ extract in butylene glycol and water is used, it may be 0.5% to 2% of the formulation of the disclosure. In an exemplary embodiment, when sorbitan oleate decylglycoside crosspolymer is used, it may be 0.5% to 2% of the formulation of the disclosure. In an exemplary embodiment, when fragrance is used, it may be 0.5% to 2% of the formulation of the disclosure. In an exemplary embodiment, when lactic acid is used, it may be 0.2% to 1.5% of the formulation of the disclosure. In an exemplary embodiment, when glycolic acid is used, it may be 0.2% to 1.5% of the formulation of the disclosure. In an exemplary embodiment, when perlite is used, it may be 0.2% to 1.5% of the formulation of the disclosure. In an exemplary embodiment, when ethylhexylglycerin is used, it may be 0.1% to 1% of the formulation of the disclosure. In an exemplary embodiment, when menthol is used, it may be 0.005% to 0.1% of the formulation of the disclosure. In an exemplary embodiment, when *Polygonum multiflorum* 8% root extract is used, it may be 0.0005% to 0.01% of the formulation of the disclosure. In an exemplary embodiment, when caffeine is used, it may be 0.0005% to 0.01% of the formulation of the disclosure. In an exemplary embodiment, when biotin is used, it may be 0.0005% to 0.01% of the formulation of the disclosure.

XII. Methods of Manufacturing Exfoliant-Based Formulations

In an exemplary embodiment, when hydroxypropyl starch phosphate is used, it may be 5.25% of the formulation of the disclosure. In an exemplary embodiment, when Palmitoyl Tetrapeptide-20 Amide in glycerin and water is used, it may be 2% of the formulation of the disclosure. In an exemplary embodiment, when *Zanthoxylum bungeanum* fruit extract in glycerin and water is used, it may be 1.5% of the formulation of the disclosure. In an exemplary embodiment, when *Humulus lupulus* extract in glycerin and water is used, it may be 1.5% of the formulation of the disclosure. In an exemplary embodiment, when *Sesamum indicum* seed extract in glycerin and water is used, it may be 1.2% of the formulation of the disclosure. In an exemplary embodiment, when salicyclic acid is used, it may be 1% of the formulation of the disclosure. In an exemplary embodiment, when *Wasabia japonica* leaf extract in butylene glycol is used, it may be 1% of the formulation of the disclosure. In an exemplary embodiment, when *glycine soja* germ extract in butylene glycol and water is used, it may be 1% of the formulation of the disclosure. In an exemplary embodiment, when sorbitan oleate decylglycoside crosspolymer is used, it may be 1% of the formulation of the disclosure. In an exemplary embodiment, when fragrance is used, it may be 0.8% of the formulation of the disclosure. In an exemplary embodiment, when lactic acid is used, it may be 0.5% of the formulation of the disclosure. In an exemplary embodiment, when glycolic acid is used, it may be 0.5% of the formulation of the disclosure. In an exemplary embodiment, when perlite is used, it may be 0.5% of the formulation of the disclosure. In an exemplary embodiment, when ethylhexylglycerin is used, it may be 0.3% of the formulation of the disclosure. In an exemplary embodiment, when menthol is used, it may be 0.01% of the formulation of the disclosure. In an exemplary embodiment, when *Polygonum multiflorum* 8% root extract is used, it may be 0.001% of the formulation of the disclosure. In an exemplary embodiment, when caffeine is used, it may be 0.001% of the formulation of the disclosure. In an exemplary embodiment, when biotin is used, it may be 0.001% of the formulation of the disclosure.

TABLE 4A

Components of an example Exfoliant-based Formulation

| Exfoliant-based Formulation Component | % W/W |
|---|---|
| Hydroxypropyl Starch Phosphate | 5.25% |
| Palmitoyl Tetrapeptide-20 Amide in glycerin and water | 2% |
| *Zanthoxylum bungeanum* fruit extract in glycerin and water | 1.5% |
| *Humulus lupulus* extract in glycerin and water | 1.5% |
| *Sesamum indicum* seed extract in glycerin and water | 1.2% |
| Salicylic Acid | 1% |
| *Wasabia japonica* leaf extract in butylene glycol | 1% |
| *Glycine soja* germ extract in butylene glycol and water | 1% |
| Sorbitan Oleate Decylglucoside Crosspolymer | 1% |
| Fragrance | 0.8% |
| Lactic Acid | 0.5% |
| Glycolic Acid | 0.5% |
| Perlite | 0.5% |
| Ethylhexylglycerin | 0.3% |
| Menthol | 0.01% |
| *Polygonum multiflorum* 8% root extract | 0.001% |
| Caffeine | 0.001% |

TABLE 4A-continued

Components of an example Exfoliant-based Formulation

| Exfoliant-based Formulation Component | % W/W |
|---|---|
| Biotin | 0.001% |
| Sodium Hydroxide | QS |
| Water | QSAD |

TABLE 4B

Components of an example Exfoliant-based Formulation

| Exfoliant-based Formulation Component | % W/W |
|---|---|
| Hydroxypropyl Starch Phosphate | 5.25 |
| Glycerin and Water and Palmitoyl Tetrapeptide 20 Amide (Greyverse) | 2 |
| *Citrus Reticulata* (Tangerine) Extract and Acetyl Tyrosine and Pentylene Glycol and Gluconolactone and Sodium Benzoate and Water (Melanogray) | 2 |
| Water and Glycerin and *Zanthoxylum Bungeanum* Fruit Extract | 1.5 |
| Glycerin and Water and *Humulus Lupulus* (Hops) Flower Extract | 1.5 |
| Glycerin and Water and *Sesamum Indicum* Seed Extract | 1.2 |
| 1,2-Hexanediol and Caprylyl Glycol | 1 |
| Salicylic Acid | 1 |
| Panthenol | |
| Butylene Glycol and *Wasabia Japonica* Leaf Extract | 1 |
| Soybean Germ Extract and Water and Butylene Glycol | 1 |
| Sorbitan Oleate Decylglucoside Crosspolymer | 1 |
| Fragrance (Sage & Cedar) | 0.8 |
| Lactic Acid | 0.5 |
| Glycolic Acid | 0.5 |
| Perlite | 0.5 |
| Ethylhexylglycerin | 0.3 |
| Menthol | 0.01 |
| *Polygonum Multiflorum* Root Extract (8%) | 0.001 |
| Caffeine | 0.001 |
| Biotin | 0.001 |
| Sodium Hydroxide | QS to pH |
| Water | QSAD |

XIII. Oral Supplements

In some embodiments, the formulations of the disclosure may be used with an orally administered supplement. Without being bound by any particular theory, it is thought that upon metabolizing the supplement, the ingredients of the orally administered supplement get incorporated into hair follicles, hair strands, scalp, and skin surface. In some embodiments, the orally administered supplement is comprised of a vitamin, a mineral, and a nutrient, all of which are formulated to contribute to and enhance the beneficial hair care effects described throughout the disclosure. In some embodiments, an oral supplement may improve the health of hair, with effects including but not limited to: ameliorating depigmentation, inducing pigmentation, promoting pigmentation, maintaining pigmentation, thickening hair shafts, strengthening hair shafts, increasing the density of the hair, increasing the volume of the hair, and combinations thereof. In some embodiments, an oral supplement of the disclosure is used in combination with another product of the disclosure, e.g., a serum-based formulation, a shampoo-based formulation, a conditioner-based formulation, or an exfoliant-based formulation, to improve the health of hair, with effects including but not limited to: ameliorating depigmentation, inducing pigmentation, promoting pigmentation, maintaining pigmentation, thickening hair shafts, strengthening hair shafts, increasing the density of the hair, increasing the volume of the hair, and combinations thereof.

In some embodiments, the vitamin of the oral supplement is from the group selected from vitamin D, vitamin B12, folate, biotin, pantothenic acid, vitamin B6, or combinations thereof. In some embodiments, the vitamin D is 15 to 35 mcg of the oral supplement. In some embodiments, the vitamin B12 is 3 to 9 mcg of the oral supplement. In some embodiments, the vitamin folate is 600 to 700 mcg of the oral supplement. In some embodiments, the biotin is 200 to 400 mcg of the oral supplement. In some embodiments, the pantothenic acid is 150 to 250 mcg of the oral supplement. In some embodiments, the vitamin B6 is 5 to 15 mcg of the oral supplement.

In some embodiments, the vitamin D of the oral supplement is D3 cholecalciferol. In some embodiments, the vitamin B12 of the oral supplement is methylcobalamin. In some embodiments, the pantothenic acid of the oral supplement is D-calcium pantothenate. In some embodiments, the vitamin B6 of the oral supplement is pyroxidine HCl. In some embodiments, the folate is calcium-L-5-methyltetrahydrofolate (MTHF).

In some embodiments, the mineral of the oral supplement is from the group selected from calcium, iron, copper, selenium, or combinations thereof. In some embodiments, the calcium is 200 to 400 mg of the oral supplement. In some embodiments, the iron is 5 to 15 mg of the oral supplement. In some embodiments, the copper is 0.5 to 4 mg of the oral supplement. In some embodiments, the selenium is 45 to 65 mcg of the oral supplement.

In some embodiments, the calcium of the oral supplement is calcium carbonate. In some embodiments, the iron of the oral supplement is ferrous fumarate. In some embodiments, the copper of the oral supplement is copper gluconate. In some embodiments, the selenium of the oral supplement is selenomethionine.

In some embodiments, the nutrient of the oral supplement is a blend of para-aminobenzoic acid, *Sesamum indicum* extract, and *Polygonum multiflorum* extract. In some embodiments, the blend of para-aminobenzoic acid, *Sesamum indicum* extract, and *Polygonum multiflorum* extract is 300 to 400 mg of the oral supplement.

In an exemplary embodiment, when vitamin D is used, it may be 15 to 35 mcg of the supplement of the disclosure. When vitamin B6 is used, it may be 5 to 15 mg of the supplement of the disclosure. When folate is used, it may be 600 to 700 mcg of the supplement of the disclosure. When vitamin B12 is used, it may be 3 to 9 mcg of the supplement of the disclosure. When biotin is used, it may be 200 to 400 mcg of the supplement of the disclosure. When pantothenic acid is used, it may be 150 to 250 mg of the supplement of the disclosure. When calcium is used, it may be 200 to 400 mg of the supplement of the disclosure. When iron is used, it may be 5 to 15 mg of the supplement of the disclosure. When selenium is used, it may be 45 to 65 mcg of the supplement of the disclosure. When copper is used, it may be 0.5 to 4 mg of the supplement of the disclosure. When a blend of para-aminobenzoic acid (PABA), *Sesamum indicum* seed extract, and *Polygonum multiflorum* root extract is used, it may be 300 to 400 mg of the supplement of the disclosure.

In an exemplary embodiment, when vitamin D is used, it may be 25 mcg of the supplement of the disclosure. When vitamin B6 is used, it may be 10 mg of the supplement of the disclosure. When folate is used, it may be 665 mcg of the supplement of the disclosure. When vitamin B12 is used, it may be 6 mcg of the supplement of the disclosure. When biotin is used, it may be 300 mcg of the supplement of the disclosure. When pantothenic acid is used, it may be 200 mg of the supplement of the disclosure. When calcium is used, it may be 300 mg of the supplement of the disclosure. When iron is used, it may be 9 mg of the supplement of the disclosure. When selenium is used, it may be 55 mcg of the supplement of the disclosure. When copper is used, it may be 2 mg of the supplement of the disclosure. When a blend of para-aminobenzoic acid (PABA), *Sesamum indicum* seed extract, and *Polygonum multiflorum* root extract is used, it may be 335 mg of the supplement of the disclosure.

TABLE 5

Components of an example Oral Supplement

| Components of the Oral Supplement | Amount Per Serving |
|---|---|
| Vitamin D | 25 mcg |
| Vitamin B6 | 10 mg |
| Folate | 665 mcg |
| Vitamin B12 | 6 mcg |
| Biotin | 300 mcg |
| Pantothenic acid | 200 mg |
| Calcium | 300 mg |
| Iron | 9 mg |
| Selenium | 55 mcg |
| Copper | 2 mg |
| Blend of para-aminobenzoic acid (PABA), black sesame seed extract, and fo-ti root | 335 mg |
| Additional ingredients: Hypromellose, Rice Flour, Magnesium Stearate, Silica | |

XIV. Methods of Use

As described herein throughout, the formulations disclosed herein imparts at least one beneficial hair care effect. These include, but are not limited to: ameliorating depigmentation, inducing pigmentation, promoting pigmentation, maintaining pigmentation, thicker hair shafts, stronger hair shafts, denser hair, more hair volume, and combinations thereof. In some embodiments, indications for use of the formulation of the disclosure include the alleviation of depigmentation of the hair shaft. In some embodiments, indications for use of the formulation of the disclosure include the induction of pigmentation of the hair shaft. In some embodiments, indications for use of the formulation of the disclosure include the maintenance of the pigmentation of the hair shaft. In some embodiments, indications for use of the formulation of the disclosure include the promotion of pigmentation of the hair shaft. In some embodiments, indications for use of the formulation of the disclosure include the treatment of thinning hair shafts. In some embodiments, indications for use of the formulation of the disclosure include the treatment of weakening hair shafts. In some embodiments, indications for use of the formulation of the disclosure include the treatment of thinning hair. In some embodiments, indications for use of the formulation of the disclosure include the treatment of loss of volume of hair.

The formulations of the disclosure confer at least one beneficial hair care effects on various types of hairs. In some embodiments, the formulation of the disclosures confers a hair care effect with respect to facial, head, or body hair. In some embodiments, the formulations of the disclosure confers a hair care effect with respect to facial hair. In some embodiments, the formulations of the disclosure confers a hair care effect to facial hair, wherein the facial hair includes eyebrow hair, eyelash hair, mustache hair, cheek hair, beard hair, lower lip hair, goatee hair, whiskers, sideburns, ear hair, nose hair, or combinations thereof. In some embodiments, the formulations of the disclosures confer a hair care effect to body hair, wherein the body hair includes wherein the body hair is neck hair, chest hair, shoulder hair, arm hair, axillary hair, hand hair, abdominal hair, back hair, pubic hair, gluteal hair, perineal hair, thigh hair, leg hair, foot hair, or combinations thereof. In some embodiments, the formulations of the disclosure confer a hair care effect to head hair.

Serum-Based Formulations

As described in detail above, the formulations of the disclosure may be in the form of a serum. The serum-based formulations allow topical application of the concentrated ingredients and is left on after application. In some embodiments, the serum-based formulation can be used to alleviate depigmentation of the hair shaft. In some embodiments, the serum-based formulation can be used to induce pigmentation in the hair shaft. In some embodiments, the serum-based formulation can be used to maintain pigmentation of the hair shaft. In some embodiments, the serum-based formulation can be used to promote pigmentation of the hair shaft. In some embodiments, the serum-based formulation can be used to treat the thinning of hair shafts. In some embodiments, the serum-based formulation can be used to treat the weakening of hair shafts. In some embodiments, the serum-based formulation can be used to treat thinning hair. In some embodiments, the serum-based formulation can be used to treat loss of volume of hair.

The serum-based formulation is most often used for head hair, but may be used with any other suitable hair as well. For example, the serum-based formulation can be applied topically wherever the subject wishes to impart at least one hair care benefit. In some embodiments, the serum-based formulation can be applied to facial hair. In some embodiments, the serum-based formulation can be applied to body hair. In some embodiments, the serum-based formulation can be applied to eyebrow hair, eyelash hair, mustache hair, cheek hair, beard hair, lower lip hair, goatee hair, whiskers, sideburns, ear hair, nose hair, or combinations thereof. In some embodiments, the serum-based formulation can be applied to head hair, neck hair, chest hair, shoulder hair, arm hair, axillary hair, hand hair, abdominal hair, back hair, pubic hair, gluteal hair, perineal hair, thigh hair, leg hair, foot hair, or combinations thereof.

The serum-based formulation may be packaged in a pump bottle for application, and each pump may result in a particular dose or dispensing of the serum-based formulation. For example, in some embodiments, 2 pumps approximately correspond to 2 mL of the serum-based application. In some embodiments, the serum-based formulation is applied at a dose of 1 mL to 3 mL. In some embodiments, the serum-based formulation is applied at a dose of 1 mL. In some embodiments, the serum-based formulation is applied at a dose of 1.5 mL. In some embodiments, the serum-based formulation is applied at a dose of 2 mL. In some embodiments, the serum-based formulation is applied at a dose of 2.5 mL. In some embodiments, the serum-based formulation is applied at a dose of 3 mL. In some embodiments, the pump bottle is designed to minimize or not allow exposure to air or light.

In some embodiments, the serum-based formulations of the disclosure can be applied topically to the hair of interest and be massaged on the skin surface. In some embodiments, the serum-based formulations can be applied directly on the skin surface. In some embodiments, the serum-based formulations can be applied on the scalp surface. In some embodiments, the serum-based formulations can be applied to hair strands. In some embodiments, the serum-based formulations can be applied to hair follicles.

In some embodiments, the serum-based formulation is applied 1 to 3 times per day. In some embodiments, the serum-based formulation is applied once per day. In some embodiments, the serum-based formulation is applied 2 times per day. In some embodiments, the serum-based formulation is applied 3 times per day. In some embodiments, the serum-based formulation is applied prior to loss of hair pigmentation. In some embodiments, the serum-based formulation is applied at the onset of the loss of hair pigmentation. In some embodiments, the serum-based formulation is applied daily for at least 1 month. In some embodiments, the serum-based formulation is applied daily for at least 2 months. In some embodiments, the serum-based formulation is applied daily for at least 3 months. In some embodiments, the serum-based formulation is applied daily for at least 4 months. In some embodiments, the serum-based formulation is applied daily for at least 5 months. In some embodiments, the serum-based formulation is applied daily for at least 6 months.

The oral supplement to the formulation can be taken in conjunction with use of the serum-based formulation of the disclosure. In some embodiments, the oral supplement is ingested at least once a day. In some embodiments, the oral supplement is ingested at 2 times per day. In some embodiments, the oral supplement is ingested at 3 times per day. In some embodiments, the oral supplement is ingested at 4 times per day. In some embodiments, the oral supplement is ingested at 5 times per day. In some embodiments, the oral supplement is ingested at least once every 2 days. In some embodiments, the oral supplement is ingested at least once every 3 days. In some embodiments, the oral supplement is ingested at least once every 4 days. In some embodiments, the oral supplement is ingested at least once every 5 days. In some embodiments, the oral supplement is ingested at least once every 6 days. In some embodiments, the oral supplement is ingested at least once every 7 days.

Shampoo-Based Formulations

As described in detail above, the formulations of the disclosure may be in the form of a shampoo. A shampoo-based formulation may allow topical application of the ingredients as the hair is being cleansed, and be rinsed off after use. In some embodiments, the shampoo-based formulation can be used to alleviate depigmentation of the hair shaft. In some embodiments, the shampoo-based formulation can be used to induce pigmentation in the hair shaft. In some embodiments, the shampoo-based formulation can be used to maintain pigmentation of the hair shaft. In some embodiments, the shampoo-based formulation can be used to promote pigmentation of the hair shaft. In some embodiments, the shampoo-based formulation can be used to treat the thinning of hair shafts. In some embodiments, the shampoo-based formulation can be used to treat the weakening of hair shafts. In some embodiments, the shampoo-based formulation can be used to treat thinning hair. In some embodiments, the shampoo-based formulation can be used to treat loss of volume of hair.

The shampoo-based formulation may most often be used for head, but can be used with any other suitable hair as well. For example, the shampoo-based formulation can be applied topically wherever the subject wishes to impart at least one hair care benefit. In some embodiments, the shampoo-based formulation can be applied to facial hair. In some embodiments, the shampoo-based formulation can be applied to body hair. In some embodiments, the shampoo-based formulation can be applied to eyebrow hair, eyelash hair, mustache hair, cheek hair, beard hair, lower lip hair, goatee hair, whiskers, sideburns, ear hair, nose hair, or combinations thereof. In some embodiments, the shampoo-based formulation can be applied to head hair, neck hair, chest hair, shoulder hair, arm hair, axillary hair, hand hair, abdominal hair, back hair, pubic hair, gluteal hair, perineal hair, thigh hair, leg hair, foot hair, or combinations thereof.

In some embodiments, the shampoo-based formulation is applied at a dose of 7 mL to 10 mL. In some embodiments, the shampoo-based formulation is applied at a dose of 7 mL. In some embodiments, the shampoo-based formulation is applied at a dose of 7.5 mL. In some embodiments, the shampoo-based formulation is applied at a dose of 8 mL. In some embodiments, the shampoo-based formulation is applied at a dose of 8.5 mL. In some embodiments, the shampoo-based formulation is applied at a dose of 9 mL. In some embodiments, the shampoo-based formulation is applied at a dose of 9.5 mL. In some embodiments, the shampoo-based formulation is applied at a dose of 10 mL.

In some embodiments the shampoo-based formulation is applied topically to the hair. In some embodiments the shampoo-based formulation is applied topically to moist or wet hair. In some embodiments the shampoo-based formulation is applied topically to dry hair. In some embodiments the shampoo-based formulation is applied and massaged into a rich foam. In some embodiments the shampoo-based formulation is applied and massaged into the scalp. In some embodiments the shampoo-based formulation is applied and massaged into the skin surface. In some embodiments the shampoo-based formulation is applied and rinsed with water. In some embodiments, the shampoo-based formulation is applied and left on for at least 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, or 15 minutes. In some embodiments the shampoo-based formulation is applied and does not cause irritation.

In some embodiments, the shampoo-based formulation is applied 1 to 3 times per day. In some embodiments, the shampoo-based formulation is applied once per day. In some embodiments, the shampoo-based formulation is applied 2 times per day. In some embodiments, the shampoo-based formulation is applied 3 times per day. In some embodiments, the shampoo-based formulation is applied prior to loss of hair pigmentation. In some embodiments, the shampoo-based formulation is applied at the onset of the loss of hair pigmentation. In some embodiments, the shampoo-based formulation is applied daily for at least 1 month. In some embodiments, the shampoo-based formulation is applied daily for at least 2 months. In some embodiments, the shampoo-based formulation is applied daily for at least 3 months. In some embodiments, the shampoo-based formulation is applied daily for at least 4 months. In some embodiments, the shampoo-based formulation is applied daily for at least 5 months. In some embodiments, the shampoo-based formulation is applied daily for at least 6 months.

The oral supplements of the formulation can be taken in conjunction with use of the shampoo-based formulations of the disclosure. In some embodiments, the oral supplement is ingested at least once a day. In some embodiments, the oral supplement is ingested at 2 times per day. In some embodiments, the oral supplement is ingested at 3 times per day. In some embodiments, the oral supplement is ingested at 4 times per day. In some embodiments, the oral supplement is ingested at 5 times per day. In some embodiments, the oral supplement is ingested at least once per day. In some embodiments, the oral supplement is ingested at least once every 2 days. In some embodiments, the oral supplement is ingested at least once every 3 days. In some embodiments, the oral supplement is ingested at least once every 4 days. In some embodiments, the oral supplement is ingested at least once every 5 days. In some embodiments, the oral supplement is ingested at least once every 6 days. In some embodiments, the supplement is ingested at least once every 7 days.

Conditioner-Based Formulations

As described in detail above, the formulations of the disclosure may be in the form of a conditioner. A conditioner-based formulation may allow for topical application of the ingredients as the hair is further moisturized during cleansing, and may be rinsed off after application. In some embodiments, the conditioner-based formulation can be used to alleviate depigmentation of the hair shaft. In some embodiments, the conditioner-based formulation can be used to induce pigmentation in the hair shaft. In some embodiments, the conditioner-based formulation can be used to maintain pigmentation of the hair shaft. In some embodiments, the conditioner-based formulation can be used to promote pigmentation of the hair shaft. In some embodiments, the conditioner-based formulation can be used to treat the thinning of hair shafts. In some embodiments, the conditioner-based formulation can be used to treat the weakening of hair shafts. In some embodiments, the conditioner-based formulation can be used to treat thinning hair. In some embodiments, the conditioner-based formulation can be used to treat loss of volume of hair.

In some embodiments, the conditioner-based formulation is most often used for head hair, but it may be used for any other suitable hair as well. For example, the conditioner-based formulations can be applied topically wherever the subjects wishes to impart at least one hair care benefit. In some embodiments, the conditioner-based formulation can be applied to facial hair. In some embodiments, the conditioner-based formulation can be applied to body hair. In some embodiments, the conditioner-based formulation can be applied to eyebrow hair, eyelash hair, mustache hair, cheek hair, beard hair, lower lip hair, goatee hair, whiskers, sideburns, ear hair, nose hair, or combinations thereof. In some embodiments, the conditioner-based formulation can be applied to head hair, neck hair, chest hair, shoulder hair, arm hair, axillary hair, hand hair, abdominal hair, back hair, pubic hair, gluteal hair, perineal hair, thigh hair, leg hair, foot hair, or combinations thereof.

In some embodiments, the conditioner-based formulation is applied at a dose of 7 mL to 10 mL. In some embodiments, the conditioner-based formulation is applied at a dose of 7 mL. In some embodiments, the conditioner-based formulation is applied at a dose of 7.5 mL. In some embodiments, the conditioner-based formulation is applied at a dose of 8 mL. In some embodiments, the conditioner-based formulation is applied at a dose of 8.5 mL. In some embodiments, the conditioner-based formulation is applied at a dose of 9 mL. In some embodiments, the conditioner-based formulation is applied at a dose of 9.5 mL. In some embodiments, the conditioner-based formulation is applied at a dose of 10 mL.

In some embodiments, the conditioner-based formulation is applied topically to the hair. In some embodiments, the conditioner-based formulation is applied topically to moist or wet hair. In some embodiments, the conditioner-based formulation is applied to dry hair. In some embodiments, the conditioner-based formulation is applied and massaged into the hair. In some embodiments, the conditioner-based formulation is applied and massaged into the scalp. In some embodiments, the conditioner-based formulation is applied and rinsed with water. In some embodiments, the conditioner-based formulation is applied and left on for at least 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, or 15 minutes. In some embodiments the conditioner-based formulation is applied and does not cause irritation.

In some embodiments, the conditioner-based formulation is applied 1 to 3 times per day. In some embodiments, the conditioner-based formulation is applied once per day. In some embodiments, the conditioner-based formulation is applied 2 times per day. In some embodiments, the conditioner-based formulation is applied 3 times per day. In some embodiments, the conditioner-based formulation is applied prior to loss of hair pigmentation. In some embodiments, the conditioner-based formulation is applied at the onset of the loss of hair pigmentation. In some embodiments, the conditioner-based formulation is applied daily for at least 1 month. In some embodiments, the conditioner-based formulation is applied daily for at least 2 months. In some embodiments, the conditioner-based formulation is applied daily for at least 3 months. In some embodiments, the conditioner-based formulation is applied daily for at least 4 months. In some embodiments, the conditioner-based formulation is applied daily for at least 5 months. In some embodiments, the conditioner-based formulation is applied daily for at least 6 months.

The oral supplement to the formulation can be taken in conjunction with use of the conditioner-based formulation of the disclosure. In some embodiments, the oral supplement is ingested at least once a day. In some embodiments, the oral supplement is ingested at 2 times per day. In some embodiments, the oral supplement is ingested at 3 times per day. In some embodiments, the oral supplement is ingested at 4 times per day. In some embodiments, the oral supplement is ingested at 5 times per day. In some embodiments, the oral supplement is ingested at least once per day. In some embodiments, the oral supplement is ingested at least once every 2 days. In some embodiments, the oral supplement is ingested at least once every 3 days. In some embodiments, the oral supplement is ingested at least once every 4 days. In some embodiments, the oral supplement is ingested at least once every 5 days. In some embodiments, the oral supplement is ingested at least once every 6 days. In some embodiments, the supplement is ingested at least once every 7 days.

Exfoliant-Based Formulations

As described in detail above, the formulations of the disclosure may be in the form of an exfoliant. An exfoliant-based formulation may allow topical application of the ingredients to the scalp as the hair and scalp are being cleansed, and be rinsed off after use. In some embodiments, the exfoliant-based formulation can be used to alleviate depigmentation of the hair shaft. In some embodiments, the exfoliant-based formulation can be used to induce pigmentation in the hair shaft. In some embodiments, the exfoliant-based formulation can be used to maintain pigmentation of the hair shaft. In some embodiments, the exfoliant-based formulation can be used to promote pigmentation of the hair shaft. In some embodiments, the exfoliant-based formulation can be used to treat the thinning of hair shafts. In some embodiments, the exfoliant-based formulation can be used to treat the weakening of hair shafts. In some embodiments, the exfoliant-based formulation can be used to treat thinning hair. In some embodiments, the exfoliant-based formulation can be used to treat loss of volume of hair.

The exfoliant-based formulation may most often be used for head, but can be used with any other suitable hair as well. For example, the exfoliant-based formulation can be applied topically wherever the subject wishes to impart at least one hair care benefit. In some embodiments, the exfoliant-based formulation can be applied to facial hair. In some embodiments, the exfoliant-based formulation can be applied to body hair. In some embodiments, the exfoliant-based formulation can be applied to eyebrow hair, eyelash hair, mustache hair, cheek hair, beard hair, lower lip hair, goatee hair, whiskers, sideburns, ear hair, nose hair, or combinations thereof. In some embodiments, the exfoliant-based formulation can be applied to head hair, neck hair, chest hair, shoulder hair, arm hair, axillary hair, hand hair, abdominal hair, back hair, pubic hair, gluteal hair, perineal hair, thigh hair, leg hair, foot hair, or combinations thereof.

In some embodiments, the exfoliant-based formulation is applied at a dose of 7 mL to 12 mL. In some embodiments, the exfoliant-based formulation is applied at a dose of 7 mL. In some embodiments, the exfoliant-based formulation is applied at a dose of 7.5 mL. In some embodiments, the exfoliant-based formulation is applied at a dose of 8 mL. In some embodiments, the exfoliant-based formulation is applied at a dose of 8.5 mL. In some embodiments, the exfoliant-based formulation is applied at a dose of 9 mL. In some embodiments, the exfoliant-based formulation is applied at a dose of 9.5 mL. In some embodiments, the exfoliant-based formulation is applied at a dose of 10 mL. In some embodiments, the exfoliant-based formulation is applied at a dose of 10.5 mL. In some embodiments, the exfoliant-based formulation is applied at a dose of 11 mL. In some embodiments, the exfoliant-based formulation is applied at a dose of 11.5 mL. In some embodiments, the exfoliant-based formulation is applied at a dose of 12 mL.

In some embodiments the exfoliant-based formulation is applied topically to the scalp. In some embodiments the exfoliant-based formulation is applied topically to moist or wet scalp. In some embodiments the exfoliant-based formulation is applied topically to dry scalp. In some embodiments the exfoliant-based formulation is applied and massaged into the scalp. In some embodiments the exfoliant based formulation is applied and massaged into the skin surface. In some embodiments the exfoliant-based formulation is applied and rinsed with water. In some embodiments, the exfoliant-based formulation is applied and left on for at least 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, or 15 minutes. In some embodiments the exfoliant-based formulation is applied and does not cause irritation.

In some embodiments, the exfoliant-based formulation is applied 1 to 3 times per day. In some embodiments, the exfoliant-based formulation is applied once per day. In some embodiments, the exfoliant-based formulation is applied 2 times per day. In some embodiments, the exfoliant-based formulation is applied 3 times per day. In some embodiments, the exfoliant-based formulation is applied prior to loss of hair pigmentation. In some embodiments, the exfoliant-based formulation is applied at the onset of the loss of hair pigmentation. In some embodiments, the exfoliant-based formulation is applied daily for at least 1 month. In some embodiments, the exfoliant-based formulation is applied daily for at least 2 months. In some embodiments, the exfoliant-based formulation is applied daily for at least 3 months. In some embodiments, the exfoliant-based formulation is applied daily for at least 4 months. In some embodiments, the exfoliant-based formulation is applied daily for at least 5 months. In some embodiments, the exfoliant-based formulation is applied daily for at least 6 months.

The oral supplements of the formulation can be taken in conjunction with use of the exfoliant-based formulations of the disclosure. In some embodiments, the oral supplement is ingested at least once a day. In some embodiments, the oral supplement is ingested at 2 times per day. In some embodiments, the oral supplement is ingested at 3 times per day. In some embodiments, the oral supplement is ingested at 4 times per day. In some embodiments, the oral supplement is ingested at 5 times per day. In some embodiments, the oral supplement is ingested at least once per day. In some embodiments, the oral supplement is ingested at least once every 2 days. In some embodiments, the oral supplement is ingested at least once every 3 days. In some embodiments, the oral supplement is ingested at least once every 4 days. In some embodiments, the oral supplement is ingested at least once every 5 days. In some embodiments, the oral supplement is ingested at least once every 6 days. In some embodiments, the supplement is ingested at least once every 7 days.

Oral Supplements

As described in detail above, in some embodiments, oral supplements may be administered in combination with the topical based formulations of the disclosure. In some embodiments, the oral supplement can be used to alleviate depigmentation of the hair shaft. In some embodiments, the oral supplement to the formulation can be used to induce pigmentation in the hair shaft. In some embodiments, the oral supplement to the formulation can be used to maintain pigmentation of the hair shaft. In some embodiments, the oral supplement to the formulation can be used to promote pigmentation of the hair shaft. In some embodiments, oral supplement to the formulation can be used to treat the thinning of hair shafts. In some embodiments, the oral supplement to the formulation can be used to treat the weakening of hair shafts. In some embodiments, the oral supplement to the formulation can be used to treat thinning hair. In some embodiments, oral supplement to the formulation can be used to treat loss of volume of hair.

In some embodiments, the oral supplement is used to help confer at least one beneficial hair care effect to hair head. However, the oral supplements may be used help promote hair care effects on any suitable hair. For example, in some embodiments, the oral supplement is used with the topical formulations disclosed herein to help treat facial hair. In some embodiments, the oral supplement can be used to treat body hair. In some embodiments, the oral supplement can be used to treat eyebrow hair, eyelash hair, mustache hair, cheek hair, beard hair, lower lip hair, goatee hair, whiskers, sideburns, ear hair, nose hair, or combinations thereof. In some embodiments, the oral supplement to the formulation can be used to treat head hair, neck hair, chest hair, shoulder hair, arm hair, axillary hair, hand hair, abdominal hair, back hair, pubic hair, gluteal hair, perineal hair, thigh hair, leg hair, foot hair, or combinations thereof.

In some embodiments, the oral supplement is administered orally with food. In some embodiments, the oral supplement is administered orally without food. In some embodiments, the oral supplement is administered in tablet form. In some embodiments, the oral supplement is administered in powder form. In some embodiments, the oral supplement is administered in liquid form.

In some embodiments, a subject administering one or more of the formulations described herein may observe a decrease in the amount of grey hair on the head or other body part. In some embodiments, the observed decrease is a decrease in the amount of grey hair by about 5%, about 10%, about 20%, about 30%, about 40%, about 50%, about 60%, about 70%, about 80%, or about 90%.

In some embodiments, a subject administering one or more of the formulations described herein may observe an increase in the total amount of hair on the head or other body part. In some embodiments, the observed increase is an increase of about 5%, about 10%, about 20%, about 30%, about 40%, about 50%, about 60%, about 70%, about 80%, or about 90%.

In some embodiments, a subject administering one or more of the formulations described herein may observe an increase in hair volume on the head or other body part. In some embodiments, the observed increase in hair volume is an increase of about 5%, about 10%, about 20%, about 30%, about 40%, about 50%, about 60%, about 70%, about 80%, or about 90%.

In some embodiments, a subject administering one or more of the formulations described herein may observe an increase in hair shine on the head or other body part. In some embodiments, the observed increase in hair shine is an increase of about 5%, about 10%, about 20%, about 30%, about 40%, about 50%, about 60%, about 70%, about 80%, or about 90%.

In some embodiments, a subject administering one or more of the formulations described herein may improve quality of life as assessed by the questionnaire provided herein. In some embodiments, the improvement is an increase of about 5%, about 10%, about 20%, about 30%, about 40%, about 50%, about 60%, about 70%, about 80%, or about 90%.

EXAMPLES

Example 1: Double-Blind Clinical Study of the Effects of Serum-Based Formulation and Oral Supplement A clinical study was designed to determine the effects of the formulation of the disclosure as well as the oral supplement on the hair pigmentation and hair growth of human subjects. The study is a Phase 2 randomized, double-blind study of Not Today Grey (NTG) oral supplement, as shown in Table 5, and To The Root (TTR) serum, as shown in Table 1B, vs. placebo in subjects with 5-10% grey hair at baseline. Subjects are randomized at baseline in a 1:1:1 ratio to receive either NTG and TTR, NTG and placebo TTR (PTTR), or placebo NTG (PNTG) and placebo TTR. Subjects have in-person visits every four weeks for 24 weeks after initiation of study drug administration and photographs are taken of a 4 cm² area of hair near the temple and of the entire head. A questionnaire designed to evaluate the global assessment of grey hair by the Investigator and Subject are administered at each visit. Treatment lasts 24 weeks. One post-study follow-up is performed by telephone two weeks after the last dose of study medication.

Treatment Regimen

NTG or PNTG is given orally (two tablets daily). TTR or PTTR is applied once per day directly to the scalp of the head hair. One pump of the serum covers a 2-inch area of the hair so typically 6-8 pumps is sufficient to cover the crown of the scalp including the areas being measured for the study. Participants massage the serum into their scalp on either wet or dry hair but do not shampoo their hair for at least 2 hours after use.

Study Evaluations

An evaluation is carried out with each subject visit. At visit 1, informed consent is sought and eligibility criteria, demographics, medical history, and concomitant medications are obtained. The number of hairs and grey hairs in the target areas will be counted, photographs of the target areas and the entire scalp are made, and questionnaires (overall subjective opinion, global assessment of grey hair by the subject and Investigator) are administered.

At visits 2 and 4 (week 6 and 18), the subject is contacted by telephone and asked about compliance with study medication, concomitant medications, and adverse events. Study drug administration continue.

At visit 3 (week 12), the subject is asked about compliance with study medication, concomitant medications, and adverse events. The number of hairs and grey hairs in the target area is counted, photographs of the target areas and the entire scalp are made, and questionnaires (overall subjective opinion, global assessment of grey hair by the subject and Investigator) are administered. Study drug administration continue.

At visit 5 (week 24), the subject is asked about compliance with study medication, concomitant medications, and adverse events. The number of hairs and grey hairs in the target area are counted, photographs of the target areas and the entire scalp are made, and questionnaires (overall subjective opinion, global assessment of grey hair by the subject and Investigator) are administered. Study drug administration cease and any remaining study drug are returned to the site.

At visit 6 (week 26), the subject is contacted by telephone and asked about concomitant medications, and adverse events.

Statistical Analysis

Descriptive and inferential statistical methods are used to summarize the data from this study. The term "descriptive statistics" refers to the number of subjects (n), mean, median, standard deviation (SD), standard error of the mean (SEM), minimum, and maximum for continuous variables; and refers to the number and/or percentage of subjects (or events) for categorical variables. The term "inferential statistics" refers to hypothesis tests which are performed to assess differences between the treated groups and the placebo group for the efficacy endpoints. All such hypothesis tests are tests of the null hypothesis of no difference between the treated group versus the two-sided alternative hypothesis that there is a difference. Unless stated otherwise, "treatment group" for summaries and analyses refers to the treatment the subject is randomly assigned to receive on Day 1 (NTG+TTR, NTG+PTTR, or PNTG+PTTR). The primary efficacy endpoint in this study is the mean change from baseline (Day 1) in the Target Area Grey Hair Count (TAGHC) at Week 24. Inferential statistics for comparisons of the treated groups versus the placebo group are calculated for this endpoint as well as for secondary efficacy endpoints. Nominal two-sided p-values (as well as 95% confidence intervals) are reported for all hypothesis tests, with p-values less than or equal to 0.05 being considered to represent a significant test result. Multiplicity is controlled by implementing a fixed testing procedure.

Sample Size Determination

Size determination of the treatment group may be calculated as follows. A sample size of 29 in each treatment group has 90% power to detect a difference in the mean change from baseline of 10.4 target area grey hairs (the difference between a placebo mean change of 0.4 and a treated mean change of −10) at Month 12, assuming that the common standard deviation is 12, using a two-group t-test with a 5% two-sided significance level. This sample size calculation assumes each group has a mean of 40 target area grey hairs at baseline. The projected placebo mean change from baseline of 0.4 corresponds to a 1% increase at Month 12 in the target area grey hair count. The projected treated group mean change from baseline of −10 corresponds to a 25% decrease at Month 12 in the target area grey hair count.

In other embodiments, the sample size of the study is based on the sponsor's recommendation.

Multiplicity

In order to control the family-wise error rate for the two treatment group comparisons to placebo for the primary endpoint (each performed at the nominal $\alpha=0.05$ level of significance), a fixed-sequence testing procedure is used. The first hypothesis to be tested in this fixed sequence is whether there is a significant difference between NTG+TTR and PNTG+PTTR for the primary efficacy endpoint. If this analysis yields a significant result, the statistical significance of the NTG+PTTR vs. PNTG+PTTR comparison is assessed.

Primary Analysis

The primary endpoint is the change from baseline in the TAGHC at Week 24. The primary analysis of this endpoint is a Mixed-effect model repeated measures (MMRM) analysis, which includes the changes from baseline at Weeks 4, 8, 12, 16, 20 and 24 and is based on the FAS. The model includes the baseline TAGHC as a covariate, with treatment group (NTG+TTR, NTG+PTTR, and PNTG+PTTR), and visit (Weeks 4, 8, 12, 16, 20 and 24) as fixed effects, and subject as a random effect. Treatment group comparisons for each treatment group vs. PNTG+PTTR at each visit (ie, Weeks 4, 8, 12, 16, 20 and 24) is performed by constructing linear contrasts for differences between treatment group least-squares (LS) means. Nominal two-sided p-values for testing the significance of these differences and associated 95% confidence intervals is reported in summary tables. Note that the treatment group comparisons at Weeks 4, 8, 12, 16, and 20 are considered to be exploratory in nature. A supportive analysis using the MMRM model is performed with the PPAS. The MMRM analysis is implemented with the PROC MIXED procedure of SAS®, using the restricted maximum likelihood method and an unstructured within-subject covariance matrix. In the event that convergence is not obtained with the unstructured covariance matrix, the model is re-run using variance components, autoregressive, compound symmetry, and Toeplitz covariance structures. The model resulting in the lowest Akaike's information criteria is selected for the analysis.

Descriptive statistics of the TAGHC at each visit, as well as the change from baseline, by treatment group is presented for both the FAS and PPAS. Graphical displays of the TAGHC mean change from baseline by treatment group is provided for both analysis sets.

Example 2: Clinical Study Protocol: A Phase 2, Randomized, Double-Blind, Placebo-Controlled, Single-Center Study of the Effects of an Oral Supplement and Topical Serum on the Appearance of Grey Hair The above study described in Example 1, is described in further detail below, and was carried out by an independent party according to the following instructions.

Study Summary

| | |
|---|---|
| Methodology | Double blind, randomized, placebo-controlled |
| Study Duration | 26 weeks |
| Study Center(s) | Single-center |
| Objectives | To assess the efficacy of Not Today Grey (NTG) oral supplement as shown in Table 5, and To The Root (TTR) serum as shown in Table 1B, vs. placebo.<br>Primary:<br>Clinical Assessment of Number of Grey Hairs<br>Secondary:<br>Photograph Grading of Efficacy (hair density).<br>Investigator Global Assessment (IGA) of Standardized Photographs (changes in amount of grey hair, total amount of hair, overall hair change (volume and shine), and overall improvement)<br>Subject global assessment (changes in amount of grey hair and overall hair number, texture, shine, strength, and softness<br>Subject Quality of Life questionnaire (including hair thinning inquiries)<br>To assess the safety of NTG and TTR based on reported Adverse Events. |
| Number of Subjects | 80 to complete as follows:<br>27 subjects in cell 1 (NTG and TTR)<br>27 in cell 2 (NTG and placebo TTR)<br>26 in cell 3 (placebo NTG and placebo TTR) |
| Diagnosis and Main Inclusion Criteria | Limited grey hairs. Subjects will be healthy males or females who have score of 2-6 (on a 1-7 scale, where 1 = 1 to 5 grey hairs/cm$^2$ and 7 = 30 or more grey hairs/cm$^2$) in a 4 cm$^2$ Clinical Count Area on the crown/top of head, and with grey hair covering ≤25% of the overall head. |
| Study Product, Dose, Route, Regimen | NTG, 2 tablets orally once per day. Two pumps of TTR or PTTR will be applied twice per day (morning and evening) directly to the Target Area of scalp on either wet or dry hair. Two pumps of the serum should cover the 36 cm$^2$ test area; up to an additional 2 pumps may be administered twice a day to spot-treat other areas of grey (maximum 8 pumps per day). |
| Duration of administration | 24 weeks |
| Reference therapy | Placebo for NTG and TTR |
| Statistical Methodology | All primary and secondary endpoints will be summarized descriptively and analyzed using FAS and PPAS. Mixed model will be applied to Clinical Assessment of Number of Grey Hairs and photo grading parameters for change from baseline and treatment comparisons. IGA and SGA responses will be compared to the constant of 0 to test the change from baseline. |

Greying of hair, also called canities or achromotrichia, is part of the natural aging process. It has been reported that worldwide 74% of men and women between the ages of 45-65 have grey hair. Greying typically begins in the mid-30s for Caucasians, the late-30s for Asians, and the mid-40s for Africans. Premature hair greying is considered when the onset of grey hair begins before the age of 20 years in Caucasians, before the age of 25 years in Asians, and before the age of 30 years in Africans.

In men, grey hair typically begins at the temples and sideburns, then spreads to the vertex and lastly the occiput. In women, greying develops at the boundaries of the scalp and moves towards the vertex. Progression of hair greying depends in part on genetic factors; however, early onset of grey hair does not necessarily correlate with rapid progression.

The test supplement (NTG) is a daily supplement (shown in Table 5), intended to slow greying of hair in those individuals who have minimal-moderate numbers of grey hair. NTG (2 capsules) contains Vitamin D3 (25 mcg), Vitamin B6 (10 mg), Folate (as 400 mg folic acid), Vitamin B12 (as methylcobalamin 6 mcg), Biotin (300 mcg), Pantothenic Acid (200 mg), Calcium (as calcium carbonate 300 mg), Iron (9 mg), Selenium (as selenomethionine 55 mcg), Copper (2 mg), Para-Aminobenzoic Acid (300 mg), *Polygonum multiflorum* (10 mg) and Black Sesame Seed Extract (25 mg).

The test serum (TTR) (shown in Table 1B), contains Water (Aqua), Glycerin, Palmitoyl Tetrapeptide 20 Amide (2%), *Citrus reticulata* (Tangerine) Extract (2%), *Polygonum multiflorum* (Fo-Ti) Root Extract, Sesame Indicum Extract, Biotin, *Zanthoxylum bungeanum* Fruit Extract, *Panax Ginseng* Root Extract, *Humulus lupulus* (Hops) Flower Extract, Panthenol, *Glycine Soja* (Soybean) Germ Extract, Hydrolyzed Barley Protein, Wasabi *Japonica* Leaf Extract, Caffeine, *Coffea Arabica* (Coffee) Seed Extract, 1,2-Hexanediol, Butylene Glycol, Hydroxyethylcellulose, Acetyl Tyrosine Pentylene, Gluconolactone, Sodium Benzoate.

Study Design

This study is a Phase 2 randomized, double-blind study of NTG and TTR vs. placebo in subjects with score of 2-6 (on a 1-7 scale, where 1=1 to 5 grey hairs/cm$^2$ and 7=30 or more grey hairs/cm$^2$) for grey hair on a 4 cm$^2$ Clinical Count Area near the crown/top of the head at baseline and grey hair on ≤25% of all scalp hair. Subjects are randomized at baseline in a 1:1:1 ratio to receive either NTG and TTR, NTG and placebo TTR (PTTR), or placebo NTG (PNTG) and placebo TTR. Subjects have in-person visits at weeks 12 and 24 weeks after initiation of study treatment administration at the baseline visit. At each visit, photographs are taken of a 36 cm$^2$ area of hair near the crown/top of head. The Investigator performs an Investigator Global Assessment (IGA) (changes in amount of grey hair, total amount of hair, overall hair change (volume and shine), and overall improvement) on photographs taken at weeks 12 and 24. The Investigator or designee also performs a clinical assessment of number of grey hairs on the Clinical Count Area at each visit. Additionally, the Investigator or designee evaluates photographs from baseline and weeks 12 and 24 for hair density. At each in-person visit, subjects complete a Quality of Life Questionnaire and at weeks 12 and 24, subjects complete a Subject Global Assessment of hair. Compliance checks are performed by telephone or email at Weeks 6 and 18 to remind subjects about study procedures and to record any adverse events.

Treatment lasts 24 weeks. One post-study follow-up is performed by telephone or e-mail two weeks after the last dose of test products.

Subject Criteria

At least 95 subjects are enrolled to complete with 80 subjects at two study sites in the United States (SGS North America, Inc), including 27 subjects in cell 1, 27 subjects in cell 2, and 26 subjects in cell 3. Subjects are eligible if they meet all of the following inclusion criteria and none of the exclusion criteria.

To be eligible for this study, each of the following criteria must be satisfied with a "YES" answer (unless not applicable):

1. Male or female aged 18 to 60 years, inclusive.
2. Has grey hair score 2-6 on 1-7 scale (where 1=1 to 5 grey hairs/cm$^2$ and 7=30 or more grey hairs/cm$^2$) in a 4 cm$^2$ Clinical Count Area at the crown/top of head or right temple area (refer to Appendix 21.6), with grey hair covering ≤25% of the overall head.
3. Hair color medium brown to darkest black.
4. Females of childbearing potential [i.e., not surgically sterile and/or not post-menopausal (≥12 months since last menstrual period without an alternative medical cause)] must have a negative urine pregnancy test at Baseline. Women of childbearing potential who are not abstinent from sex with male partners must use highly effective methods of contraception for the duration of the study including: established use of oral, injected, or implanted hormonal methods of contraception (at least 3 months); double barrier (e.g., condom plus spermicide), placement of an intrauterine device or intrauterine system, bilateral tubal ligation or partner bilateral tubal ligation, vasectomy or partner vasectomy. Female subjects of childbearing potential must also refrain from egg donation or retrieval for the duration of the study.
5. Individuals must not have dyed the hair for at least 1 month prior to screening/baseline and must agree to refrain from dyeing the hair in the target area(s) of interest until after the final study visit.
6. Willing to maintain the same hair style and continue using regularly used hair cleansing products (shampoo and/or conditioner) throughout the study.
7. Willing to refrain from using any topical hair products or treatments on the hair that could affect hair properties (e.g., heat treatments, medicated shampoo, etc.) for the duration of the study except for the test material (if applicable) and regular shampoo and/or conditioner and styling products.
8. Willing to refrain from taking any vitamins, minerals, or herbal supplements with claims related to hair growth or benefits during the study, and to not start taking any new vitamins, minerals, or supplements of any kind during the study.
9. Willing to comply with the protocol, attend all study visits, and report any changes in health status or medications, AE symptoms, or reactions immediately.
10. Willing and able to provide written informed consent, including agreement to privacy language compliant with country and/or local requirements, after the scope and nature of the investigation have been explained, and before the initiation of any study-related procedures.
11. Willing to wear provided headband and black drape over clothing for study photography.
12. Willing to sign a photography release.

To be eligible for this study, each of the following criteria must be satisfied with a "NO" answer: (unless not applicable):

1. Having a medical history of any condition that results in grey hair (for example: nutritional deficiencies such as Vitamin B12, iron, and copper deficiency, severe protein malnutrition, cystic fibrosis, celiac disease, hyperthyroidism/hypothyroidism, vitiligo, alopecia areata, and genetic diseases such as Werner syndrome, Louis-Bar syndrome, Waardenburg syndrome, or Griscelli syndrome).
2. Having a medical history of any condition that results in hair darkening (for example: Addison's disease, neurodermatitis, porphyria cutanea tarda, and inflammatory scalp conditions).
3. Currently receiving iron injections.
4. Having severe or untreated depression or anxiety that, in the Investigator's opinion, would likely reduce the safety of study participation. Antidepressant and anti-anxiety medications are allowed only if they have been administered at stable dose and frequency for ≥1 month prior to Screening with the expectation that the stable daily dose will continue for the duration of the study.
5. Having a history of immunosuppression/immune deficiency disorders (including HIV infection, AIDS, multiple sclerosis, Crohn's disease, rheumatoid arthritis), organ transplant (heart, kidney, etc), or currently using oral or systemic immunosuppressive medications and biologics (eg, azathioprine, belimumab, Cimzia®, Cosentyx®, cyclophosphamide, cyclosporine, Enbrel®, Humira®, Imuran®, Kineret®, mycophenolate mofetil, methotrexate, Orencia®, prednisone, Remicade®, Rituxan®, Silig™, Simponi®, Stelara®, Taltz®) and/or undergoing radiation or chemotherapy as determined by study documentation.
6. Having been advised by a doctor to not take iron supplements due to medication interactions.
7. Pregnant, lactating, or undergoing fertility treatment.
8. Males with a pregnant partner
9. Currently a smoker or having smoked regularly in the past 6 months.
10. Having a history of serious substance abuse (e.g., cocaine, heroin) within 6 months prior to Screening.
11. Having a disease such as asthma, diabetes, epilepsy, hypertension, hyperthyroidism, or hypothyroidism that is not controlled by diet or medication. Individuals having multiple health conditions may be excluded from participation even if the conditions are controlled by diet, medication, etc.
12. Having started a long-term medication within the last 2 months.
13. Having any planned surgeries or invasive medical procedures during the study. Noninvasive medical procedures or surgeries will be reviewed for their impact on the study outcome and acceptability by the Investigator or designee.
14. Currently participating in any other clinical trial at SGS or another research facility or doctor's office.
15. Having used an investigational drug or device within 30 days prior to Screening.

16. Having started any new vitamin, mineral, or herbal supplement within 30 days prior to screening
17. Taking (or not willing to stop taking) any vitamin, mineral, or herbal supplement which, if combined with NTG, would result in an intake that exceeds the tolerable upper intake level for the ingredient, as determined by the Investigator or designee during screening at baseline.
18. Having other clinically significant illness, medical condition or medical history at Screening or Baseline that, in the Investigator's opinion, would likely reduce the safety of study participation or compliance with study procedures.
19. Subject has an allergy or intolerance to sesame and/or any other ingredient of NTG or TTR.
20. Females having started hormone replacement therapies (HRT) or hormones for birth control less than 3 months prior to study entry or who plan on starting, stopping, or changing doses of HRT or hormones for birth control during the study.
21. Males having started prescription testosterone therapy less than 3 months prior to study entry or planning on starting, stopping, or changing doses of testosterone therapy during the study (e.g., testosterone cypionate, testosterone enanthate, testosterone pellet, testosterone undecanoate) or on a testosterone booster or prescription testosterone (eg, DHEA, Omnadren®, Sustanon®, testosterone cypionate, testosterone enanthate, testosterone propionate, testosterone phenylpropionate, tribulus).

Prior to the start of the study, prospective subjects are screened for eligibility requirements through use of an IRB-approved script. Prospective subjects are informed of the pre-visit procedures and are assigned an appointment time for visiting the clinic.

Prospective subjects are given an IRB-approved ICF to read and sign. They have all their study-related questions answered by the Investigator or designated staff, and if they agree, sign the ICF. They are given a copy of the signed ICF, and the original signed ICF is kept in the study file.

Prospective subjects who sign the ICF are assigned a screening number, acclimate to clinic conditions, and are screened for qualification criteria. Those who meet eligibility criteria are enrolled in the study and assigned a subject number according to the predetermined randomization.

Randomization and Blinding

Daily doses of NTG administered orally and daily doses of TTR serum administered topically to the hair of the scalp are planned to be tested in this study. Enrolled subjects are assigned randomly to either NTG and TTR, NTG and PTTR, or PNTG and PTTR in a 1:1:1 allocation ratio, based upon a computer-generated randomization schedule.

At the Baseline visit (Visit 1), subjects signing the informed consent are assigned a sequential subject identification number by the site. Prospective subjects are assigned a 3-character screening number and enrolled subjects are assigned a 3-digit subject number both of which, when used in conjunction with the clinical study number, uniquely identify every subject on the study. Once assigned, the subject identification numbers are re-assigned and should not be changed. These numbers are used to identify the subject throughout the study, including the Screening period. Subjects are considered enrolled into the study once they are randomized and assigned a subject number.

After a prospective subject has met all prerequisites for randomization on Day 1 (Baseline/Visit 1), the study site executes the randomization. Subjects are considered enrolled into the study once they are randomized.

Subjects are randomized in a 1:1:1 ratio (cell 1: NTG plus TTR; cell 2: NTG plus PTTR; or cell 3: PNTG+PTTR) of treatment groups using a block size of 3. Test materials are dispensed based on the treatment assignment.

Prior to the start of the study, SGS generates a randomization list to establish treatment assignment to 1 of the treatment cells (cell 1, cell 2, or cell 3). The list is first created by concatenating blocks of size of 3 subjects: 1 for cell 1, 1 for cell 2 and 1 for cell 3. The list is randomized by variables from 2 independent uniform distributions: one to randomize subjects within a block and one to randomize blocks. After the randomization list is created, treatment is assigned to each subject number accordingly.

The study is double-blinded. The following blinding procedures are followed to maintain the double-blinded nature of this study:

The study products are dispensed/administered by clinic personnel other than the evaluator(s). Additionally, staff in charge of study product dispensation/administration and subjects are instructed not to discuss study products with the Investigator or other evaluator(s).

The randomization list is secured in a cabinet and/or computer file accessible to a data committee consisting of selected representatives from clinical services, quality assurance, and the statistical department of SGS.

Subjects are blinded to treatment assignment.

The blind should be broken for site personnel only if knowing the subject's treatment allocation would facilitate specific medical treatment. In all cases, the Investigator should consult with the medical monitor prior to unblinding, if possible, and must contact the medical monitor as soon as it is practical after unblinding has occurred and treatment initiated.

If the blind is broken, the subject will continue to be followed and evaluated per-protocol. The date, time, and reason for the unblinding must be documented on the appropriate page of the eCRF.

The randomization schedule or blocking factor(s) will not be revealed to study subjects, Investigators, clinical staff, site managers or the Sponsor until all subjects have completed the study and the database has been finalized by the Sponsor.

Dosage and Administration

NTG, TTR, PNTG or PTTR is provided in individual Investigational Product Kits. Test materials are to be stored at 50-80° F. until use.

NTG, 2 tablets orally once per day in the morning with food. If a dose is missed, take it in the evening. Do not take two doses in any calendar day (midnight to midnight). Two pumps of TTR or PTTR are applied twice per day directly to the test area of scalp on either wet or dry hair. Two pumps of the serum should cover the 36 $cm^2$ test area; up to an additional 2 pumps may be administered twice a day to spot treat other areas of grey (maximum of 8 pumps per day).

Participants should massage the serum into their scalp but should not shampoo their hair for at least 2 hours after use.

The site will maintain a log of all investigational product received, dispensed, and returned. Investigational product supplies for each subject are inventoried and accounted for in the study.

Each subject is given a diary to complete, documenting compliance with study treatments. Diaries are reviewed for compliance at each post-baseline visit. Test materials are visually inspected at each post-baseline study visit to evaluate treatment compliance.

Additionally, test material units are weighed prior to distribution and at each post-baseline visit. Subjects are instructed to return their test materials and daily diary at each post-baseline visit. If subjects do not return their diary or test materials during the study, a verbal confirmation is obtained for usage compliance and it is documented as a note to file.

Any suspected noncompliance with the treatment or study instructions (missing applications, not following usage instructions, etc.) is addressed by the Investigator or designee. The Investigator will determine whether a subject's noncompliance will affect the study outcome and whether the subject should be discontinued and/or data should be excluded from statistical analyses.

Use of all concomitant medications is recorded in the subject's eCRF. This will include all prescription drugs and over-the-counter medications taken within 30 days before screening at baseline, which is considered prior therapy.

At the discretion of the Investigator, any medication deemed necessary for the welfare of the subject may be continued at stable doses during the study, except for those medications listed. Any changes in concomitant medications are recorded in the subject's eCRF.

The following therapies are prohibited during the study:
Vitamin, minerals, or herbal supplements with claims related to hair growth or that would lead to consumption over the tolerable upper intake level of any ingredients (Refer to Appendix 21.7).
Other investigational drug(s) or device(s)
Topical products to the hair of the scalp other than common shampoos and conditioners Use of any of these prohibited therapies is considered a protocol deviation.

The following instructions are given to the subject:
Apply 2 pumps of serum directly to the test area of scalp on either wet or dry hair twice per day. Two pumps of the serum should cover the 6 cm² test area. Up to an additional 2 pumps may be administered twice a day to spot treat other areas of grey (maximum 8 pumps per day).
Massage the serum into your scalp but do not wash your hair for at least 2 hours after serum application.
Oral supplement: Take 2 tablets orally once per day in the morning with food. Do not take 2 tablets in any calendar day (midnight to midnight).
Keep out of reach of children.
For study visits, the following instructions are given:
Wash hair within 24 hours before study visit. Come to the clinic with dry hair and no other hair products in hair (except for the test material as long as hair will have sufficient time to dry before the visit. You may blow dry your hair after applying the serum, but please wait at least 10 minutes after application to blow dry hair.
The test material should be applied as scheduled in the evening of the day prior to each post-baseline clinic visit. You may apply the product the day of the visit before the visit if your hair is dry in time for the visit.
Bring your test material(s) (including empty containers) and diary with you to each study visit. Do not throw away empty containers.
General instructions for subjects:
Avoid extended periods of sun exposure and use of all tanning beds for the duration of the study. Extra care should be taken to wear a hat and avoid sun exposure from 10 AM to 3 PM.
Use the assigned test materials as instructed.
Refrain from any chemical processing on your hair, including dye, color, highlighting, relaxer, permanent waves, etc.
Refrain from changing any of your hair cleansing, conditioning, or styling products.
Maintain the same hairstyle throughout the study.
Do not begin the use of new hair products during the study.
Do not take any vitamins, minerals, or herbal supplements with claims related to hair growth or benefits during the study, and to not start taking any new vitamins, minerals, or supplements of any kind.

Prior to participating in procedures at each study visit, subjects will acclimate to ambient conditions within the clinic for at least 15 minutes. The designated rooms are maintained at a temperature of 68-75° F. and the relative humidity will range from 35%-65%. The temperature and humidity of the designated waiting and/or instrumentation rooms are recorded hourly during applicable study visits. Standardized global photographs will not be taken at Baseline, Week 12 or Week 24 for subjects enrolled in the Phoenix facility. Photograph Grading of Efficacy will not be performed for any of the subjects enrolled in Phoenix.

Screening/Baseline Visit 1

Prospective subjects are given an IRB-approved Informed Consent Form. They will have all their study-related questions answered by the Investigator or designated staff, and if they agree, they will sign the ICF. They are given a copy of the signed ICF, and the original signed ICF is kept in the study file.

Prospective subjects who sign the ICF are assigned a screening number and will acclimate to clinic conditions. Prospective subjects are screened for qualification criteria including UPT. Demographics, medical history, and concomitant medications are obtained.

Those who meet eligibility requirements are enrolled into the study and assigned a subject number.

The Investigator or designee will determine the Clinical Count Area for each subject (2 cm×2 cm; (4 cm² on the crown/top of head) within a 6 cm×6 cm target area on crown of head. Appendix 21.6. Each subject's Clinical Count Area and target area are documented on a diagram.

Subjects will participate in the following procedures:
Clinical Assessment of Number of Grey Hairs
Standardized Global Photographs
Subject Quality of Life Questionnaire (QOL)
Subjects are provided with preweighed and/or precounted units of the test materials, and oral and written usage instructions.
Subjects are provided with a calendar of study visits, study instructions as described, and a daily diary to record test material applications and comments.

Compliance Checks

At Weeks 6 and 18, clinic staff will contact each subject by telephone or email to ask about compliance with study medication, concomitant medications, and adverse events. Study treatment administration will continue.

Interim Visit (Week 12)

A clinician will record concomitant medications and will ask subjects if they have experienced any changes in their health since the previous visit. If an AE is reported, the Investigator is informed, and an AE form is completed.

Daily diaries are collected and reviewed for AEs and compliance. If an AE is reported, the Investigator is informed, an AE form is completed, and AE reporting procedures are followed. Subjects who are noncompliant are counseled that if they continue to be noncompliant, they are to be discontinued from the study. Diaries are retained by the testing facility and new diaries are distributed to the subjects.

Test materials are visually inspected and weighed or counted to verify usage compliance. Test material units are returned to the subjects or new units distributed if needed.

Subjects will acclimate to clinic conditions. Upon acclimation, subjects will participate in the following procedures:
  Clinical Assessment of Number of Grey Hairs
  Standardized Global Photographs
  Subject Global Assessment (SGA)
  Subject Quality of Life Questionnaire (QOL)
Final Visit: Visit 3 (Week 24±3 Days)

A clinician will record concomitant medications and will ask subjects if they have experienced any changes in their health since the previous visit. If an AE is reported, the Investigator is informed, and an AE form is completed.

Daily diaries are collected and reviewed for AEs and compliance. If an AE is reported, the Investigator is informed, an AE form is completed, and AE reporting procedures are followed. Subjects who are noncompliant are counseled that if they continue to be noncompliant, they are to be discontinued from the study. Diaries are retained by the testing facility and new diaries are distributed to the subjects.

Test materials are visually inspected and weighed or counted to verify usage compliance. Test material units are retained by the clinic.

Subjects will participate in the following procedures:
  Clinical Assessment of Number of Grey Hairs
  Standardized Global Photographs
  Subject Global Assessment (SGA)
  Subject Quality of Life Questionnaire (QOL)

After the completion of the study or study visits, the Investigator or designee will perform the following assessments:
  Photograph Grading of Efficacy using photographs from baseline and weeks 12 and 24
  Investigator Global Assessment (IGA) of Standardized Photographs using photographs from weeks 12 and 24
Follow-Up Check At Week 26 (±3 days), clinic staff will contact each subject by telephone or email to ask about concomitant medications, and adverse events.

Medical History and Demographics

The medical history is obtained from medical records and/or via subject interview at the Baseline visit, and includes general medical history and medication history.

Medical history, conditions, and procedures that occurred prior to Baseline may be added throughout the study (if identified later).

Demographic information will also be obtained at the Baseline visit and will include: age; sex; race, ethnicity.

Hair Evaluations

Note that the order of the assessments listed below may be altered from the order indicated in the study visits to help study flow, or at the recommendations of the Sponsor or Investigator. Any change in the order of procedures will not compromise study data.

Clinical Assessment of Number of Grey Hairs

The expert grader will assess each subject's number of grey hairs on the Clinical Count Area at baseline and weeks 12 and 24. The same grader will grade the same subject at each time point.

The Clinical Count Area, determined by the Investigator or designee, is a 2 cm×2 cm (4 cm$^2$) area on the crown/top of head, within the Target Area shown in Appendix 21.6. The locations of the target grey area and clinical count area are documented on a diagram at baseline (measured from front hairline) for each subject to ensure that subsequent assessments are performed on the same location.

Using a cutout template to delineate the Clinical Count Area, the expert grader will assess the number of grey hairs using the following scale (only whole numbers allowed). The grader will perform a duplicate count to ensure accuracy. Entire Clinical Count Area is graded overall (1 score given).

Number of gray hairs per Clinical Count Area is graded according to the following scale:
  7=30 or more grey hairs/cm$^2$
  6=25 or more grey hairs/cm$^2$
  5=21-25 grey hairs/cm$^2$
  4=16-20 grey hairs/cm$^2$
  3=11-15 grey hairs/cm$^2$
  2=6-10 grey hairs/cm$^2$
  1=1-5 grey hairs/cm$^2$
Standardized Global Photographs Photographs are taken of the target area for grey hair (6 cm×6 cm [36 cm$^2$] area on the crown top of head; refer to Appendix 21.6) at baseline and weeks 12 and 24.

A total of 2 images are taken of each subject at each time point.

Prior to photography, each subject's hair is parted down the center (front to back) and combed (as needed). Each subject's head is positioned (on a head stand [with chin rest and forehead rest] if possible) at an angle of 60° to capture hair color with top of scalp toward the camera at fixed distance. Positioning is repeated at each post-baseline time point.

One additional photo is taken at an angle of 0°. For those that qualify with grey hair count on the right temple area the subject's hair is parted down the temple and combed (as needed). Each subject's head is positioned (on a head stand [with chin rest and forehead rest] if possible at an angle of 60° to the side toward the camera at fixed distance. Positioning is repeated at each post-baseline point.

Photography is performed using the Canfield Hair Rig Imaging System (Canfield Imaging Systems, Fairfield, New Jersey) with a Canon EOS 7D DSLR camera with 28-75 mm lens under visible lighting using Canfield IntelliFlash lighting system affixed to the photo station. A color standard is affixed to the forehead rest and is included in each photograph.

At each photography visit, a color standard (CasMatch Color Mire chip from Bear Medic Corporation) is photographed prior to beginning each day's photography.

Photograph Grading of Efficacy

The Investigator or designee will grade photographs taken at baseline and weeks 12 and 24.

Hair density is graded according to the following scale. Entire target area is graded overall (1 score given).
  1=baldness
  2=very low hair density
  3=low hair density
  4=medium hair density
  5=high hair density
  6=very high hair density
Investigator Global Assessment (IGA) of Standardized Photographs The Investigator will perform the Investigator Global Assessment (IGA), rating changes in subject's hair on the target area, using photographs taken at weeks 12 and 24. Refer to Attachment 21.1 Investigator Global Assessment.

Subject Global Assessment (SGA)

Subjects will provide a rating of his or her hair (focusing on the target area) at weeks 12 and 24. Refer to Attachment 21.2 Subject Global Assessment Subject Quality of Life Questionnaire (QOL)

Subjects will complete the Quality of Life (QOL) questionnaire at baseline and weeks 12 and 24. The QOL is a 15-item questionnaire designed to explore the effect of grey hair upon the subject's appearance and self-consciousness, beliefs about thinning hair and sense of well-being. Refer to Attachment 21.3 Quality of Life Questionnaire.

Statistical Plan

General Statistical Procedures

Descriptive and inferential statistical methods are used to summarize the data from this study. The term "descriptive statistics" refers to the number of subjects (n), mean, median, standard deviation (SD), standard error of the mean (SEM), minimum, and maximum for continuous variables; and refers to the number and/or percentage of subjects (or events) for categorical variables. The term "inferential statistics" refers to hypothesis tests which are performed to assess differences between the treated groups and the placebo group for the efficacy endpoints. All such hypothesis tests are tests of the null hypothesis of no difference between the treated group versus the two-sided alternative hypothesis that there is a difference. Unless stated otherwise, "treatment group" or "cell" for summaries and analyses refers to the treatment the subject is randomly assigned to receive on Day 1 (cell 1: NTG+TTR, cell 2: NTG+PTTR, or cell 3: PNTG+PTTR). The primary efficacy endpoint in this study is the mean change from baseline (Day 1) in the grey hair count at Week 24. Inferential statistics for comparisons of the treated groups versus the placebo group are calculated for this endpoint as well as for secondary efficacy endpoints. Nominal two-sided p-values (as well as 95% confidence intervals) will be reported for all hypothesis tests, with p-values less than or equal to 0.05 being considered to represent a significant test result. Multiplicity is controlled by implementing a fixed testing procedure.

Multiplicity

In order to control the family-wise error rate for the 2 treatment group comparisons to placebo for the primary endpoint (each performed at the nominal $\alpha=0.05$ level of significance), a fixed-sequence testing procedure is used. The first hypothesis to be tested in this fixed sequence is whether there is a significant difference between cell 1 (NTG+TTR) and cell 3 (PNTG+PTTR) for the primary efficacy endpoint. If this analysis yields a significant result, the statistical significance of the cell 2 (NTG+PTTR) vs. cell 3 (PNTG+PTTR) and cell 1 vs. cell 2 comparisons is assessed.

Primary Analysis

The primary endpoint is the change from baseline in the Clinical Assessment of Number of Grey Hair (CANGH) at Week 24. The primary analysis of this endpoint is a Mixed-effect model repeated measures (MMRM) analysis, which includes the changes from baseline at Weeks 12 and 24 as outcomes and is based on the FAS. Analysis will also be performed using the PPAS. The model will include the baseline CANGH as a covariate, with treatment group (NTG+TTR [cell 1], NTG+PTTR [cell 2], and PNTG+PTTR [cell 3]), and visit (Weeks 12 and 24) as fixed effects, and subject as a random effect. Treatment group comparisons for each treatment group vs. PNTG+PTTR at each post-baseline time point (ie, Weeks 12 and 24) are performed by constructing linear contrasts for differences between treatment group least-squares (LS) means. Nominal two-sided p-values for testing the significance of these differences and associated 95% confidence intervals are reported in summary tables. If the mixed model doesn't converge, then Wilcoxon rank sum test is used to compare the treatments in terms of change from baseline at each post-baseline timepoint. Note that the treatment group comparisons at Week 12 are considered to be exploratory in nature. A supportive analysis using the MMRM model is performed with the PPAS. The MMRM analysis is implemented with the PROC MIXED procedure of SAS®, using the restricted maximum likelihood method and an unstructured within-subject covariance matrix. In the event that convergence is not obtained with the unstructured covariance matrix, the model is re-run using variance components, autoregressive, compound symmetry, and Toeplitz covariance structures. The model resulting in the lowest Akaike's information criteria is selected for the analysis.

Descriptive statistics of the CANGH at each visit, as well as the change from baseline, by treatment group are presented for FAS. Graphical displays of the CANGH mean change from baseline by treatment group are provided for FAS.

Secondary Analyses

Photograph Grading of Efficacy (PGE)

The change from baseline in the PGE at Weeks 12 and 24 are secondary efficacy endpoints. These endpoints are analyzed using the FAS and the PPAS, incorporating the PGE at Weeks 12 and 24. The same statistical model are used for this analysis and will include the baseline PGE as the covariate. If the mixed model doesn't converge, then Wilcoxon rank sum test are used to compare the treatments in terms of change from baseline at each post-baseline timepoint. Note that the treatment group comparisons at Week 12 are considered to be exploratory in nature.

Descriptive statistics of the PGE at each visit, as well as the change from baseline, by treatment group are presented for the FAS. Graphical displays of the PGE mean change from baseline by treatment group are provided for FAS.

IGA of Standardized Photographs

The IGA for grey hair amount, total amount of hair, overall hair change (volume and shine), and overall improvement at Weeks 12 and 24 are secondary efficacy endpoints. Refer to Attachment 21.1 Investigator Global Assessment.

An analysis of the IGA scores for questions at Weeks 12 and 24 are performed on the FAS and the PPAS by comparing the scores to the constant of 0 using sign test, testing the null hypothesis that there is no change observed in the hair since the baseline visit.

Descriptive statistics (including both categorical variable statistics [using response categories] and continuous variable statistics [using numerical scores]) are presented by treatment group for both IGA questions at all visits using the FAS.

Subject Global Assessment (SGA)

The subject global assessment for changes in grey hair amount and overall hair number, texture, shine, strength, and softness at Weeks 12 and 24 are secondary efficacy endpoints. Refer to Attachment 21.2 Subject Global Assessment.

An analysis of the SGA scores for each question at Weeks 12 and 24 are performed on the FAS and PPAS by comparing the scores to the constant of 0 using sign test, testing the null hypothesis that there is no change observed in the hair since the baseline visit.

Descriptive statistics (including both categorical variable statistics [using response categories] and continuous variable statistics [using numerical scores]) are presented by treatment group for all SGA questions at all visits using the FAS.

Quality of Life Questionnaire (QOL)

The QOL is a 15-item questionnaire designed to explore the effect of grey hair upon the subject's appearance and self-consciousness, beliefs about thinning hair and sense of well-being. Refer to Attachment 21.3 Quality of Life Questionnaire Descriptive statistics for the response categories are presented by treatment group for each QOL question at all visits using the FAS and PPAS.

Investigational Product Information

The following products are used during the study by subjects in the indicated cell(s):

| Cell(s) | Product Name | Product Type | Product ID | Marketed or Investigational | Study Code |
|---------|--------------|--------------|------------|------------------------------|------------|
| 1, 2    | NTG          | Capsules     | 0300E2 EXP April 2024 | Marketed | Product A |
| 3       | PNTG         | Capsules     | NA         | NA (Placebo)                 | Product B  |
| 1       | TTR          | Serum        | 201-112-11 July 18, 2022 | Investigational | Product C |
| 2, 3    | PTTR         | Serum        | 201-112-11 July 18, 2022 | NA (Placebo) | Product D |

Physical Description of Investigational Products

NTG is a vitamin/mineral/herbal supplement that contains 125% of the Daily Value of Vitamin D3, 588% of the Daily Value of Vitamin B6, 166% of the Daily Value of folate, 250% of the Daily Value of Vitamin B12, 1000% of the Daily Value of biotin, 4000% of the Daily Value of pantothenic acid, 23% of the Daily Value of calcium, 50% of the Daily Value of iron, 100% of the Daily Value of selenium, and 222% of the Daily Value of copper. All of these are given in amounts that are under the tolerable upper intake level according to the National Institute of Health (Office of Dietary Supplements) Fact Sheets for Health Professionals.

NTG also contains Para-Aminobenzoic Acid 300 mg and 25 mg Black Sesame Extract and 10 mg of Fo-Ti root. No significant health risks are anticipated with any of these ingredients.

The main ingredients of TTR is Palmitoyl Tetrapeptide 20 Amide (2%) and *Citrus Reticulata* (Tangerine) Extract (2%). No significant health risks are anticipated with either of these ingredients.

Directions for Use

NTG, 2 tablets orally once per day in the morning with food. Two pumps of TTR or PTTR are applied twice per day directly to the test area of scalp on either wet or dry hair. Two pumps of the serum should cover the 36 cm$^2$ test area; up to an additional 2 pumps may be administered twice a day to spot treat other areas of grey (maximum of 8 pumps per day). Participants should massage the serum into their scalp but should not shampoo their hair for at least 2 hours after use.

Investigator Global Assessment of Standardized Photographs (Protocol Attachment 21.1)

What changes have you observed in the amount of grey hair on the target area since the baseline visit?

| | |
|---|---|
| Much more grey hair | Score = −3 |
| More grey hair | Score = −2 |
| A little more grey hair | Score = −1 |
| No change in grey hair | Score = 0 |
| A little less grey hair | Score = 1 |

-continued

| | |
|---|---|
| Less grey hair | Score = 2 |
| Much less grey hair | Score = 3 |

What changes have you observed in the total amount of hair on the target area since the baseline visit?

| | |
|---|---|
| Many fewer hairs | Score = −3 |
| Fewer hairs | Score = −2 |
| A little fewer hairs | Score = −1 |
| No change in hairs | Score = 0 |
| A little more hairs | Score = 1 |

-continued

| | |
|---|---|
| More hairs | Score = 2 |
| Much more hairs | Score = 3 |

What overall change have you observed in hair volume in the hair on the target area since the baseline visit?

| | |
|---|---|
| Much less volume | Score = −3 |
| Less volume | Score = −2 |
| A little less volume | Score = −1 |
| No change in volume | Score = 0 |
| A little more volume | Score = 1 |
| More volume | Score = 2 |
| Much more volume | Score = 3 |

What overall change have you observed in hair shine in the hair on the target area since the baseline visit?

| | |
|---|---|
| Much less shine | Score = −3 |
| Less shine | Score = −2 |
| A little less shine | Score = −1 |
| No change in shine | Score = 0 |
| A little more shine | Score = 1 |
| More shine | Score = 2 |
| Much more shine | Score = 3 |

Subject Global Assessment (Protocol Attachment 21.2)

What changes have you noticed in the amount of your grey hair since the baseline visit?

| | |
|---|---|
| Much more | Score = −3 |
| More | Score = −2 |
| A little more | Score = −1 |
| No change | Score = 0 |
| A little less | Score = 1 |
| Less | Score = 2 |
| Much less | Score = 3 |

What changes have you observed in the total numbers of hair on your scalp since the baseline visit?

| | |
|---|---|
| Many fewer | Score = −3 |
| Fewer | Score = −2 |
| A little fewer | Score = −1 |
| No change | Score = 0 |
| A little more | Score = 1 |
| More | Score = 2 |
| Much more | Score = 3 |

What Changes have you noticed in the texture of your hair overall since the baseline visit?

| | |
|---|---|
| Much less | Score = −3 |
| Less | Score = −2 |
| A little less | Score = −1 |
| No change | Score = 0 |
| A little more | Score = 1 |
| More | Score = 2 |
| Much more | Score = 3 |

What changes have you noticed in the shine of your hair overall since the baseline visit?

| | |
|---|---|
| Much less | Score = −3 |
| Less | Score = −2 |
| A little less | Score = −1 |
| No change | Score = 0 |
| A little more | Score = 1 |
| More | Score = 2 |
| Much more | Score = 3 |

What changes have you noticed in the strength (resistance to breaking) of your hair since the baseline visit?

| | |
|---|---|
| Much less | Score = −3 |
| Less | Score = −2 |
| A little less | Score = −1 |
| No change | Score = 0 |
| A little more | Score = 1 |
| More | Score = 2 |
| Much more | Score = 3 |

What changes have you noticed in the softness of your hair since the baseline visit?

| | |
|---|---|
| Much less | Score = −3 |
| Less | Score = −2 |
| A little less | Score = −1 |
| No change | Score = 0 |
| A little more | Score = 1 |
| More | Score = 2 |
| Much more | Score = 3 |

Quality of Life Questionnaire (Protocol Attachment 21.3)
Response choices:

| | |
|---|---|
| Not at all | Score = 4 |
| A little | Score = 3 |
| A lot | Score = 2 |
| Very much | Score = 1 |
| Not relevant | Score = 0 |

1. How embarrassed/self-conscious have you been because of your grey hair?
2. Do you think grey hair makes you look older in appearance than your actual age?
3. Does your greying hair make you feel that you are aging faster?
4. Do you believe your grey hair has been noticed by others?
5. Does your grey hair lower your confidence?
6. Does your grey hair make you feel depressed?
7. Do you feel a need to do something about your grey hair?
8. Have you noticed your hair thinning?
    If yes to question 8:
9. Does your thinning hair lower your confidence?
10. Does your thinning hair make you feel you are aging faster?
11. Do you feel you need to do something about your thinning hair?
12. Does your thinning hair make you feel depressed?

A blinded fourth arm to this clinical study was also added to investigate active TTR plus placebo NTG vs placebo TTR plus placebo NTG. Thirty-three subjects are to be randomized to active TTR and placebo NTG and 6 subjects are to be randomized to placebo NTG and placebo TTR. This arm of the study is identical in all other aspects to the three other arms of the study.

Interim Data Analysis

An interim analysis was performed. FIG. 4A and FIG. 4B show the number of grey hairs counted at baseline and Week 12 for the three first groups. Cell 1 represents subjects who received NTG and TTR, Cell 2 represents subjects who received NTG and placebo TTR, and Cell 3 represents subjects who received placebo NTG and placebo TTR. The number of grey hairs fell in each group, but the change was greatest (11.5%) in NTG and TTR, slightly lower (9.9%) in NTG and placebo TTR, and markedly lower (5.0%) in placebo NTG and placebo TTR. Although the number of subjects was too low to determine statistical significance, it appears that both active groups have better results than placebo.

The interim analysis also showed an improvement in the subject's perception of the amount of grey hair in those who received active products during the trial (FIG. 5A and FIG. 5B). Subjects who received NTG and TTR had a score improvement of 1.67 at Week 12; those who received NTG and placebo TTR had an improvement of 0.33, but those who received placebo had a worsening (−0.80) in the amount of grey hair.

Example 3: A Consumer Perception Study to Assess the Efficacy of Arey Haircare Products on Hair Health and Greying Provided herein are exemplary shampoos and conditioners designed to help people experience better hair health. In this 24-week study, an analysis was first conducted at the 16th-week. 38 participants evaluated the efficacy of the exemplary shampoo and exemplary conditioner, Arey WASH and Arey SMOOTH, to improve hair health attributes and reduce hair greying and shedding and thinning. The study was carried out by an independent party according to the following instructions.

As of 16 weeks, 94.7% of participants saw at least one beneficial hair benefit, with four of the five statistically analyzed parameters demonstrating significant improvement, namely, hair shedding, thinning, texture, and strength. Hair strength significantly improved by Week 4, and improvements were maintained through Week 16, suggesting higher product efficacy at targeting hair strength. Hair shedding, thinning, and texture significantly improved by Week 8 and maintained through Week 16. Hair greying had a perceived improvement in 71.1% of participants after 12 weeks of use. 1 participant, subject #02, saw a 40% reduction in grey hair. After 8 weeks of use, 71.1% of users said that their hair appeared visibly thicker. After just 4 weeks of use, 73% of users said that their hair looked healthier. After just 4 weeks of use, 81.1% of users said that their hair felt softer. After 16 weeks of use, 73.7% of users noticed an improvement in hair texture.

The products were highly regarded by participants; 89.5% would like to keep using them, and 86.8% would recommend the products to a friend. After 16 weeks of using the products, 65.1% of users, reported that the test products improved the hair parameters evaluated in this study, an increase from 48.6% at Week 4.

Hair greying and quality are affected by several factors, including damage, age, oxidative stress, and malnourishment. The melanocortin-1 receptor controls which type of melanin melanocytes produce. It is activated by the melanocyte-stimulating hormone released by the pituitary gland. Research in mice suggests that acute stress can accelerate hair greying, which has been linked to melanocortin-1 and associated signaling pathways. Hair greying and health attributes, including hair shedding, thinning, strength, quality, health, thickness, fullness, and softness, can be improved by scalp and hair nourishment with supplements targeting the affected pathways, nourishing the hair and scalp. Hair greying, hair shedding/thinning, and reduced hair health can negatively affect confidence and self-esteem, negatively impacting mental health, well-being, stress, and social interactions.

An exemplary shampoo and exemplary conditioner of the disclosure, Arey WASH and Arey SMOOTH, targets hair greying and improves hair quality, reduces hair thinning and shedding, improves hair strength, fullness, softness, and overall quality and health, as well as improves the rate of hair growth.

Without being bound by theory, it is thought that the exemplary shampoo, Arey's WASH, stimulates the melanocortin-1 receptor to improve re-pigmentation of the hair. It also contains wasabi extract, sesame seed extract, and *Zanthoxylum bungeanum* fruit extract, which are thought to help the active ingredients penetrate the scalp and access the hair follicle. In addition, ginseng, *Polygonum multiflorum*, and caffeine nourish the root to promote cell turnover and healthier hair growth. Panthenol plays a role in activating the proliferation of cells in the skin barrier, and also helps bind water to the skin and hair, balancing and adding volume to both.

The exemplary conditioning product, SMOOTH, contains hydrolyzed barley protein and coffee extract to build internal strength in the hair strand. Jojoba and shea butter work to seal the cuticle and protect the hair from heat and environmental stress. Finally, panthenol actively attracts and retains moisture in the hair strand, helping it look and feel more volumized.

This trial aimed to examine the efficacy of the test products across a 24-week virtual trial. The participants were required to use the test products at least every other day, and the study period lasted 16 weeks at the time of this report. The primary objective was to evaluate the effect of the shampoo and conditioner on reducing grey hair and improving overall hair health via self-reported questionnaires. The secondary objective was to examine changes in hair softness, growth, texture, and thickness via self-reported questionnaires.

Methods

Participants

A total of 38 participants were recruited for this study. All participants completed the 16 week time point of the study, but one participant did not complete the Week 4 questionnaire and was excluded from statistical analyses. All participants satisfied the following inclusion and exclusion criteria. All 38 participants opted-in at the 16 week time point to continue the study through week 24.

Inclusion Criteria:
Male and female.
Aged 25-50.
Must have 5-30% grey hair.
Must have self-reported concerns about greying hair.
Must be willing to use the shampoo and conditioner in their hair care routine at least every other day for at least 16 weeks.
Must be in good general health.
Must be willing to maintain a consistent hair care routine.

Exclusion Criteria:
Unwilling to follow the routine of the protocol.
Currently participating in another research study.
Any unstable medical condition.
Anyone who currently smokes.
Anyone pregnant, attempting to become pregnant, or breastfeeding.
Anyone allergic to an ingredient in the test product.
Anyone using any prescription or over-the-counter oral or topical product for their hair that targets hair health.
Anyone who does not agree to cease using any other shampoos or conditioners.
Anyone not willing to forgo dying their hair during the study.

Study Design

This was a virtual study that required participants to complete questionnaires at home.

Consent forms describing the study process, instructions, evaluation methods, and bill of rights were provided to participants before study onboarding. Following the consent process, participants completed the baseline survey evaluating hair greying, thinning, shedding, texture, and strength. Participants were instructed to use the product in line with specific guidance provided by the sponsor.

Participants were instructed to wash their hair with at least a silver-dollar-sized amount of WASH shampoo. WASH was applied to wet hair, massaged into the scalp, and left on for 3-5 minutes. After rinsing WASH out, participants were instructed to follow with SMOOTH conditioner (around a quarter to dollar-sized amount) on their mid-shaft to ends of hair strands, which was rinsed off immediately, or left on for a few minutes before rinsing for a deeper conditioning experience. Subjects completed questionnaires at the end of Weeks 4, 8, 12, and 16.

Data Analysis & Statistics

Data was collected using a textual 5-point Likert scale for each question, from "not noticeable" to "severe." Symptom-related questions were answered at baseline and each check-in. The textual Likert data was transformed into numerical values of 1-5, with 1 representing the least favorable/worst outcome (i.e., "severe") and 5 representing the most beneficial response (i.e., "not noticeable") concerning hair complaints. Therefore, an increase in score reports an improvement of that hair parameter during the study period.

Data were checked for normality using the Pearson test. A repeated measure analysis compared participant outcomes at each check-in to their baseline response. Data were analyzed using the repeated-measure one-way ANOVA or Friedman Tests based on the normality of the data. Statistical analyses were performed in GraphPad Prism 9.0, and the significance threshold was set at 0.05. For product-specific questions evaluated only at the Week 4, 8, 12, and 16 check-ins, results were presented as % of subjects reporting each answer on the textual Likert scale.

Results

Arey WASH+SMOOTH Products Significantly Improve a Range of Hair Quality Parameters Subjects self-scored their hair health across various relevant parameters on a 5-point textual Likert scale at baseline and after the test products were used at 4, 8, 12, and 16 weeks. Statistical analysis compared the responses at each check-in to the baseline response. The percentage change was also calculated from baseline to Week 16.

Four of the five evaluated parameters showed a statistically significant improvement from baseline to Week 16 of the study period (P<0.05; FIG. 1, FIG. 2). This data reports that Arey WASH+SMOOTH shampoo and conditioner significantly improves participants' perception of their hair shedding, thinning, texture, and strength. Overall, hair shedding, thinning, texture, and strength improved by over 20% on average across the trial. Significant hair shedding, thinning, and texture improvements were observed after eight weeks of using the product and maintained through Week 16. In addition, a significant improvement in hair strength was observed by Week 4 and maintained through Week 16. Although there was a slight increase (8.9%) in the mean Likert score from baseline, the product did not result in any statistically significant change in the perceived appearance of hair greying.

Arey WASH+SMOOTH Products Improve a Range of Perceived Hair Concerns

Participants used the Arey WASH+SMOOTH shampoo and conditioner for 16 weeks and completed questionnaires after 4, 8, 12, and 16 weeks of use. They responded to product evaluation questions on a 'strongly disagree' to 'strongly agree' scale. The 'strongly agree' and 'agree' responses were combined into a single 'combined agree' outcome to better evaluate the overall agreement that the test product improved the evaluated hair health parameters over time.

Overall, the test product received positive responses from participants, averaging 65.1% agreeing to hair improvement across all 11 parameters evaluated at Week 16 (FIG. 3). Throughout the study, the mean 'combined agree' percentage increased from 48.6% in Week 4 to 65.1% in Week 16, suggesting enhanced outcomes with continued and long-term use. Notably, 73.7% of participants reported improved hair texture and health at Week 16. Further, 81.1% of participants reported in Week 4 that their hair felt softer after using the product. This decreased to 71.1% at Week 16, highlighting the possibility of a drop-off in specific effects.

Arey WASH+SMOOTH Products are Very Highly Regarded by Users

The products were highly regarded by users, with 89.5% of participants agreeing that they would continue using it and 86.8% stating that they would recommend it to a friend. Notably, 94.7% of participants saw at least one beneficial hair care effect.

Discussion

This study provides user perception data on the Arey WASH+SMOOTH shampoo and conditioner duo's effect on hair health outcomes. Hair health parameters were compared between baseline and each study check-in, with all parameters showing minor improvements after 16 weeks of product use. Four of the five statistically analyzed parameters demonstrated significant improvement by Week 8, namely, hair shedding, thinning, texture, and strength. In addition, hair strength improved by Week 4, suggesting higher product efficiency at targeting hair strength. The other statistically analyzed parameter, hair greying, showed an improvement, albeit not significant. It can be hypothesized that this area could continue to improve with more prolonged use, and perhaps significant results are seen within the extended trial period.

Participants were next evaluated on a series of product-specific questions to directly assess the capability of the test product to improve perceived hair health. 65.1% of users, on average, reported that the test product improved the hair parameters evaluated in this study, an increase from 48.6% at Week 4. This may support the hypothesis that participants could see better results with extended use. While statistical analysis showed that hair greying did not improve significantly from baseline, after 12 weeks of use, 71.1% of participants reported fewer grey hairs.

The products were very well received by participants. 89.5% said they would like to keep using them, and 86.8% reported that they would recommend the products to a friend, and 94.7% of participants saw at least one beneficial hair care effect.

Conclusion

The Arey WASH+SMOOTH shampoo and conditioning products improve hair thickness and strength and reduce hair thinning and shedding Participants were positive about their perception of the product, noticing an improvement in hair greying, shedding, thickness, fullness, growth, health, softness, strength, and texture. Arey WASH+SMOOTH products were very well-received; most participants reported that they would recommend them to a friend. Overall, all outcomes improved, and some improvements became more pronounced over time. This suggests enhanced results may be observed for outcomes with further product use, perhaps in the extended trial time points.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A topical hair care formulation comprising:
palmitoyl tetrapeptide-20 amide in an amount of about 2% to about 4% W/W of the formulation;
*Zanthoxylum bungeanum* in an amount of about 0.5% to about 2.5% W/W of the formulation; *Humulus lupulus* in an amount of about 0.5% to about 2.5% W/W of the formulation;
*Polygonum multiflorum* 8% extract in an amount of about 0.05% to about 0.2% W/W of the formulation; one or more of *Sesamum indicum* seed and *Panax ginseng* root;

a conditioning agent selected from the group consisting of *Wasabia japonica* in an amount of about 0.5% to 2.5%, *Glycine soja* in an amount of about 0.5% to 2.5%, Chios mandarin extract in an amount of about 0.5% to 2.5%, *Coffea arabica* seed extract in an amount of about 0.005% to 0.05%, caffeine in an amount of 0.05% to 0.2%, panthenol in an amount of about 0.5% to 2.5%, biotin in an amount of 0.01% to 0.15%, 1,2-hexanediol in an amount of 0.5% to 2.5%, caprylyl glycol in an amount of 0.5% to 2.5%, hydrolyzed barley protein in an amount of 0.5% to 2.5%, amodimethicone in an amount of 0.1% to 1%, guar hydroxypropyltrimonium chloride in an amount of 0.05% to 0.2%, or combinations thereof; and an excipient selected from the group consisting of glycerin, butylene glycol, hydroxyethylcellulose, cocamidopropyl betaine, cetyl esters, cetyl alcohol, stearyl alcohol and combinations thereof.

2. The formulation of claim 1, wherein the palmitoyl tetrapeptide-20 amide is in an amount of about 2% W/W of the formulation.

3. The formulation of claim 1, wherein the *Zanthoxylum burgeanum* is in an amount of about 1.5 W/W of the formulation.

4. The formulation of claim 1, wherein the conditioning agent is about 1 to 1.5% W/W of the formulation.

5. The formulation of claim 1, further comprising *Ononis spinosa* root extract and/or *Avena strigosa* seed extract.

6. The formulation of claim 1, formulated as a serum.

7. The formulation of claim 6, wherein the serum has a pH of about 5-8.

8. The formulation of claim 6, wherein the serum has a viscosity of about 100-1000 centipoise (cps).

9. The formulation of claim 1, formulated as a shampoo.

10. The formulation of claim 9, wherein the shampoo has a pH of about 4-6.

11. The formulation of claim 9, wherein the shampoo has a viscosity of about 1000-5000 centipoise (cps).

12. The formulation of claim 9, wherein the shampoo comprises:
 (i) 2% Palmitoyl Tetrapeptide-20 Amide in glycerin and water; 0.001% *Polygonum multiflorum* 8% root extract; 0.001% *Zanthoxylum bungeanum* fruit extract in glycerin and water; 0.001% *Humulus lupulus* extract in glycerin and water; 0.001% *Sesamum indicum* seed extract in glycerin and water; 0.001% *Glycine soja* germ extract in butylene glycol and water; 0.1% Hydrolyzed barley protein; 0.001% *Wasabia japonica* leaf extract in butylene glycol; 0.01% *Panax ginseng* root extract in glycerin; 0.001% Caffeine;
 0.001% Biotin; 0.01% *Coffea arabica* seed extract; 6% Sodium lauroyl methyl isethionate; 0.25% Citric acid; 2.1% Sodium cocoyl isethionate; 0.1% Sodium benzoate;
 0.1% Potassium sorbate; 0.1% Ethylhexylglycerin; 0.1% Guar hydroxypropyltrimonium chloride; 1% Glycerin; 1% Panthenol; 30% Cocamidopropyl betaine; 0.3% Amodimethicone; 0.8% Fragrance; and Water, or
 (ii) 25-30% Cocamidopropyl Betaine; 6% Sodium Lauroyl Methyl Isethionate; 2.1% Sodium Cocoyl Isethionate; 2% Glycerin and Water and Palmitoyl Tetrapeptide-20 Amide; 1% Glycerin;
 1% Panthenol; 0.8% Sage and Cedar Natural Fragrance ISO9235 ; 0.3% Amodimethicone; 0.25% Citric Acid; 0.1% Hydrolyzed Barley Protein; 0.1% Sodium Benzoate; 0.1% Potassium Sorbate; 0.1% Ethylhexylglycerin; 0.1% Guar Hydroxypropyltrimonium Chloride;
 0.01% *Coffea arabica* Seed Extract; 0.01% Glycerin and *Panax ginseng* Root Extract; 0.001% Water and Glycerin and *Zanthoxylum bungeanum* Fruit Extract; 0.001% Glycerin and Water and *Humulus lupulus* Extract;
 0.001% Glycerin and Water and *Sesamum indicum* Seed Extract; 0.001% Soybean Germ Extract and Water and Butylene Glycol; 0.001% Butylene Glycol and *Wasabia japonica* Leaf Extract; 0.001% of *Polygonum multiflorum* 8% Extract; 0.001% Biotin; 0.001% Caffeine; and Water.

13. The formulation of claim 9, wherein the shampoo is a dry shampoo.

14. The formulation of claim 13, wherein the dry shampoo comprises:
 (i) 53.80% Mica; 19% Aluminum Starch Octenylsuccinate; 7.2% Silica; 2% Palmitoyl Tetrapeptide-20 Amide; 0.7% Caproyl Glycine; 0.7% Undecylenoyl Glycine; 1% *Glycine soja* Germ Extract; 1% *Wasabia japonica* Leaf Extract; 1% *Polygonum multiflorum* 8% root Extract; 0.5% *Humulus lupulus* Flower Extract; 0.5% *Panax ginseng* Root Extract; 0.5% *Zanthoxylum bungeanum* Fruit Extract; 0.5% Glycerin;
 0.5% *Sesamum indicum* Seed Extract; 0.5% Butylene Glycol; 0.5% Water; 0.1% Tocopherol; 1% Sage & Cedar Natural ISO9235; 3% Iron Oxides CI77492; 2% Iron Oxides CI 77499; and 4% Iron Oxides CI 77491; or
 (ii) 53% Mica; 19% Aluminum Starch Octenylsuccinate; 7.2% Silica; 2% Palmitoyl Tetrapeptide-20 Amide; 0.7% Caproyl Glycine; 0.7% Undecylenoyl Glycine; 1% *Glycine soja* Germ Extract; 1% *Wasabia japonica* Leaf Extract; 1% *Polygonum multiflorum* 8% root Extract; 0.5% *Humulus lupulus* Flower Extract; 0.1% *Citrus reticulata* Extract; 0.5% *Panax ginseng* Root Extract; 0.1% Acetyl Tyrosine; 0.5% *Zanthoxylum bungeanum* Fruit Extract; 0.1% Pentylene Glycol; 0.5% Glycerin; 0.3% Gluconolactone; 0.5% *Sesamum indicum* Seed Extract; 0.2% Sodium Benzoate; 0.5% Butylene Glycol; 0.0% Water; 0.1% Tocopherol; 1% Sage & Cedar Natural ISO9235; 3% Iron Oxides CI 77492; 2% Iron Oxides CI 77499; and 4% Iron Oxides CI 77491.

15. The formulation of claim 1, formulated as an exfoliant.

16. The formulation of claim 15, wherein the exfoliant has a pH of about 4-6.

17. The formulation of claim 15, wherein the exfoliant has a viscosity of about 25,000-50,000 cps.

18. The formulation of claim 15, wherein the exfoliant comprises:
 (i) 5.25% Hydroxypropyl Starch Phosphate; 2% Palmitoyl Tetrapeptide-20 Amide in glycerin and water; 1.5% *Zanthoxylum bungeanum* fruit extract in glycerin and water;
 1.5% *Humulus lupulus* extract in glycerin and water; 1.2% *Sesamum indicum* seed extract in glycerin and water; 1% Salicylic Acid; 1% *Wasabia japonica* leaf extract in butylene glycol; 1% *Glycine soja* germ extract in butylene glycol and water; 1% Sorbitan Oleate Decylglucoside Crosspolymer; 0.8% Fragrance; 0.5% Lactic Acid; 0.5% Glycolic Acid;
 0.0% Perlite; 0.3% Ethylhexylglycerin; 0.01% Menthol; 0.001% *Polygonum multiflorum* 8% root extract; 0.001% Caffeine; 0.001% Biotin; Sodium Hydroxide; and Water, or (ii) 5.25% Hydroxypropyl Starch Phosphate; 2% Glycerin and Water and Palmitoyl Tetrapeptide-20 Amide; 2% *Citrus reticulata* Extract and Acetyl Tyrosine and Pentylene Glycol and Gluconolactone and Sodium Benzoate and Water; 1.5% Water and Glycerin and *Zanthoxylum bungeanum* Fruit Extract; 1.5% Glycerin and Water and *Humulus lupulus* Flower Extract; 1.2% Glycerin and Water and *Sesamum indicum* Seed Extract;

1% 1,2-Hexanediol and Caprylyl Glycol; 1% Salicylic Acid; Panthenol; 1% Butylene Glycol and *Wasabia japonica* Leaf Extract; 1% Soybean Germ Extract and Water and Butylene Glycol; 1% Sorbitan Oleate Decylglucoside Crosspolymer;

0.8% Sage and Cedar Natural Fragrance ISO9235 ; 0.5% Lactic Acid; 0.5% Glycolic Acid; 0.5% Perlite; 0.3% Ethylhexylglycerin; 0.01% Menthol; 0.001% *Polygonum multiflorum* Root Extract (8%);

0.001% Caffeine; 0.001% Biotin; Sodium Hydroxide; and Water.

19. The formulation of claim 1, formulated as a conditioner.

20. The conditioner of claim 19, wherein the conditioner has a pH of about 4-6.

21. The conditioner of claim 19, wherein the conditioner has a viscosity of about 8,000-25,000 cps.

22. A topical hair care formulation comprising
*Zanthoxylum bungeanum* in an amount of 0.5% to about 2.5% W/W of the formulation, *Humulus lupulus* in an amount of 0.5% to about 2.5% W/W of the formulation, *Polygonum multiflorum* 8% extract in an amount of about 0.05% to about 0.2% W/W of the formulation; *Sesamum indicum* seed and *Panax ginseng* root;
a conditioning agent selected from the group consisting of *Wasabia japonica* in an amount of about 0.5% to 2.5%, *Glycine soja* in an amount of about 0.5% to 2.5%, Chios mandarin extract in an amount of about 0.5% to 2.5%, *Coffea arabica* seed extract in an amount of about 0.005% to 0.05%, caffeine in an amount of 0.05% to 0.2%, panthenol in an amount of about 0.5% to 2.5%, biotin in an amount of 0.01% to 0.15%, 1,2-hexanediol in an amount of 0.5% to 2.5%, caprylyl glycol in an amount of 0.5% to 2.5%, hydrolyzed barley protein in an amount of 0.5% to 2.5%, amodimethicone in an amount of 0.1% to 1%, guar hydroxypropyltrimonium chloride in an amount of 0.05% to 0.2%, or combinations thereof; and
an excipient selected from the group consisting of glycerin, butylene glycol, hydroxyethylcellulose, cocamidopropyl betaine, cetyl esters, cetyl alcohol, stearyl alcohol and combinations thereof.

23. The topical hair care formulation of claim 22, wherein the formulation provides at least one beneficial hair care effect in a mammalian subject.

24. The topical hair care formulation of claim 22, wherein the formulation is used in combination with a hair follicle treatment to improve the delivery and/or efficacy of the hair follicle treatment.

* * * * *